US012807962B2

(12) United States Patent
Deng et al.

(10) Patent No.: US 12,807,962 B2
(45) Date of Patent: Nov. 24, 2026

(54) HIGH-THROUGHPUT SCREENING PLATFORM FOR LONGEVITY GENES AND ANTI-AGING DRUGS

(71) Applicant: The Regents of the University of California, Oakland, CA (US)

(72) Inventors: Changhui Deng, San Francisco, CA (US); Hao Li, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1186 days.

(21) Appl. No.: 17/273,065

(22) PCT Filed: Sep. 5, 2019

(86) PCT No.: PCT/US2019/049665
§ 371 (c)(1),
(2) Date: Mar. 3, 2021

(87) PCT Pub. No.: WO2020/051281
PCT Pub. Date: Mar. 12, 2020

(65) Prior Publication Data

US 2021/0340552 A1 Nov. 4, 2021

Related U.S. Application Data

(60) Provisional application No. 62/728,008, filed on Sep. 6, 2018.

(51) Int. Cl.
*C12N 15/81* (2006.01)
*C12N 15/09* (2006.01)
*C12Q 1/02* (2006.01)

(52) U.S. Cl.
CPC ............ *C12N 15/81* (2013.01); *C12N 15/09* (2013.01); *C12Q 1/025* (2013.01); *C12N 2800/102* (2013.01); *C12N 2810/70* (2013.01); *C12N 2830/702* (2013.01)

(58) Field of Classification Search
CPC .. C12N 15/81; C12N 15/09; C12N 2800/102; C12N 2830/702; C12N 2810/70; C12Q 1/025
See application file for complete search history.

(56) References Cited

U.S. PATENT DOCUMENTS

2004/0265861 A1* 12/2004 Goldfarb ................ C12Q 1/025 435/254.2

FOREIGN PATENT DOCUMENTS

WO 2007117987 A2 10/2007
WO WO-2017207950 A1 * 12/2017 ........... C07C 49/245

OTHER PUBLICATIONS

Henderson et al. "Mother-daughter asymmetry of pH underlies aging and rejuvenation in yeast", eLIFE, 2014, vol. 3, Article e03504 (Year: 2014).*

Pothoulakis "Organised Natural Structures using Synthetic Biology", Dissertation, 2016, https://doi.org/10.25560/56916 (Year: 2016).*

Sikorski et al. "A System of Shuttle Vectors and Yeast Host Strains Designed for Efficient Manipulation of DNA in *Saccharomyces cerevisiae*", Genetics, 1989, vol. 122, pp. 19-27 (Year: 1989).*

Amen and Kaganovich, Jun. 2017, "Integrative modules for efficient genome engineering in yeast" Microbial Cell, vol. 4, No. 6, p. 182-190 (Year: 2017).*

Henderson et al., 2014, "Mother-daughter asymmetry of pH underlies aging and rejuvenation in yeast" eLIFE, 2014;3:e03504 (Year: 2014).*

Witte et al., Jul. 6, 2017, "Cell cycle entry triggers a switch between two modes of Cdc42 activation during yeast polarization" eLife, 2017;6:e26722 (Year: 2017).*

Janke et al., 2004, "A versatile toolbox for PCR-based tagging ofyeast genes: new fluorescent proteins, moremarkers and promoter substitution cassettes", Yeast, 21:947-962 (Year: 2004).*

Barzilai et al. (2016) "Metformin as a Tool to Target Aging" Cell Metab. 23:1060-1065.

Bjedov et al. (2010) "Mechanisms of life span extension by rapamycin in the fruit fly *Drosophila melanogaster*" Cell Metab. 11(1):35-46.

Breslow et al. (2008) "A comprehensive strategy enabling high-resolution functional analysis of the yeast genome" Nat. Methods 5(8):711-718.

Care, et al. (1999) "The MET3 promoter: a new tool for Candida albicans molecular genetics" Mol. Microbial. 34(4):792-798.

Defossez et al.(1999) "Elimination of replication block protein Fobl extends the life span of yeast mother cells" Mol. Cell, 3:447-455.

Deng et al. (2014) "See & Catch method for studying protein complexes in yeast cells: a technique unifying fluorescence microscopy and mass spectrometry" Methods Mol. Bioi., 11(63):75-95.

Eisenberg et al. (2009) "Induction of autophagy by spermidine promotes longevity" Nat. Cell Bio, 11(11): 1305-1314.

Geber et al. (1992) "Cloning and Characterization of a Candida albicans Maltase Gene Involved in Sucrose Utilization" J Bacterial., 174(21):6992-6996.

Giaever et al. (2002) "Functional profiling of the *Saccharomyces cerevisiae* genome" Nature, 418:387-391.

Flitsch et al. (2016) "Respiration activity monitoring system for any individual well of a 48-well 44/43/39-42 microliter plate" Journal of Biological Engineering, 10(14):1-14.

(Continued)

*Primary Examiner* — Jennifer Dunston
*Assistant Examiner* — Jenna L Persons
(74) *Attorney, Agent, or Firm* — Edward J. Baba; Bozicevic, Field & Francis LLP

(57) ABSTRACT

Compositions, devices, and systems for use in a high-throughput screening platform for identifying anti-aging compounds and/or mutations that extend replicative life span (RLS). Specifically, herein disclosed is a yeast cell daughter-arresting-program (DAP), as well as compositions used in devices and systems that allow measurement of replicative lifespan and identification of agents or mutations that modulate the lifespan.

2 Claims, 30 Drawing Sheets

Specification includes a Sequence Listing.

(56) References Cited

OTHER PUBLICATIONS

Flynn et al. (2013) "Late-life rapamycin treatment reverses age-related heart dysfunction" Aging Cell, 12:851-862.
Henderson et al. (2014) "Mother-daughter asymmetry of pH underlies aging and in yeast" eLife, 3:1-13.
Howitz et al.(2003) "Small molecule activators of sirtuins extend *Saccharomyces cerevisiae* lifespan" Nature 425:191-196.
Janke et al. (2004) "A versatile toolbox for PCR-based tagging of yeast genes: new fluorescent proteins, more markers and promoter substitution cassettes" Yeast, 21:947-962.
Jarolim et al. (2004) "A novel assay for replicative lifespan in *Saccharomyces cerevisiae*" FEMS Yeast Res,. 5(2):169-177.
Jo et at. (2015) "High-throughput analysis of yeast replicative aging using a microfluidic system" PNAS, 11(30):9364-9369.
Kaeberlein et al. (2004) "Sir2-Independent Life Span Extension by Calorie Restriction in Yeast" PLOS Bio., 2(9):1381-1387.
Kaeberlein (2010) "Resveratrol and rapamycin: are they anti-aging drugs?" Bioessays 32:96-99.
Leuker et al. (1997) "Sequence and promoter regulation of the PCK1 gene encoding phosphoenolpyruvate carboxykinase of the fungal pathogen Candida albicans" Gene, 192(2):235-240.
Lindstrom et al. (2009) "The Mother Enrichment Program: A Genetic System for Facile Replicative Life Span Analysis in *Saccharomyces cerevisiae*" Genetics, 183(2):413-422.
Lucanic et al. (2017) "Impact of genetic background and experimental reproducibility on identifying chemical compounds with robust longevity effects" Nat. Commun., 8:14256.
McCormick et al. (2015) "A Comprehensive Analysis of Replicative Lifespan in 4,698 Single-Gene Deletion Strains Uncovers Conserved Mechanisms of Aging" Cell Metab., 22(5):895-906.
Medvedik et al. (2007) "MSN2 andMSN4link calorie restriction and TOR to Sirtuin-mediated lifespan extension in *Saccharomyces cerevisiae*" PLoS Bioi. 5:230-24.
Mortimer et al.(1959) "Life span of individual yeast cells" Nature, 183:1751-1752.
Moskalev et al. (2010) "Pharmacological inhibition ofphosphoinositide 3 and TOR kinases improves survival of *Drosophila melanogaster*" Rejuvenation Res. 13, 246-247.
Nagy (2000) "Cre Recombinase: The Universal Reagent for Genome Tailoring" Genesis 26(2):99-109.
Nakayama et al. (2000) "Tetracycline-Regulatable System to Tightly Control Gene Expression in the Pathogenic Fungus Candida albicans" Infect. Immun. 68(12):6712-6719.
Ottoz, et al. (2014) "Inducible, tightly regulated and growth condition-independent transcription factor in *Saccharomyces cerevisiae*" Nucl. Acids Res. 42(17):eI30.
Pothoulakis (2016) "Organised Natural Structures using Synthetic Biology" Imperial College London. Dissertation, 1-267.
Pothoulakis (2018) "Construction of hybrid regulated mother-specific yeast promoters for inducible differential gene expression" PLoS ONE 13(3): e0194588.
Powers et al. (2006) "Fields, Extension of chronological life span in yeast by decreased TOR pathway signaling" Genes Dev. 20:174-184.
Robida-Stubbs et al. (2012) "TOR signaling and rapamycin influence longevity by regulating SKN-1/Nrfand DAF-16/FoxO" CellMetab. 15(5):713-724.
Schlake et al. (1994) "Use of Mutated FLP Recognition Target (FRT) Sites for the Exchange of Expression Cassettes at Defined Chromosomal Loci" Biochemistry. 33(43):12746-1275.
Tong et al. (2001) "Systematic genetic analysis with ordered arrays of yeast deletion mutants" Science 294, 2364-2368.
Xie et al. (2012) "Molecular phenotyping of aging in single yeast cells using a novel microfluidic device" Molecular phenotyping of aging in single yeast cells using a novel microfluidic device Aging Cell, 11:599-606.
Yan et al. (2008) "Yeast Barcoders: a chemogenomic application of a universal donor-strain collection carrying bar-code identifiers" Nature methods, 5(8)719-725.
Zhang et al. (2012) "Single Cell Analysis of Yeast Replicative Aging Using a New Generation of 38 Microfluidic Device" PLOS One, 7(11):1-10.

* cited by examiner

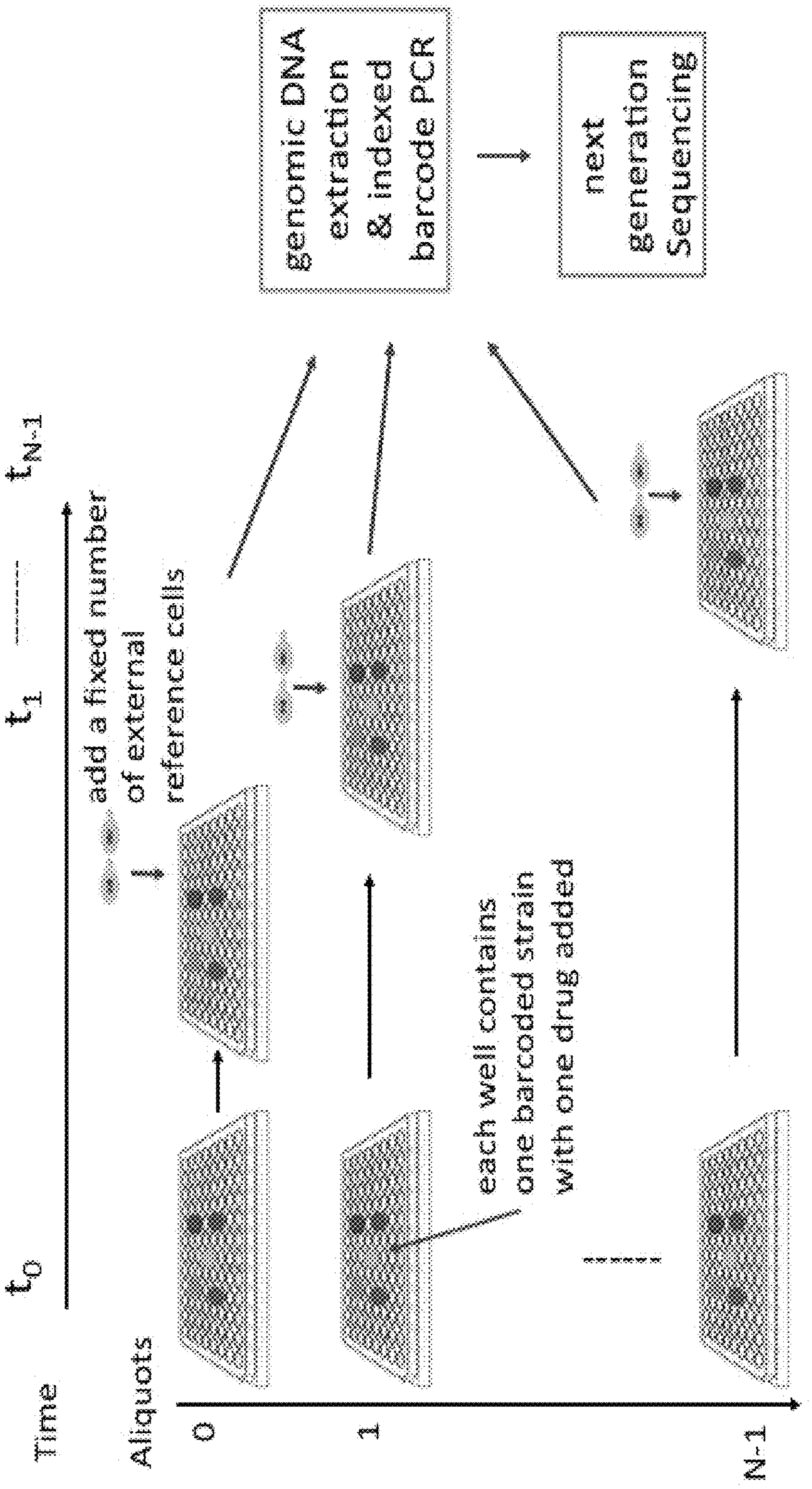
Figure 6. Schematic for identifying compounds that delay aging using barcoded strains with DAP and next generation sequencing.

SEQUENCE LISTING

```
<160> NUMBER OF SEQ ID NOS: 25

<210> SEQ ID NO 1
<211> LENGTH: 11378
<212> TYPE: DNA
<213> ORGANISM: Artificial Sequence
<220> FEATURE:
<223> OTHER INFORMATION: synthetic sequence

<400> SEQUENCE: 1

gaacgcggcc gccagctgaa gcttcgtacg ctgcaggtcg acggatcccc gggtcgagga     60

ctgctctgcg cgccgttggc caaaaatttt ctccacccgt ggtcgccgtc acgtgacagc    120

gacagtcgcg ccagtcgcgc cagctcgcac agcccgccac ctgcgccgtg acgctgcctg    180

gacgcagcgc gctgccgccg gccggcgtgc aaaagtcagg cgatcacaca ttaaaagcta    240

tacattacaa agcgttaata gcgggctgat cattaggttt ccttttcgtg ttgagtagag    300

actctttgca tagcagccat gaagtcttcg acacttctgg tagacttctt ttccttcatt    360

ggcttaccgt tcatcaatct gtcaaaggct tcagaagtgg acatttcgta gtagaaacca    420

cccaaaacac agaagatacc gatagaccag atccagacac ggacgacagt aacaatatca    480

gtccagtttt cagaccacca accgaataag gtaaacatgg tagcgatgat gtcgacagcg    540

aagacggcac cagccaattg ccaggatggg atagaagacc agaatggacc agcagctctg    600

gtaatgaaaa tcaaccagtt ttcagtcaag gaaatttgca agaacataat accgttcata    660

gcaccgaagt tttggataat accacccttt ggtaagaaca tagtagtcaa ggtaatccaa    720

gaacctatag ctaaaactat gcccaaaata atagacatac cccataatct tggtaggttc    780

catttaacgg gctttggaga gtaaggagca ttatcgtaag caatagccaa agtagcaaca    840

tcagcgaaaa tagcgatgaa aacaatcaaa tcaatgtcca aagagttatc caaaatagca    900

atccatagac ccaagaagat ttccaaatgt agagacaaag caatacggta aacaacgtaa    960

gagtacattc tgtgaaaaat ttgtctggag gtcttcaaag catcaataat agcagataga   1020

ccaggagcca agaaaacaat atcagcagca gatctggcag catcagtagc accttcgaca   1080
```

gcaataccag tatcagcctt cttcaaagat ggagcatcgt taacaccatc accagtcata 1140
gcaaccaagt aacctctgtt ttgcaagatt tcaacaactc tgtatttatg ttgtgggaaa 1200
acttcagcga aaccatcggc attttcaaca aaatcagcta attcagaacc tggcatgtca 1260
ccaccgccac ctagacctaa tctttcagcg ttgtaaatgt tggtacccaa acccaattgt 1320
ctacaagttt ccttagcaat accaacagca tcaccagtta acatcttaac tcttagaccc 1380
aagtgtctag cttcgctaac agtttgagca gtatcgtctc ttggtggatc catacatggc 1440
ataacaccca agatttccca gtgaccttca cctctctttc tagcaacacc taaagcacgg 1500
aaccctctag aagccaattc agcaaccttg ttttcgtagt tttcatggac atcttctggg 1560
attgggtgat cttcttcgac agtcttcaag acgaataatg gagcaccctt aacacaaaca 1620
attctttcac cttctggaga ttcgacaacg gcagtaacct tcttggagac agggtcaaat 1680
ggatggaatt ccaaaacctt gtacttggtc aaagcgtcct tagcctttgg atattgcttc 1740
aaagacttca agaaagcctt atcaatagca tccaaaccct tcttctttct ggaagcagcc 1800
aaacaagcag tcaacatcaa gtcgtctgga gaaacacctt caacagtgta tggttcgtgc 1860
aaggacaact tgttcttggt caaagtaccg gttttgtcgg aacacaagat ttcgacacca 1920
gccaaggatt caatagcaga caacttttga acaatggctt gtttcttagc caagtaagca 1980
gcaccgacgg ccatagtggt ggtaacgaca gctggcaaac cgactgggac accaataata 2040
gtaataccta gagtgtatct caagattcta acaataccgt tggttctgta gaaacaagca 2100
gtccagacca acaacaaagt ggcaatgacc aaaaccaata agataatacc aataccgttc 2160
aaaacttcag tgaaatgacc ttgaccacca gcggctttgt taaccaaagc agcagctcta 2220
ccaacgaaag tgttgtcacc ggtagcggta acaaccatga aaccttcacc tctcttaaca 2280
gtggaagaag agaaagtttg gtcaccgtaa tgtttgtcga cagccaaaga ttcaccagta 2340
atagcagatt gatcgatttg caagaaacag tcttcagtga caatacgacc atcagttggg 2400
ataacagtac catcttccaa ttgcaaaata tcacctggga cgacttcgtt ggctggaatt 2460
tcaaccaatt gaccgtctct gataacaaca gcagtgttag ccaaagtctt tttcaattca 2520
tcgacaatag aaccagcttg gaattcttga acgaaaccaa caccagcgtt taacattaac 2580
aaaccacaga taacaccgaa atcgacccaa tcggacaaac cggcagccaa aatagcagcg 2640
gcttccataa cgaattgaat tggaccgacg aaaaacataa cgaacttaac gactaaagat 2700
tctttttcgt cagccatttg attcaaaccg tacttctttc ttcttttcaa aacttcatcg 2760
gaagttaaac cgtaagatgg gtcagtttgt aaatattctt ctggaactgg tctagcttca 2820
ccggcggcaa ctggaccatc gttatcactg tcttcgtcgt cgacaccgtg attagattgt 2880
agttcttcga ttaaagcatc gatatcgtca tcgtcagaag attcagatgc agcgtcatcg 2940
taagtcttag caggcttttc ttgagttggc tgatgagctg aaacagaaga tgctgaagag 3000
gatgatgaag aggatgatgt atcagtcatg cctccgcctc ccttatacaa ctcgtccata 3060
ccgtgtgtaa tcccagcagc tgttacaaac tcaagaagga ccatgtggtc tctcttttcg 3120
ttgggatctt tcgaaagggc agattgtgtg gacaggtaat ggttgtctgg taaaaggaca 3180
gggccatcgc caattggagt attttgttga taatggtctg ctagttgaac gcttccatct 3240
tcaatgttgt gtctaatttt gaagttaact ttgattccat tcttttgttt gtctgccatg 3300
atgtatacat tgtgtgagtt atagttgtat tccaatttgt gtccaagaat gtttccatct 3360
tctttaaaat caataccttt taactcgatt ctattaacaa gggtatcacc ttcaaacttg 3420

```
acttcagcac gtgtcttgta gttcccgtca tctttgaaaa atatagttct ttcctgtaca   3480
taaccttcgg gcatggcact cttgaaaaag tcatgccgtt tcatatgatc tgggtatctt   3540
gaaaagcatt gaacaccata agtgaaagta gtgacaagtg ttggccatgg aacaggtagt   3600
tttccagtag tgcaaataaa tttaagggta agttttccgt atgttgcatc accttcaccc   3660
tctccactga cagaaaattt gtgcccatta acatcaccat ctaattcaac aagaattggg   3720
acaactccag tgaaaagttc ttctccttta ctcatggtgc tagctttaaa gtatagatag   3780
aattgattgc tgcttatgag gatatggatt tagagctaat agttgtaata gaaataaaag   3840
ccatttagaa taggaattga atacaatttt atgagcttta aatatttaat gatgaatagt   3900
gcgtttagaa cgcttcatca tgcttcaaca agcttctgca aacctcattt gagtagcaat   3960
agctgtttac tttttccgc gactttattc gaagttatgg tgaacttttc gtggtttcac   4020
acctaataac gcccagcggt agtacaattc aaagtagtag gtaccaatgg tagtactagt   4080
gggtgatagt agcaaatttc tctatgaaaa tgaattgttg ctctgcaatg atgttaatgt   4140
ggacatgaca tgaattttcg cgatatgttg atgtaaataa taacatgatt ttcgtggatc   4200
atttcgtaaa ccataggttt atttcgtgaa ttactaagag aaaggcatag aaacaggact   4260
tgcgaaccct ttctgtaata tgtcataata tttcaataca cgcacaaaaa aggtacgtta   4320
atttccatgg taatcgtgta tttagttaca tcacttttcg tgacacacat gaatacattt   4380
gcccttaagc cctgtgtagg attgatttct tttttcgtga cgcacatgtc ttcaactgca   4440
tcaatttcca tgagacacac acgtctacca tgttgtcaga tctcatgaat ctttcatgta   4500
ttcattcaca tcattttcgt ggatcctcta attgtatcga gatcactttt cgtgatccgc   4560
taatcagcga cggtcacatt aggtttgcca agtcagggta tgaaccatac gatcagtttt   4620
cgtgaacctg gtacgtatat tgtggcgttt gtgtatattt tcattctttg acaacaatca   4680
ataccaacct caaataggaa aagtaataag tttggcgtta caccccaaaa gacgccaaac   4740
ggatcgaact tactcaatag caattagcga gacaaaacct acgttaagac ctgtaaccga   4800
tttatcaaag cactctgcgg ttctttcttg ggaatattac ctggacattt tgtgccctca   4860
agaaacgagg ctctacgagc ctgttggagc ccctcagaca ttagccgcca cgaatcaaac   4920
tttttacgcg attcggccca aatcagtttc tcacagatca ttcgtagagt gaaaaagcac   4980
atcgattatt tgatacccct ttgggttaat tactgttgag gtcttttcta tttctgattg   5040
aaatttttgc tccagcatta tagcatgctg gttttttttt taaattgatg tatctcatcg   5100
caggcacggg cagtacagtg ccctgagcgt agggaaaaat gaaaaaaagg atgtaacttt   5160
taacataatt ccagcacgca gcgattgggt ataatgaaga ttgttaagtt caacaacatg   5220
tgaaattctt agctccgcaa cttgcttgaa ttatgagctc taagattcaa gaagtaaata   5280
ggtcatataa tggaatgata gtagtacttg ataaaggaac catgtgatct tacgttgata   5340
tgaaaataat tctctcacag aagtcagttt gtatgactaa catagagagt aattgctttt   5400
cggataaaat cgcacctaac aaagattacc ttttgtaaag cctccagaac agctatgaat   5460
gttcgttatt ctacgcactt tctttcatac atcttgatcc gcctttttttg atgtaggttt   5520
taacgcggca aaacatatta atttttctga tttggaaaaa taaagagtta gttctgccac   5580
gccattttaa gtccaaaggc acaattttac gttggaacta aacggtaaag atcaaatatc   5640
acctttattc tttttggta tgcatcgatt tctttgccag taagaactac gtgcaactct   5700
acattagatc aaaatataac ggatcataaa tgcaaacaac atttgtccaa aagaaacaaa   5760
aatgttggcg tttgtctcga acatgacaca atactccttg atcgagggac attgcccgat   5820
```

-continued

```
taactatgat ttatactttt tactacaggt actcgttctc cctactattt caccagtggc   5880
gcgccagatc tgtttagctt gcctcgtccc cgccgggtca cccggccagc gacatggagg   5940
cccagaatac cctccttgac agtcttgacg tgcgcagctc aggggcatga tgtgactgtc   6000
gcccgtacat ttagcccata catccccatg tataatcatt tgcatccata cattttgatg   6060
gccgcacggc gcgaagcaaa aattacggct cctcgctgca gacctgcgag cagggaaacg   6120
ctcccctcac agacgcgttg aattgtcccc acgccgcgcc cctgtagaga aatataaaag   6180
gttaggattt gccactgagg ttcttctttc atatacttcc ttttaaaatc ttgctaggat   6240
acagttctca catcacatcc gaacataaac aaccatgggt aaaaagcctg aactcaccgc   6300
gacgtctgtc gagaagtttc tgatcgaaaa gttcgacagc gtctccgacc tgatgcagct   6360
ctcggagggc gaagaatctc gtgctttcag cttcgatgta ggagggcgtg gatatgtcct   6420
gcgggtaaat agctgcgccg atggtttcta caaagatcgt tatgtttatc ggcactttgc   6480
atcggccgcg ctcccgattc cggaagtgct tgacattggg gaattcagcg agagcctgac   6540
ctattgcatc tcccgccgtg cacagggtgt cacgttgcaa gacctgcctg aaaccgaact   6600
gcccgctgtt ctgcagccgg tcgcggaggc catggatgcg atcgctgcgg ccgatcttag   6660
ccagacgagc gggttcggcc cattcggacc gcaaggaatc ggtcaataca ctacatggcg   6720
tgatttcata tgcgcgattg ctgatcccca tgtgtatcac tggcaaactg tgatggacga   6780
caccgtcagt gcgtccgtcg cgcaggctct cgatgagctg atgctttggg ccgaggactg   6840
ccccgaagtc cggcacctcg tgcacgcgga tttcggctcc aacaatgtcc tgacggacaa   6900
tggccgcata acagcggtca ttgactggag cgaggcgatg ttcggggatt cccaatacga   6960
ggtcgccaac atcttcttct ggaggccgtg gttggcttgt atggagcagc agacgcgcta   7020
cttcgagcgg aggcatccgg agcttgcagg atcgccgcgg ctccgggcgt atatgctccg   7080
cattggtctt gaccaactct atcagagctt ggttgacggc aatttcgatg atgcagcttg   7140
ggcgcagggt cgatgcgacg caatcgtccg atccggagcc gggactgtcg ggcgtacaca   7200
aatcgcccgc agaagcgcgg ccgtctggac cgatggctgt gtagaagtac tcgccgatag   7260
tggaaaccga cgccccagca ctcgtccgag ggcaaaggaa taatctcgag tcatgtaatt   7320
agttatgtca cgcttacatt cacgccctcc ccccacatcc gctctaaccg aaaaggaagg   7380
agttagacaa cctgaagtct aggtccctat ttattttttt atagttatgt tagtattaag   7440
aacgttattt atatttcaaa tttttctttt ttttctgtac agacgcgtgt acgcatgtaa   7500
cattatactg aaaaccttgc ttgagaaggt tttgggacgc tcgaaggctt taacgagctc   7560
agtacggatt agaagccgcc gagcgggtga cagccctccg aaggaagact ctcctccgtg   7620
cgtcctcgtc ttcaccggtc gcgttcctga aacgcagatg tgcctcgcgc cgcactgctc   7680
cgaacaataa agattctaca atactagctt ttatggttat gaagaggaaa aattggcagt   7740
aacctggccc cacaaacctt caaatgaacg aatcaaatta acaaccatag gatgataatg   7800
cgattagttt tttagcctta tttctggggt aattaatcag cgaagcgatg atttttgatc   7860
tattaacaga tatataaatg caaaaactgc ataaccactt taactaatac tttcaacatt   7920
ttcggtttgt attacttctt attcaaatgt aataaaagta tcaacaaaaa attgttaata   7980
tacctctata ctttaacgtc aaggagaaaa aacactagta ccatgagtaa aggagaagaa   8040
cttttcactg gagttgtccc aattcttgtt gaattagatg gtgatgttaa tgggcacaaa   8100
ttttctgtca gtggagaggg tgaaggtgat gcaacatacg gaaaacttac ccttaaattt   8160
```

-continued atttgcacta ctggaaaact acctgttcca tggccaacac ttgtcactac tttcacttat 8220
ggtgttcaat gcttttcaag atacccagat catatgaaac ggcatgactt tttcaagagt 8280
gccatgcccg aaggttatgt acaggaaaga actatatttt tcaaagatga cgggaactac 8340
aagacacgtg ctgaagtcaa gtttgaaggt gatacccttg ttaatagaat cgagttaaaa 8400
ggtattgatt ttaaagaaga tggaaacatt cttggacaca aattggaata caactataac 8460
tcacacaatg tatacatcat ggcagacaaa caaaagaatg gaatcaaagt taacttcaaa 8520
attagacaca acattgaaga tggaagcgtt caactagcag accattatca acaaaatact 8580
ccaattggcg atggccctgt ccttttacca gacaaccatt acctgtccac acaatctgcc 8640
ctttcgaaag atcccaacga aaagagagac cacatggtcc ttcttgagtt tgtaacagct 8700
gctgggatta cacatggcat ggatgaacta tacaaatagg gcctcgaggc ccgctattaa 8760
cgctttgtaa tgtatagctt ttaatgtgtg atcgcctgac ttttgcacgc cggccggcgg 8820
cagcgcgctg cgtccaggca gcgtcacggc gcaggtggcg ggctgtgcga gctggcgcga 8880
ctggcgcgac tgtcgctgtc acgtgacggc gaccacgggt ggagaaaatt tttggccaac 8940
ggcgcgcaga gcagtcctcg aatcgatgat atcagatcca ctagtggcct atgcggccgc 9000
ggatctgccg gtctccctat agtgagtcgt attaatttcg ataagccagg ttaacctgca 9060
ttaatgaatc ggccaacgcg cggggagagg cggtttgcgt attgggcgct cttccgcttc 9120
ctcgctcact gactcgctgc gctcggtcgt tcggctgcgg cgagcggtat cagctcactc 9180
aaaggcggta atacggttat ccacagaatc aggggataac gcaggaaaga acatgtgagc 9240
aaaaggccag caaaaggcca ggaaccgtaa aaaggccgcg ttgctggcgt ttttccatag 9300
gctccgcccc cctgacgagc atcacaaaaa tcgacgctca agtcagaggt ggcgaaaccc 9360
gacaggacta taaagatacc aggcgtttcc ccctggaagc tccctcgtgc gctctcctgt 9420
tccgaccctg ccgcttaccg gatacctgtc cgcctttctc ccttcgggaa gcgtggcgct 9480
ttctcaatgc tcacgctgta ggtatctcag ttcggtgtag gtcgttcgct ccaagctggg 9540
ctgtgtgcac gaaccccccg ttcagcccga ccgctgcgcc ttatccggta actatcgtct 9600
tgagtccaac ccggtaagac acgacttatc gccactggca gcagccactg gtaacaggat 9660
tagcagagcg aggtatgtag gcggtgctac agagttcttg aagtggtggc ctaactacgg 9720
ctacactaga aggacagtat ttggtatctg cgctctgctg aagccagtta ccttcggaaa 9780
aagagttggt agctcttgat ccggcaaaca aaccaccgct ggtagcggtg gtttttttgt 9840
ttgcaagcag cagattacgc gcagaaaaaa aggatctcaa gaagatcctt tgatcttttc 9900
tacggggtct gacgctcagt ggaacgaaaa ctcacgttaa gggattttgg tcatgagatt 9960
atcaaaaagg atcttcacct agatcctttt aaattaaaaa tgaagtttta aatcaatcta 10020
aagtatatat gagtaaactt ggtctgacag ttaccaatgc ttaatcagtg aggcacctat 10080
ctcagcgatc tgtctatttc gttcatccat agttgcctga ctccccgtcg tgtagataac 10140
tacgatacgg gagggcttac catctggccc cagtgctgca atgataccgc gagacccacg 10200
ctcaccggct ccagatttat cagcaataaa ccagccagcc ggaagggccg agcgcagaag 10260
tggtcctgca actttatccg cctccatcca gtctattaat tgttgccggg aagctagagt 10320
aagtagttcg ccagttaata gtttgcgcaa cgttgttgcc attgctacag gcatcgtggt 10380
gtcacgctcg tcgtttggta tggcttcatt cagctccggt tcccaacgat caaggcgagt 10440
tacatgatcc cccatgttgt gcaaaaaagc ggttagctcc ttcggtcctc cgatcgttgt 10500
cagaagtaag ttggccgcag tgttatcact catggttatg gcagcactgc ataattctct 10560

```
tactgtcatg ccatccgtaa gatgcttttc tgtgactggt gagtactcaa ccaagtcatt  10620

ctgagaatag tgtatgcggc gaccgagttg ctcttgcccg gcgtcaatac gggataatac  10680

cgcgccacat agcagaactt taaaagtgct catcattgga aaacgttctt cggggcgaaa  10740

actctcaagg atcttaccgc tgttgagatc cagttcgatg taacccactc gtgcacccaa  10800

ctgatcttca gcatctttta ctttcaccag cgtttctggg tgagcaaaaa caggaaggca  10860

aaatgccgca aaaaagggaa taagggcgac acggaaatgt tgaatactca tactcttcct  10920

ttttcaatat tattgaagca tttatcaggg ttattgtctc atgagcggat acatatttga  10980

atgtatttag aaaaataaac aaataggggt tccgcgcaca tttccccgaa aagtgccacc  11040

tgacgtctaa gaaaccatta ttatcatgac attaacctat aaaaataggc gtatcacgag  11100

gccctttcgt ctcgcgcgtt tcggtgatga cggtgaaaac ctctgacaca tgcagctccc  11160

ggagacggtc acagcttgtc tgtaagcgga tgccgggagc agacaagccc gtcagggcgc  11220

gtcagcgggt gttggcgggt gtcggggctg gcttaactat gcggcatcag agcagattgt  11280

actgagagtg caccatatgg acatattgtc gttagaacgc ggctacaatt aatacataac  11340

cttatgtatc atacacatac gatttaggtg acactata                          11378
```

<210> SEQ ID NO 2
<211> LENGTH: 11354
<212> TYPE: DNA
<213> ORGANISM: Artificial Sequence
<220> FEATURE:
<223> OTHER INFORMATION: synthetic sequence

<400> SEQUENCE: 2

```
gaacgcggcc gccagctgaa gcttcgtacg ctgcaggtcg acggatcccc gggtcgagga     60

ctgctctgcg cgccgttggc caaaaatttt ctccacccgt ggtcgccgtc acgtgacagc    120

gacagtcgcg ccagtcgcgc cagctcgcac agcccgccac ctgcgccgtg acgctgcctg    180

gacgcagcgc gctgccgccg gccggcgtgc aaaagtcagg cgatcacaca ttaaaagcta    240

tacattacaa agcgttaata gcgggctgat cattaggttt ccttttcgtg ttgagtagag    300

actctttgca tagcagccat gaagtcttcg acacttctgg tagacttctt ttccttcatt    360

ggcttaccgt tcatcaatct gtcaaaggct tcagaagtgg acatttcgta gtagaaacca    420

cccaaaacac agaagatacc gatagaccag atccagacac ggacgacagt aacaatatca    480

gtccagtttt cagaccacca accgaataag gtaaacatgg tagcgatgat gtcgacagcg    540

aagacggcac cagccaattg ccaggatggg atagaagacc agaatggacc agcagctctg    600

gtaatgaaaa tcaaccagtt ttcagtcaag gaaatttgca agaacataat accgttcata    660

gcaccgaagt tttggataat accacccttt ggtaagaaca tagtagtcaa ggtaatccaa    720

gaacctatag ctaaaactat gcccaaaata atagacatac cccataatct tggtaggttc    780

catttaacgg gctttggaga gtaaggagca ttatcgtaag caatagccaa agtagcaaca    840

tcagcgaaaa tagcgatgaa aacaatcaaa tcaatgtcca aagagttatc caaaatagca    900

atccatagac ccaagaagat ttccaaatgt agagacaaag caatacggta aacaacgtaa    960

gagtacattc tgtgaaaaat ttgtctggag gtcttcaaag catcaataat agcagataga   1020

ccaggagcca agaaaacaat atcagcagca gatctggcag catcagtagc accttcgaca   1080

gcaataccag tatcagcctt cttcaaagat ggagcatcgt taacaccatc accagtcata   1140

gcaaccaagt aacctctgtt ttgcaagatt tcaacaactc tgtatttatg ttgtgggaaa   1200
```

acttcagcga aaccatcggc attttcaaca aaatcagcta attcagaacc tggcatgtca 1260
ccaccgccac ctagacctaa tctttcagcg ttgtaaatgt tggtacccaa acccaattgt 1320
ctacaagttt ccttagcaat accaacagca tcaccagtta acatcttaac tcttagaccc 1380
aagtgtctag cttcgctaac agtttgagca gtatcgtctc ttggtggatc catacatggc 1440
ataacaccca agatttccca gtgaccttca cctctctttc tagcaacacc taaagcacgg 1500
aaccctctag aagccaattc agcaaccttg ttttcgtagt tttcatggac atcttctggg 1560
attgggtgat cttcttcgac agtcttcaag acgaataatg gagcaccctt aacacaaaca 1620
attctttcac cttctggaga ttcgacaacg gcagtaacct tcttggagac agggtcaaat 1680
ggatggaatt ccaaaacctt gtacttggtc aaagcgtcct tagcctttgg atattgcttc 1740
aaagacttca agaaagcctt atcaatagca tccaaaccct tcttctttct ggaagcagcc 1800
aaacaagcag tcaacatcaa gtcgtctgga gaaacacctt caacagtgta tggttcgtgc 1860
aaggacaact tgttcttggt caaagtaccg gttttgtcgg aacacaagat ttcgacacca 1920
gccaaggatt caatagcaga caacttttga acaatggctt gtttcttagc caagtaagca 1980
gcaccgacgg ccatagtggt ggtaacgaca gctggcaaac cgactgggac accaataata 2040
gtaataccta gagtgtatct caagattcta acaataccgt tggttctgta gaaacaagca 2100
gtccagacca acaacaaagt ggcaatgacc aaaaccaata agataatacc aataccgttc 2160
aaaacttcag tgaaatgacc ttgaccacca gcggctttgt taaccaaagc agcagctcta 2220
ccaacgaaag tgttgtcacc ggtagcggta acaaccatga aaccttcacc tctcttaaca 2280
gtggaagaag agaaagtttg gtcaccgtaa tgtttgtcga cagccaaaga ttcaccagta 2340
atagcagatt gatcgatttg caagaaacag tcttcagtga caatacgacc atcagttggg 2400
ataacagtac catcttccaa ttgcaaaata tcacctggga cgacttcgtt ggctggaatt 2460
tcaaccaatt gaccgtctct gataacaaca gcagtgttag ccaaagtctt tttcaattca 2520
tcgacaatag aaccagcttg gaattcttga acgaaaccaa caccagcgtt taacattaac 2580
aaaccacaga taacaccgaa atcgacccaa tcggacaaac cggcagccaa aatagcagcg 2640
gcttccataa cgaattgaat tggaccgacg aaaaacataa cgaacttaac gactaaagat 2700
tctttttcgt cagccatttg attcaaaccg tacttctttc ttcttttcaa aacttcatcg 2760
gaagttaaac cgtaagatgg gtcagtttgt aaatattctt ctggaactgg tctagcttca 2820
ccggcggcaa ctggaccatc gttatcactg tcttcgtcgt cgacaccgtg attagattgt 2880
agttcttcga ttaaagcatc gatatcgtca tcgtcagaag attcagatgc agcgtcatcg 2940
taagtcttag caggcttttc ttgagttggc tgatgagctg aaacagaaga tgctgaagag 3000
gatgatgaag aggatgatgt atcagtcatg cctccgcctc ctttatataa ttcatccata 3060
ccatataaga acaggtggtg gcggccctcg gagcgctcgt actgttccac gatggtgtag 3120
tcctcgttgt gggaggtgat gtccagcttg gtgtccacgt agtagtagcc gggcagttgc 3180
acgggcttct tggccatgta gatggtcttg aactccacca ggtagtggcc gccgtccttc 3240
agcttcaggg cctggtggat ctcgcccttc agcacgccgt cgcgggggta caggcgctcg 3300
gtggaggcct cccagcccat ggtcttcttc tgcattacgg ggccgtcggg ggggaagttg 3360
gtgccgcgca tcttcacctt gtagatcagc gtgccgtcct gcagggagga gtcctgggtc 3420
acggtcacca gaccgccgtc ctcgaagttc atcacgcgct cccacttgaa gccctcgggg 3480
aaggacagct tcttgtaatc ggggatgtcg gcggggtgct tcacgtacgc cttggagccg 3540
tacatgaact ggggggacag gatgtcccag gcgaagggca gggggccgcc cttggtcacc 3600
ttcagcttgg cggtctgggt gccctcgtag gggcggccct cgccctcgcc ctcgatctcg 3660
aactcgtggc cgttcatgga gccctccatg cgcaccttga agcgcatgaa ctctttgatg 3720
acctcctcgc ccttgctcac catggtgcta gctttaaagt atagatagaa ttgattgctg 3780
cttatgagga tatggattta gagctaatag ttgtaataga aataaaagcc atttagaata 3840
ggaattgaat acaattttat gagctttaaa tatttaatga tgaatagtgc gtttagaacg 3900
cttcatcatg cttcaacaag cttctgcaaa cctcatttga gtagcaatag ctgtttactt 3960
ttttccgcga ctttattcga agttatggtg aacttttcgt ggtttcacac ctaataacgc 4020
ccagcggtag tacaattcaa agtagtaggt accaatggta gtactagtgg gtgatagtag 4080
caaatttctc tatgaaaatg aattgttgct ctgcaatgat gttaatgtgg acatgacatg 4140
aattttcgcg atatgttgat gtaaataata acatgatttt cgtggatcat ttcgtaaacc 4200
ataggtttat ttcgtgaatt actaagagaa aggcatagaa acaggacttg cgaacccttt 4260
ctgtaatatg tcataatatt tcaatacacg cacaaaaaag gtacgttaat ttccatggta 4320
atcgtgtatt tagttacatc acttttcgtg acacacatga atacatttgc ccttaagccc 4380
tgtgtaggat tgatttcttt tttcgtgacg cacatgtctt caactgcatc aatttccatg 4440
agacacacac gtctaccatg ttgtcagatc tcatgaatct ttcatgtatt cattcacatc 4500
attttcgtgg atcctctaat tgtatcgaga tcacttttcg tgatccgcta atcagcgacg 4560
gtcacattag gtttgccaag tcagggtatg aaccatacga tcagttttcg tgaacctggt 4620
acgtatattg tggcgtttgt gtatattttc attctttgac aacaatcaat accaacctca 4680
aataggaaaa gtaataagtt tggcgttaca ccccaaaaga cgccaaacgg atcgaactta 4740
ctcaatagca attagcgaga caaaacctac gttaagacct gtaaccgatt tatcaaagca 4800
ctctgcggtt ctttcttggg aatattacct ggacattttg tgccctcaag aaacgaggct 4860
ctacgagcct gttggagccc ctcagacatt agccgccacg aatcaaactt tttacgcgat 4920
tcggcccaaa tcagtttctc acagatcatt cgtagagtga aaaagcacat cgattatttg 4980
ataccccttt gggttaatta ctgttgaggt cttttctatt tctgattgaa atttttgctc 5040
cagcattata gcatgctggt ttttttttta aattgatgta tctcatcgca ggcacgggca 5100
gtacagtgcc ctgagcgtag ggaaaaatga aaaaaaggat gtaactttta acataattcc 5160
agcacgcagc gattgggtat aatgaagatt gttaagttca acaacatgtg aaattcttag 5220
ctccgcaact tgcttgaatt atgagctcta agattcaaga agtaaatagg tcatataatg 5280
gaatgatagt agtacttgat aaaggaacca tgtgatctta cgttgatatg aaaataattc 5340
tctcacagaa gtcagtttgt atgactaaca tagagagtaa ttgcttttcg gataaaatcg 5400
cacctaacaa agattacctt ttgtaaagcc tccagaacag ctatgaatgt tcgttattct 5460
acgcactttc tttcatacat cttgatccgc cttttttgat gtaggtttta acgcggcaaa 5520
acatattaat ttttctgatt tggaaaaata aagagttagt tctgccacgc cattttaagt 5580
ccaaaggcac aattttacgt tggaactaaa cggtaaagat caaatatcac ctttattctt 5640
ttttggtatg catcgatttc tttgccagta agaactacgt gcaactctac attagatcaa 5700
aatataacgg atcataaatg caaacaacat ttgtccaaaa gaaacaaaaa tgttggcgtt 5760
tgtctcgaac atgacacaat actccttgat cgagggacat tgcccgatta actatgattt 5820
atacttttta ctacaggtac tcgttctccc tactatttca ccagtggcgc gccagatctg 5880
tttagcttgc ctcgtccccg ccgggtcacc cggccagcga catggaggcc cagaataccc 5940
tccttgacag tcttgacgtg cgcagctcag gggcatgatg tgactgtcgc ccgtacattt 6000
agcccataca tccccatgta taatcatttg catccataca ttttgatggc cgcacggcgc 6060
gaagcaaaaa ttacggctcc tcgctgcaga cctgcgagca gggaaacgct cccctcacag 6120
acgcgttgaa ttgtccccac gccgcgcccc tgtagagaaa tataaaaggt taggatttgc 6180
cactgaggtt cttctttcat atacttcctt ttaaaatctt gctaggatac agttctcaca 6240
tcacatccga acataaacaa ccatgggtaa aaagcctgaa ctcaccgcga cgtctgtcga 6300
gaagtttctg atcgaaaagt tcgacagcgt ctccgacctg atgcagctct cggagggcga 6360
agaatctcgt gctttcagct tcgatgtagg agggcgtgga tatgtcctgc gggtaaatag 6420
ctgcgccgat ggtttctaca aagatcgtta tgtttatcgg cactttgcat cggccgcgct 6480
cccgattccg gaagtgcttg acattgggga attcagcgag agcctgacct attgcatctc 6540
ccgccgtgca cagggtgtca cgttgcaaga cctgcctgaa accgaactgc ccgctgttct 6600
gcagccggtc gcggaggcca tggatgcgat cgctgcggcc gatcttagcc agacgagcgg 6660
gttcggccca ttcggaccgc aaggaatcgg tcaatacact acatggcgtg atttcatatg 6720
cgcgattgct gatccccatg tgtatcactg gcaaactgtg atggacgaca ccgtcagtgc 6780
gtccgtcgcg caggctctcg atgagctgat gctttgggcc gaggactgcc ccgaagtccg 6840
gcacctcgtg cacgcggatt tcggctccaa caatgtcctg acggacaatg gccgcataac 6900
agcggtcatt gactggagcg aggcgatgtt cggggattcc caatacgagg tcgccaacat 6960
cttcttctgg aggccgtggt tggcttgtat ggagcagcag acgcgctact tcgagcggag 7020
gcatccggag cttgcaggat cgccgcggct ccgggcgtat atgctccgca ttggtcttga 7080
ccaactctat cagagcttgg ttgacggcaa tttcgatgat gcagcttggg cgcagggtcg 7140
atgcgacgca atcgtccgat ccggagccgg gactgtcggg cgtacacaaa tcgcccgcag 7200
aagcgcggcc gtctggaccg atggctgtgt agaagtactc gccgatagtg gaaaccgacg 7260
ccccagcact cgtccgaggg caaaggaata atctcgagtc atgtaattag ttatgtcacg 7320
cttacattca cgccctcccc ccacatccgc tctaaccgaa aaggaaggag ttagacaacc 7380
tgaagtctag gtccctattt atttttttat agttatgtta gtattaagaa cgttatttat 7440
atttcaaatt tttctttttt ttctgtacag acgcgtgtac gcatgtaaca ttatactgaa 7500
aaccttgctt gagaaggttt tgggacgctc gaaggcttta acgagctcag tacggattag 7560
aagccgccga gcgggtgaca gccctccgaa ggaagactct cctccgtgcg tcctcgtctt 7620
caccggtcgc gttcctgaaa cgcagatgtg cctcgcgccg cactgctccg aacaataaag 7680
attctacaat actagctttt atggttatga agaggaaaaa ttggcagtaa cctggcccca 7740
caaaccttca aatgaacgaa tcaaattaac aaccatagga tgataatgcg attagttttt 7800
tagccttatt tctggggtaa ttaatcagcg aagcgatgat ttttgatcta ttaacagata 7860
tataaatgca aaaactgcat aaccacttta actaatactt tcaacatttt cggtttgtat 7920
tacttcttat tcaaatgtaa taaaagtatc aacaaaaaat tgttaatata cctctatact 7980
ttaacgtcaa ggagaaaaaa cactagtacc atggtgagca agggcgagga ggtcatcaaa 8040
gagttcatgc gcttcaaggt gcgcatggag ggctccatga acggccacga gttcgagatc 8100
gagggcgagg gcgagggccg cccctacgag ggcacccaga ccgccaagct gaaggtgacc 8160
aagggcggcc ccctgccctt cgcctgggac atcctgtccc cccagttcat gtacggctcc 8220
aaggcgtacg tgaagcaccc cgccgacatc cccgattaca agaagctgtc cttccccgag 8280
ggcttcaagt gggagcgcgt gatgaacttc gaggacggcg gtctggtgac cgtgacccag 8340

```
gactcctccc tgcaggacgg cacgctgatc tacaaggtga agatgcgcgg caccaacttc   8400
ccccccgacg gccccgtaat gcagaagaag accatgggct gggaggcctc caccgagcgc   8460
ctgtaccccc gcgacggcgt gctgaagggc gagatccacc aggccctgaa gctgaaggac   8520
ggcggccact acctggtgga gttcaagacc atctacatgg ccaagaagcc cgtgcaactg   8580
cccggctact actacgtgga caccaagctg gacatcacct cccacaacga ggactacacc   8640
atcgtggaac agtacgagcg ctccgagggc cgccaccacc tgttcctgta cggcatggac   8700
gagctgtaca agtaaggcct cgaggcccgc tattaacgct ttgtaatgta tagcttttaa   8760
tgtgtgatcg cctgactttt gcacgccggc cggcggcagc gcgctgcgtc caggcagcgt   8820
cacggcgcag gtggcgggct gtgcgagctg gcgcgactgg cgcgactgtc gctgtcacgt   8880
gacggcgacc acgggtggag aaaatttttg gccaacggcg cgcagagcag tcctcgaatc   8940
gatgatatca gatccactag tggcctatgc ggccgcggat ctgccggtct ccctatagtg   9000
agtcgtatta atttcgataa gccaggttaa cctgcattaa tgaatcggcc aacgcgcggg   9060
gagaggcggt ttgcgtattg ggcgctcttc cgcttcctcg ctcactgact cgctgcgctc   9120
ggtcgttcgg ctgcggcgag cggtatcagc tcactcaaag gcggtaatac ggttatccac   9180
agaatcaggg gataacgcag gaaagaacat gtgagcaaaa ggccagcaaa aggccaggaa   9240
ccgtaaaaag gccgcgttgc tggcgttttt ccataggctc cgcccccctg acgagcatca   9300
caaaaatcga cgctcaagtc agaggtggcg aaacccgaca ggactataaa gataccaggc   9360
gtttccccct ggaagctccc tcgtgcgctc tcctgttccg accctgccgc ttaccggata   9420
cctgtccgcc tttctccctt cgggaagcgt ggcgctttct caatgctcac gctgtaggta   9480
tctcagttcg gtgtaggtcg ttcgctccaa gctgggctgt gtgcacgaac cccccgttca   9540
gcccgaccgc tgcgccttat ccggtaacta tcgtcttgag tccaacccgg taagacacga   9600
cttatcgcca ctggcagcag ccactggtaa caggattagc agagcgaggt atgtaggcgg   9660
tgctacagag ttcttgaagt ggtggcctaa ctacggctac actagaagga cagtatttgg   9720
tatctgcgct ctgctgaagc cagttacctt cggaaaaaga gttggtagct cttgatccgg   9780
caaacaaacc accgctggta gcggtggttt ttttgtttgc aagcagcaga ttacgcgcag   9840
aaaaaaagga tctcaagaag atcctttgat cttttctacg gggtctgacg ctcagtggaa   9900
cgaaaactca cgttaaggga ttttggtcat gagattatca aaaaggatct tcacctagat   9960
ccttttaaat taaaaatgaa gttttaaatc aatctaaagt atatatgagt aaacttggtc  10020
tgacagttac caatgcttaa tcagtgaggc acctatctca gcgatctgtc tatttcgttc  10080
atccatagtt gcctgactcc ccgtcgtgta gataactacg atacgggagg gcttaccatc  10140
tggccccagt gctgcaatga taccgcgaga cccacgctca ccggctccag atttatcagc  10200
aataaaccag ccagccggaa gggccgagcg cagaagtggt cctgcaactt tatccgcctc  10260
catccagtct attaattgtt gccgggaagc tagagtaagt agttcgccag ttaatagttt  10320
gcgcaacgtt gttgccattg ctacaggcat cgtggtgtca cgctcgtcgt ttggtatggc  10380
ttcattcagc tccggttccc aacgatcaag gcgagttaca tgatccccca tgttgtgcaa  10440
aaaagcggtt agctccttcg gtcctccgat cgttgtcaga agtaagttgg ccgcagtgtt  10500
atcactcatg gttatggcag cactgcataa ttctcttact gtcatgccat ccgtaagatg  10560
cttttctgtg actggtgagt actcaaccaa gtcattctga gaatagtgta tgcggcgacc  10620
gagttgctct tgcccggcgt caatacggga taataccgcg ccacatagca gaactttaaa  10680
```

```
agtgctcatc attggaaaac gttcttcggg gcgaaaactc tcaaggatct taccgctgtt  10740

gagatccagt tcgatgtaac ccactcgtgc acccaactga tcttcagcat cttttacttt  10800

caccagcgtt tctgggtgag caaaaacagg aaggcaaaat gccgcaaaaa agggaataag  10860

ggcgacacgg aaatgttgaa tactcatact cttccttttt caatattatt gaagcattta  10920

tcagggttat tgtctcatga gcggatacat atttgaatgt atttagaaaa ataaacaaat  10980

aggggttccg cgcacatttc cccgaaaagt gccacctgac gtctaagaaa ccattattat  11040

catgacatta acctataaaa ataggcgtat cacgaggccc tttcgtctcg cgcgtttcgg  11100

tgatgacggt gaaaacctct gacacatgca gctcccggag acggtcacag cttgtctgta  11160

agcggatgcc gggagcagac aagcccgtca gggcgcgtca gcgggtgttg gcgggtgtcg  11220

gggctggctt aactatgcgg catcagagca gattgtactg agagtgcacc atatggacat  11280

attgtcgtta gaacgcggct acaattaata cataacctta tgtatcatac acatacgatt  11340

taggtgacac tata                                                    11354


<210> SEQ ID NO 3
<211> LENGTH: 27
<212> TYPE: DNA
<213> ORGANISM: Artificial Sequence
<220> FEATURE:
<223> OTHER INFORMATION: synthetic sequence

<400> SEQUENCE: 3

aacgagctca gtacggatta gaagccg                                         27


<210> SEQ ID NO 4
<211> LENGTH: 33
<212> TYPE: DNA
<213> ORGANISM: Artificial Sequence
<220> FEATURE:
<223> OTHER INFORMATION: synthetic sequence

<400> SEQUENCE: 4

ggtactagtg tttttctcc ttgacgttaa agt                                   33


<210> SEQ ID NO 5
<211> LENGTH: 36
<212> TYPE: DNA
<213> ORGANISM: Artificial Sequence
<220> FEATURE:
<223> OTHER INFORMATION: synthetic sequence

<400> SEQUENCE: 5

aacactagta ccatgagtaa aggagaagaa cttttc                               36


<210> SEQ ID NO 6
<211> LENGTH: 33
<212> TYPE: DNA
<213> ORGANISM: Artificial Sequence
<220> FEATURE:
<223> OTHER INFORMATION: synthetic sequence

<400> SEQUENCE: 6

aacactagta ccatggtgag caagggcgag gag                                  33


<210> SEQ ID NO 7
<211> LENGTH: 25
<212> TYPE: DNA
<213> ORGANISM: Artificial Sequence
<220> FEATURE:
<223> OTHER INFORMATION: synthetic sequence
```

<400> SEQUENCE: 7
atcatcgatt cgaggactgc tctgc 25

<210> SEQ ID NO 8
<211> LENGTH: 35
<212> TYPE: DNA
<213> ORGANISM: Artificial Sequence
<220> FEATURE:
<223> OTHER INFORMATION: synthetic sequence

<400> SEQUENCE: 8
tctggcgcgc cactggtgaa atagtaggga gaacg 35

<210> SEQ ID NO 9
<211> LENGTH: 40
<212> TYPE: DNA
<213> ORGANISM: Artificial Sequence
<220> FEATURE:
<223> OTHER INFORMATION: synthetic sequence

<400> SEQUENCE: 9
catggtgcta gctttaaagt atagatagaa ttgattgctg 40

<210> SEQ ID NO 10
<211> LENGTH: 45
<212> TYPE: DNA
<213> ORGANISM: Artificial Sequence
<220> FEATURE:
<223> OTHER INFORMATION: synthetic sequence

<400> SEQUENCE: 10
ctatacttta aagctagcac catgagtaaa ggagaagaac ttttc 45

<210> SEQ ID NO 11
<211> LENGTH: 45
<212> TYPE: DNA
<213> ORGANISM: Artificial Sequence
<220> FEATURE:
<223> OTHER INFORMATION: synthetic sequence

<400> SEQUENCE: 11
cttatacaac tcgtccatac cgtgtgtaat cccagcagct gttac 45

<210> SEQ ID NO 12
<211> LENGTH: 42
<212> TYPE: DNA
<213> ORGANISM: Artificial Sequence
<220> FEATURE:
<223> OTHER INFORMATION: synthetic sequence

<400> SEQUENCE: 12
ctatacttta aagctagcac catggtgagc aagggcgagg ag 42

<210> SEQ ID NO 13
<211> LENGTH: 43
<212> TYPE: DNA
<213> ORGANISM: Artificial Sequence
<220> FEATURE:
<223> OTHER INFORMATION: synthetic sequence

<400> SEQUENCE: 13
tttatataat tcatccatac catataagaa caggtggtgg cgg 43

<210> SEQ ID NO 14

<211> LENGTH: 54
<212> TYPE: DNA
<213> ORGANISM: Artificial Sequence
<220> FEATURE:
<223> OTHER INFORMATION: synthetic sequence

<400> SEQUENCE: 14
cacggtatgg acgagttgta taagggaggc ggaggcatga ctgatacatc atcc 54

<210> SEQ ID NO 15
<211> LENGTH: 57
<212> TYPE: DNA
<213> ORGANISM: Artificial Sequence
<220> FEATURE:
<223> OTHER INFORMATION: synthetic sequence

<400> SEQUENCE: 15
ttatatggta tggatgaatt atataaagga ggcggaggca tgactgatac atcatcc 57

<210> SEQ ID NO 16
<211> LENGTH: 21
<212> TYPE: DNA
<213> ORGANISM: Artificial Sequence
<220> FEATURE:
<223> OTHER INFORMATION: synthetic sequence

<400> SEQUENCE: 16
ttaggtttcc ttttcgtgtt g 21

<210> SEQ ID NO 17
<211> LENGTH: 42
<212> TYPE: DNA
<213> ORGANISM: Artificial Sequence
<220> FEATURE:
<223> OTHER INFORMATION: synthetic sequence

<400> SEQUENCE: 17
caacacgaaa aggaaaccta atgatcagcc cgctattaac gc 42

<210> SEQ ID NO 18
<211> LENGTH: 25
<212> TYPE: DNA
<213> ORGANISM: Artificial Sequence
<220> FEATURE:
<223> OTHER INFORMATION: synthetic sequence

<400> SEQUENCE: 18
atccccgggt cgaggactgc tctgc 25

<210> SEQ ID NO 19
<211> LENGTH: 78
<212> TYPE: DNA
<213> ORGANISM: Artificial Sequence
<220> FEATURE:
<223> OTHER INFORMATION: synthetic sequence

<400> SEQUENCE: 19
attgaaaaga ataagaagat aagaaagatt taattatcaa acaatatcaa tatgcgattt 60
aggtgacact atagaacg 78

<210> SEQ ID NO 20
<211> LENGTH: 87
<212> TYPE: DNA
<213> ORGANISM: Artificial Sequence
<220> FEATURE:
<223> OTHER INFORMATION: synthetic sequence

<400> SEQUENCE: 20
tgaaacagaa gatgctgaag aggatgatga agaggatgat gtatcagtca taccaccacc 60
acctttgtat agttcatcca tgccatg 87

<210> SEQ ID NO 21
<211> LENGTH: 84
<212> TYPE: DNA
<213> ORGANISM: Artificial Sequence
<220> FEATURE:
<223> OTHER INFORMATION: synthetic sequence

<400> SEQUENCE: 21
tgaaacagaa gatgctgaag aggatgatga agaggatgat gtatcagtca taccaccacc 60
acccttgtac agctcgtcca tgcc 84

<210> SEQ ID NO 22
<211> LENGTH: 36
<212> TYPE: DNA
<213> ORGANISM: Artificial Sequence
<220> FEATURE:
<223> OTHER INFORMATION: synthetic sequence

<400> SEQUENCE: 22
catggcatgg atgaactata caaaggtggt ggtggt 36

<210> SEQ ID NO 23
<211> LENGTH: 36
<212> TYPE: DNA
<213> ORGANISM: Artificial Sequence
<220> FEATURE:
<223> OTHER INFORMATION: synthetic sequence

<400> SEQUENCE: 23
cacggtatgg acgagttgta taagggaggc ggaggc 36

<210> SEQ ID NO 24
<211> LENGTH: 39
<212> TYPE: DNA
<213> ORGANISM: Artificial Sequence
<220> FEATURE:
<223> OTHER INFORMATION: synthetic sequence

<400> SEQUENCE: 24
ctgtacggca tggacgagct gtacaagggt ggtggtggt 39

<210> SEQ ID NO 25
<211> LENGTH: 39
<212> TYPE: DNA
<213> ORGANISM: Artificial Sequence
<220> FEATURE:
<223> OTHER INFORMATION: synthetic sequence

<400> SEQUENCE: 25
ttatatggta tggatgaatt atataaagga ggcggaggc 39

HIGH-THROUGHPUT SCREENING PLATFORM FOR LONGEVITY GENES AND ANTI-AGING DRUGS

STATEMENT REGARDING FEDERALLY SPONSORED RESEARCH

This invention was made with government support under grant no. R01 AG043080 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, “UCSF-559_SF-2018-055-2_Replacement_SEQ_LIST_ST25” created on Mar. 3, 2021 and having a size of 34,774 bytes. The contents of the text file are incorporated by reference herein in their entirety.

INTRODUCTION

Studies in model organisms have led to the discovery of candidate anti-aging drugs including resveratrol, rapamycin, and metformin. Given their potential impact on human health and on treating age-related diseases, it is of great importance to systematically screen for anti-aging drugs. However, this has not been possible due to the lack of high-throughput and cost-effective methods for measuring lifespan in model organisms. So far only a small number of drugs have been identified using simple model organisms (such as yeast, worms, and fly) and some of them have been tested in mammals (such as mice).

Non-vertebrate model organisms, such as *S. cerevisiae, C. elegans*, and *D. melanogaster*, have driven discovery of aging genes conserved in mammals. Most of the current candidate anti-aging drugs were discovered using a candidate approach based on the known genes. Rapamycin, for instance, targets the TOR pathway known to be involved in lifespan regulation based on genetic analysis. The lifespan extending effect of rapamycin was first reported in yeast in both chronological and replicative aging assays, and later on in worms and flies. These findings have motivated the test of rapamycin in mice, which showed lifespan extension even when fed later in life. Resveratrol is another example, which was initially discovered to activate the Sir2 gene and extend the replicative lifespan of yeast. Given that many known aging pathways are conserved across species, it is reasonable to expect that a significant fraction of the drugs that extends the lifespan of simple model organisms will have conserved effect in mice and perhaps in humans.

Budding *S. cerevisiae* is a canonical model for aging research due to its short lifespan and the ease with which it can be manipulated genetically. Yeast divides asymmetrically, with daughter cells budding off from the mother cell. Mother cells age and die after a finite number of cell divisions. This is called replicative aging, and the number of daughters produced by a mother cell is defined as the replicative lifespan of the mother cell. The traditional method for measuring lifespan is to grow yeast cells on an agar plate and manually remove daughter cells using a micro-dissector (a microscope with a needle); this way the number of daughter cells produced by a mother cell is counted. However, lifespan measurement by micro-dissection is very laborious and time-consuming. The laborintensive nature of the traditional lifespan assay makes it difficult to screen for large genetic/drug libraries, and even with more recent advances in the microfluidic arts it is not practical to use such systems for large scale screening. The present disclosure addresses the above issues and provides related advantages.

SUMMARY

The present disclosure is directed to the engineering and manufacture of microfluidic devices and compositions as components of a high-throughput platform useful in screening for and identifying anti-aging drugs and/or mutations that modulate lifespan. Specifically, herein disclosed is a yeast cell daughter-arresting-program (DAP), as well as compositions used in this platform/system, allowing the measurement of replicative lifespan (RLS) and identification of agents and/or mutations that modulate replicative lifespan.

Budding yeasts are a useful model system for identifying and studying pathways regulating lifespan that are conserved across species. Generally, under laboratory conditions, budding yeast cells divide roughly once every 90 min through a process in which smaller daughter cells pinch, or bud, off the mother cell. The “budding yeasts” (e.g., *Saccharomyces cerevisiae, Saccharomyces delbrueckii, Candida albicans, Candida glabrata, Candida parapsilosis, Candida tropicalis, Cryptococcus neoformans, Cryptococcus laurentii, Hansenula anomala, Kluyveromyces lactis, Kluyveromyces thermotolerans, Pichia anomala, Pichia pastoris* and *Yarrowia lipolytica*) are distinguished by their asymmetric budding process of cell division; the fission yeast *Schizosaccharomyces pombe*, a distant relative, is also a powerful model organism.

To date, methods for identifying and/or measuring the effects of anti-aging drugs and/or genetic mutations that affect replicative lifespan (RLS) are tedious and time consuming. The present disclosure addresses these problems by providing a high-throughput system that vastly improves time-efficiency of screening as well as cost-effectiveness. For example, the budding yeast strain, genetic construct, culture systems and microfluidic devices disclosed herein eliminate the need for microdissection of yeast daughter cells away from mother cells during cell division, thereby reducing (from years to a matter of months) the amount of time required to measure the effects of a library of drugs or mutations on RLS. The methods disclosed herein can produce, in a short period of time, many candidate anti-aging drugs for testing in other model organisms and eventually for testing in human clinical trials.

In one aspect of the present disclosure, a nucleic acid construct for integration into a specific locus of a yeast cell genome is provided, wherein the nucleic acid includes: an integration sequence at each end of the nucleic acid construct configured to effect integration into a yeast genomic locus between a sequence upstream of the start codon of an endogenous gene encoding an essential plasma membrane protein and the start codon of the gene; and two cassettes oriented in opposite transcriptional directions, including (i) a first cassette including a mother-specific promoter configured to control transcription of an exogenous copy of the gene encoding the essential plasma membrane protein; and (ii) a second cassette including a conditional promoter configured to control transcription of the endogenous gene upon integration into the yeast genomic locus. In one embodiment of the nucleic acid construct, the gene encoding the essential plasma membrane protein is PMA1.

In one aspect, a vector including said nucleic acid construct is provided. In some embodiments, the vector includes pIDS2GH (SEQ ID NO: 1) or pIDS2RH (SEQ ID NO: 2).

In one aspect, provided herein is a yeast cell including the vector.

In one aspect, also provided herein is a daughter-arresting program (DAP) yeast strain, including: an exogenous nucleic acid sequence integrated into the genome between a sequence upstream of the start codon of an endogenous gene encoding an essential plasma membrane protein and the start codon of the gene, wherein the integrated nucleic acid sequence includes: (a) a mother-specific promoter driving transcription of an exogenous copy of the gene encoding the essential plasma membrane protein; and (b) a conditional promoter driving transcription of the endogenous gene encoding the essential plasma membrane protein, wherein the mother-specific promoter and the conditional promoter are oriented in opposite transcriptional directions. In one embodiment of the DAP yeast strain, the gene encoding the essential plasma membrane protein is PMA1.

In one aspect, also provided is a method of measuring replicative lifespan (RLS), the method including: culturing one or more DAP yeast strains in a first culture medium under non-repressed conditions for the conditional promoter; culturing the one or more DAP yeast strains in a second culture medium under repressed conditions for the conditional promoter; amplifying barcode sequences of mother cells and arrested daughter cells resulting from the culturing; sequencing the amplified barcode sequences; and quantitating arrested daughter cells based on the sequencing thereby measuring RLS of the one or more DAP yeast strains. In some embodiments of the method, the one or more DAP yeast strains further include one or more genomic mutations.

In one aspect, also provided is a microfluidic device including a plurality of functional modules for measurement of yeast replicative lifespan (RLS), wherein each module includes (a) an inlet for receiving fluid flow into the module, (b) a cell-trapping and observational area, in fluid communication with the inlet, including an array of trapping units configured to trap budding mother cells and arrested daughter cells produced therefrom, and (c) an outlet, in fluid communication with the cell-trapping and observational area, for flow out of the module.

In one aspect, also provided is a kit including the DAP yeast strain and a microfluidic device including functional modules for measurement of replicative lifespan (RLS). In some embodiments, the kit further includes a multiwell plate that can be integrated with the microfluidic device, and optionally further includes a cover for the multiwell plate.

In one aspect, provided herein is a yeast cell culture device including a multiwell plate integrated with a microfluidic device positioned beneath the multiwell plate, the microfluidic device including a plurality of functional modules for measurement of RLS, wherein each module corresponds to a plurality of wells of the multiwell plate, and wherein each module includes (a) an inlet configured to provide fluid flow into the module from a first well of the multiwell plate, (b) a cell-trapping and observational area in fluid communication with the inlet and including an array of trapping units for trapping budding mother cells and arrested daughter cells produced therefrom, and (c) an outlet in fluid communication with the cell-trapping and observational area, configured to provide fluid flow out of the module to a second well of the multiwell plate. In some embodiments, the yeast cell culture device further includes a removable cover configured to mate with the multiwell plate. In some embodiments, the removable cover includes (i) a first channel in fluid communication with the inlet of each module; (ii) a second channel in fluid communication with the outlet of each module; and (iii) a vacuum-sealing channel.

In one aspect, a system is provided, the system including the microfluidic device or yeast cell culture device and a camera configured to capture images and/or video of the cell-trapping and observational area.

In one aspect, also provided is a method of determining replicative age of a yeast cell, including (a) culturing one or more DAP yeast strains in a first culture medium under non-repressed conditions for the conditional promoter; (b) culturing the one or more DAP yeast strains from step (a) in a second culture medium under repressed conditions for the conditional promoter; and (c) counting arrested daughter cells produced by the one or more DAP yeast strains to determine replicative age of one or more mother cells of the DAP yeast strain. In some embodiments, the method includes contacting one or more of the one or more DAP yeast strains with a test compound and determining the effect of the test compound on replicative age of the one or more DAP yeast strains contacted with the compound. In some embodiments, one or both of steps (a) and (b) are performed in the microfluidic device or yeast cell culture device (or using the system), and the daughter cells produced by the one or more DAP yeast strains and trapped in the cell-trapping and observational area are counted to determine replicative age.

In one aspect, also provided is a method of determining replicative age of one or more yeast cells, including: culturing one or more DAP yeast strains in a first culture medium under non-repressed conditions for the conditional promoter; flowing the one or more DAP yeast strains into the plurality of functional modules of the microfluidic device or yeast cell culture device above, through the inlets; entrapping the one or more DAP yeast strains in the arrays of trapping units in the cell-trapping and observational areas; culturing the entrapped DAP yeast strains in a second culture medium under repressed conditions for the conditional promoter such that a population of non-dividing daughter cells is produced and entrapped within the array of trapping units in proximity to corresponding mother cells of the DAP yeast strain; and quantifying/quantitating or counting arrested daughter cells produced by the one or more DAP yeast strains to determine replicative age of one or more mother cells of the DAP yeast strain. In some embodiments, the method includes imaging the budding mother and arrested daughter cells of the one or more DAP yeast strains prior to quantifying or counting.

In one aspect, also provided is a method of screening and identifying compounds that modulate replicative lifespan (RLS), including (a) culturing one or more DAP yeast strains in a first culture medium under non-repressed conditions for the conditional promoter; (b) switching the one or more DAP yeast strains to a second culture medium under repressed conditions for the conditional promoter, and for each of the one or more DAP yeast strains under repressed conditions, treating with one or more test compounds; (c) counting or quantifying arrested daughter yeast cells to determine replicative age; and (d) identifying test compounds that modulate RLS as compared to an untreated control. In some embodiments, the method further includes, after the DAP strains are in the second culture medium under repressed conditions, applying each of the strains to a microfluidic device or yeast cell culture device, and imaging arrested daughter yeast cells in the cell-trapping and observational area. In some embodiments, the method further includes, before step (a), barcoding the strains to produce unique strains with individual barcodes. In some embodiments, the method further includes sequencing and quantifying cells having individual barcodes.

In one aspect, also provided herein is a method of screening and identifying mutant yeast strains having an altered/enhanced replicative lifespan (RLS), including (a) culturing a library of mutant DAP strains in a first culture medium in one or more multiwell plates under non-repressed conditions for the conditional promoter, where the mutant DAP strains are DAP strains, which further include one or more genomic mutations; (b) switching the library of mutant DAP strains to a second culture medium under repressed (daughter-arrested) conditions for the conditional promoter; (c) applying each member of the library of mutant DAP strains under repressed (daughter-arrested) conditions to a microfluidic device or yeast cell culture device; (d) counting or quantifying arrested daughter yeast cells to determine RLS; and (e) identifying mutant DAP strains having an altered/enhanced RLS as compared to an unmutated DAP strain control. In some embodiments, each member in the library of mutant DAP strains being screened resides in a well of one or more multiwell plates.

In one aspect, also provided herein is a method of screening and identifying mutant yeast strains having an altered/enhanced replicative lifespan (RLS), including (a) culturing a pooled library of mutant DAP strains in a starting liquid culture under non-repressed conditions for the conditional promoter, wherein the mutant DAP strains are DAP strains which further include one or more genomic mutations and a nucleic acid barcode sequence; (b) switching the pooled library of mutant DAP strains to a second culture medium under repressed, daughter-arrested conditions for the conditional promoter; (c) aliquoting the starting liquid culture into two or more liquid cultures with equal volume, where each aliquot is allowed to grow for a different length of time ($t_i$, where i=0, . . . N−1), at which time a fixed amount of external reference cells having distinguishing barcodes is added, cells are harvested, DNA extracted and barcodes PCR-amplified with an ith index sequence added; and (c) pooling together all N sequence samples and performing next generation sequencing to identify mutant yeast strains having an altered/enhanced replicative lifespan (RLS).

In one aspect, also provided herein is a method of screening and identifying compounds that modulate replicative lifespan (RLS), including (a) culturing, under non-repressed conditions, a library of wildtype barcoded DAP strains in one or more multiwell plates, each well containing one member of the library with a unique barcode; (b) at time $t_0$, transferring and culturing each member of the library to an equivalent well in one or more duplicate multiwell plates under repressed, daughter-arrested conditions, where each duplicate plate is allowed to grow for a different length of time ($t_i$, where i=0, . . . N−1), and adding a test compound; (c) pooling cultures of the ith duplicate for each timepoint i, and adding a fixed amount of external reference cells having distinguishing barcodes; and (d) harvesting, extracting and PCR-amplifying barcodes with an ith index sequence added; and (e) performing next generation sequencing to identify compounds that modulate RLS.

In one aspect, also provided herein is a method of simultaneously measuring the effects on replicative lifespan of $10^2$-$10^3$ mutations and/or compounds/candidate drugs by quantifying barcoded DAP yeast strain daughter cells in liquid culture using next generation sequencing.

BRIEF DESCRIPTION OF THE DRAWINGS

FIGS. 3D-3F are DAmP alleles having reduced expression of essential genes PGI1 (3D), GPI5 (FIG. 3E) and THS1 (FIG. 3F).

FIG. 6 depicts a schematic for identifying drug compounds that delay aging/extend RLS, using barcoded DAP strains and NGS according to an embodiment of the present disclosure.

BRIEF DESCRIPTION OF THE SEQUENCES

Figure 1A:
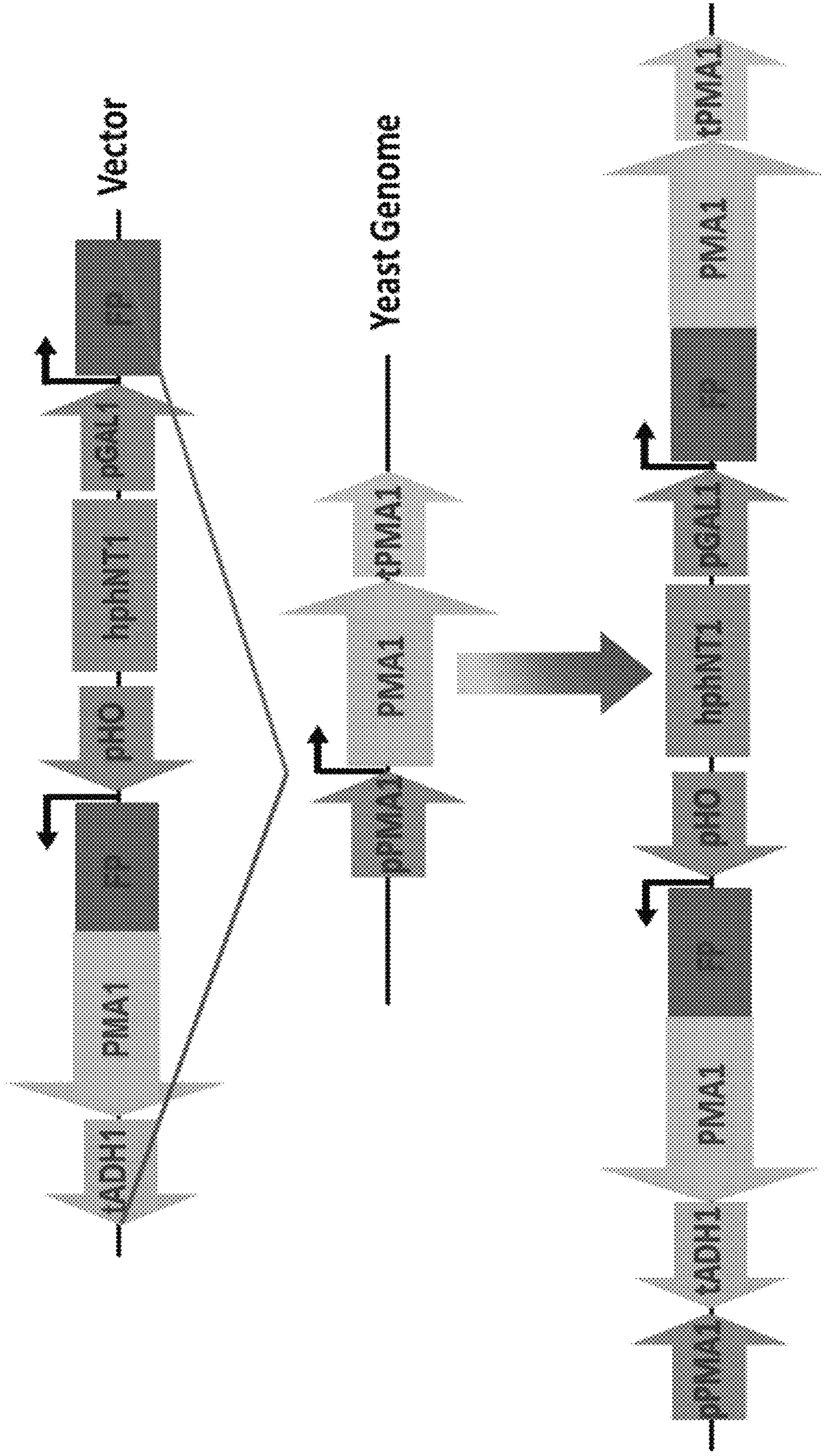
FIG. 1A depicts a Daughter-Arresting Program (DAP) vector according to an embodiment of the present disclosure and its integration into the budding yeast genome.

SEQ ID NO: 1 sets forth the nucleic acid sequence of plasmid pIDS2GH.

SEQ ID NO: 2 sets forth the nucleic acid sequence of plasmid pIDS2RH.

DEFINITIONS

By "yeast cell daughter-arresting-program (DAP)" is meant a system that includes a budding yeast strain that has been engineered to conditionally express a plasma membrane component (e.g., wherein a conditional promoter is integrated into the yeast genome to conditionally express the plasma membrane protein), allowing for regulatable arrest of division in daughter cells.

By "budding yeast" is meant a unicellular yeast that divides by asymmetric budding (e.g., *Saccharomyces cerevisiae, Saccharomyces delbrueckii, Candida albicans, Candida glabrata, Candida parapsilosis, Candida tropicalis, Cryptococcus neoformans, Cryptococcus laurentii, Hansenula anomala, Kluyveromyces lactis, Kluyveromyces thermotolerans, Pichia anomala, Pichia pastoris* and *Yarrowia lipolytica*, etc.).

As used herein, the phrase "fluid flow" refers to the flow of a liquid (e.g., water, media, or a solution used for washing), or to the flow of air through the microfluidic device, multiwell plate and/or the optional cover as described herein.

As used herein, the phrase "in fluid communication", "fluidically connected", and the like with respect to two or more structures refers to a configuration that allows for fluid flow between or through the structures (depending on context), but does not require that fluid be present. Thus, for example, "a cell-trapping and observational area in fluid communication with an inlet" refers to a configuration that allows for fluid flow between the cell-trapping and observational area and the inlet when fluid is present, but does not require that the fluid be present.

The phrase "mother-specific promoter" refers to a promoter region of a gene that is specifically expressed in the mother cell, but not in the daughter cells that arise from budding of the mother cell. For example, the HO endonuclease induces mating-type switching in *S. cerevisiae* by creating a double-stranded break at the MAT locus. The HO gene is only transcribed in "mother" cells, i.e., cells that have previously budded and given birth to a "daughter" cell. In mother cells, HO is transcribed transiently during the cell cycle, shortly before budding and DNA replication.

The phrase "conditional promoter" or "conditional gene expression system" refers to a transcriptional regulatory system and/or nucleic acid sequence by which transcription is activated under certain conditions and repressed under others. Examples of conditional promoters and/or conditional gene expression systems that may be used in budding yeasts are GAL1, PCK1 (Leuker, et al., 1997, *Gene* 192: 235-240), MAL2 (Geber, et al., 1992, *J. Bacteriol.* 174: 6992-6996), MET3 (Care, et al., 1999, *Mol. Microbiol.* 34:792-798), a tetracycline-regulatable system based on the repressor/operator elements of an *Escherichia coli* tetracycline resistance operon (Nakayama, H. et al., 2000, *Infect. Immun.* 68:6712-6719), the Cre-Lox recombination system (Nagy, et al., 2000, *Genesis* 26 (2): 99-109), the Flp-FRT recombination system (Schlake, et al., 1994, *Biochemistry.* 33 (43): 12746-1275), a chimeric system, called LexA-ER-AD, employing the bacterial LexA DNA-binding protein, the human estrogen receptor (ER) and an activation domain (AD), tightly regulated by the hormone β-estradiol (Ottoz, et al., 2014, *Nucl. Acids Res.* 42 (17): e130), and temperature-sensitive promoters such as HSF1 and MET17. A list of promoters used in yeast is available online at //parts.i-gem.org/Promoters/Catalog/Yeast/Positive. In some cases, such as when the Cre and FRT recombinase systems are used, activation or knockout of the gene upon recombination is irreversible, whereas in Tet and ER systems, activation or repression of gene expression is reversible.

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "nucleic acid barcode sequence", "nucleic acid barcode", "barcode", and the like as used herein refer to a nucleic acid having a sequence which can be used to identify and/or distinguish one or more first molecules to which the nucleic acid barcode is conjugated from one or more second molecules. Nucleic acid barcode sequences are typically short, e.g., about 5 to 20 bases in length, and may be conjugated to one or more target molecules of interest or amplification products thereof. Nucleic acid barcode sequences may be single or double stranded.

The terms "polypeptide," "peptide," and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A "vector" is capable of transferring gene sequences to target cells. Typically, "vector construct," "expression vector," and "gene transfer vector," mean any nucleic acid construct capable of directing the expression of a gene of interest in a host cell. Thus, the term includes cloning, and expression vehicles, as well as integrating vectors.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a mutant" includes a plurality of such mutants, and reference to "the drugs" includes reference to one or more drugs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed. For all purposes in the United States and in other jurisdictions where effective, each and every publication and patent document cited in this disclosure is hereby incorporated herein by reference in its entirety for all purposes to the same extent as if each such publication or document was specifically and individually indicated to be incorporated herein by reference.

Definitions of other terms and concepts appear throughout the detailed description below.

DETAILED DESCRIPTION

Genetic studies of aging in model organisms have verified that at least some pathways regulating senescence/aging and lifespan are conserved across species. Several promising potential anti-aging drugs have been developed based on the genetic information. However, progress in the field has been hampered by the lack of high throughput, cost effective methods to measure the lifespan of any model organism. Herein disclosed is a high throughput system for measuring the replicative lifespan of yeast, a canonical model organism for aging studies. The system described herein combines a genetic construct and a budding yeast strain, and in some cases, a microfluidic device. The system makes it possible to measure the lifespan of yeast mother cells for thousands of cells, strains, mutants or drug treatments in parallel, without the need for time-lapse microscopy and/or having to remove and/or count the daughter cells using a micromanipulator. The power of the system was demonstrated by testing known mutants and drugs that extend lifespan, and by screening for novel lifespan extending mutants. The present system significantly enhances the ability to explore the genetic landscape and small molecule drug space for therapeutic interventions that may slow/reverse aging and cure age-related disease.

The budding yeast, *Saccharomyces cerevisiae*, is a well-established model system in aging research. Chronological lifespan (CLS) is defined as the length of time a non-dividing yeast cell survives; replicative lifespan (RLS) is defined as the number of times an individual mother cell divides into daughter cells before senescence and death. In the search for mutations and/or compounds that counteract early aging and cancer, the standard method requires tedious and time consuming separation of daughter cells away from mother cells every few hours, using microdissection.

Typically, single yeast cells have been used to study replicative aging; however, this is not a practical approach for large scale screening of mutants or compounds that influence RLS (Zhang, et al., 2012, *PLoS ONE* 7 (11): e48275; Xie, et al., 2012, *PLoS ONE* 11 (4): 599-606).

Provided herein is a novel, high-throughput system for measuring yeast replicative lifespan, useful for screening mutations and drugs that influence RLS. Also provided are novel nucleic acid constructs for conditional/regulatable arrest of the budding process in daughter cells, while leaving the mother cells unaffected. In some cases, a microfluidic device is used to allow counting of daughter cells held in an observation area. As an alternative to using the microfluidic device, the presently disclosed daughter-arresting-program (DAP), when combined with strain barcoding and next generation sequencing, makes it possible to simultaneously measure the lifespan of thousands of strains and/or drug treatments by cell counting in liquid culture.

As a non-limiting example, in some instances, a library of yeast mutants may be crossed with a yeast DAP strain to obtain a library of yeast mutant DAP strains, and the obtained library of yeast mutant DAP strains may be assessed for effects of each mutation on replicative lifespan. In some embodiments, a library of compounds may be tested for their effects on replicative lifespan using the DAP system.

Herein disclosed is a new system/platform that allows high throughput measurement of yeast replicative lifespan. This technology combines novel genetic engineering with microfluidic device engineering. Herein disclosed are: 1) a novel genetic program which, upon media switch, arrests daughter cell division while leaving the mother cell division unaffected, making it possible to measure the lifespan of a mother cell by counting the number of arrested daughter cells surrounding the mother cell after the mother cell has died. This circumvents the need to remove daughter cells and to perform time-lapse imaging; 2) a novel microfluidic device that interfaces with a multiwell plate (e.g., a 48-, 96-, or 384-well plate). In the case of a 96-well plate, for example, the device contains 32 independent modules (each independent module is superimposable onto three wells), where each module is used to analyze a different mutant strain or drug treatment. For each of the "functional modules," there is an observational area that can be viewed under a microscope objective, with regularly spaced trapping units, also referred to herein as microstructures, that can trap single DAP mother cells. The disclosed system may be readily automated, e.g., using commercially available liquid handling robots, to do high throughput imaging, and to screen tens of thousands of members of a library (e.g., libraries of mutations or possible therapeutic agents) for their ability to influence RLS. Even without automation, combining the genetically engineered strain and the new device, one person can analyze ~130 strains/drugs per day using a microscope; this throughput is ~100 fold higher than that based on the non-engineered strain and previous microfluidic devices, and ~500 fold higher than that of the traditional microdissection method.

The DAP system has several advantages over the mother enrichment program (MEP) (Lindstrom and Gottschling, 2009, Genetics, 183:413-422). These include: 1) ease of use—it is straightforward to construct a library of strains with DAP because the DAP uses a single construct integrated to a genomic locus, whereas the MEP uses three different constructs integrated to different genomic loci.; and 2) the DAP system leads to clean arrest of daughter cells, while the MEP suffers from the daughter cell leakage problem. The clean arrest of daughter cells is important for developing a high-throughput approach for lifespan measurements based on cell counting. By switching off the expression of an essential gene whose protein product localizes to the plasma membrane, the presently disclosed construct provides daughter cells devoid of the protein once synthesis is switched off, because daughter cells do not inherit cell membrane from their mothers. In contrast, MEP uses a daughter specific promoter to drive a recombinase, which relocates to the nucleus upon induction by estradiol to cut out two essential genes from genomic DNA in the daughter cells. Because daughter cells still inherit these essential proteins from their mothers, they may continue dividing for several generations.

The DAP system also has key advantages over the "death of daughter" strain described in Jarolim et al., 2004, *FEMS Yeast Res.* 5:169-177, which is leaky and the mother cells are very short-lived (~5 generations). The "death of daughter" strain uses genetic constructs that drive an essential cell cycle gene Cdc6 by a mother specific promoter (HO) and a glucose repressible promoter. Upon switching to glucose, only the mother specific promoter produces Cdc6. Without intending to be bound by any particular theory, the short lifespan of the mother cell may be due to the insufficient expression of Cdc6. Unlike the long-lived Pma1 protein expressed in embodiments of the DAP system, Cdc6 is short lived and subject to cell cycle dependent regulation. Again, without intending to be bound by any particular theory, the leakage in the "death of daughter" system may be due to partitioning of Cdc6 protein (localized in cytosol) into the daughter cell from the mother.

Nucleic Acid Constructs

As discussed above, the present disclosure provides a yeast cell daughter-arresting-program (DAP), which enables the measurement of replicative lifespan (RLS) and identification of agents and/or mutations that modulate replicative lifespan. Nucleic acids constructs which may be used to generate the disclosed DAP yeast strain are described in greater detail below.

In one aspect of the present disclosure, a nucleic acid construct for integration into a specific locus of a yeast cell genome is provided, wherein the construct includes: an integration sequence at each end of the nucleic acid construct configured to effect integration into a yeast genomic locus between a sequence upstream of the start codon of an endogenous gene encoding an essential plasma membrane protein and the start codon of the gene; and two cassettes oriented in opposite transcriptional directions, including (i) a first cassette including a mother-specific promoter configured to control transcription of an exogenous copy of the gene encoding the essential plasma membrane protein; and (ii) a second cassette including a conditional promoter configured to control transcription of the endogenous gene upon integration into the yeast genomic locus.

In some embodiments of the nucleic acid construct, the construct is configured such that, upon integration into the yeast genomic locus between the sequence upstream of the start codon of the gene encoding the essential plasma membrane protein and the start codon of the gene, the first cassette drives transcription, via the mother-specific promoter, of the integrated exogenous copy of the gene encoding the essential plasma membrane protein; and the second cassette drives transcription, via the conditional promoter, of the endogenous gene encoding an essential plasma membrane protein. In some embodiments, the nucleic acid construct further includes a first reporter marker transcriptionally linked in-frame to the exogenous copy of the gene encoding the essential plasma membrane protein. In some embodiments, the nucleic acid construct includes a second reporter marker operably linked to the conditional promoter, such that upon integration into the yeast genomic locus between the sequence upstream of the start codon of the gene encoding the essential plasma membrane protein and the start codon of the gene, the second reporter marker is transcriptionally linked in-frame to the endogenous gene encoding an essential plasma membrane protein. In some embodiments of the nucleic acid construct, the first and/or second reporter marker is a fluorescent reporter. In some embodiments of the nucleic acid construct, the fluorescent reporter is GFP or dTomato, although any other suitable reporter, which does not interfere with the functioning of the DAP strain may be utilized. In some embodiments, the nucleic acid construct further includes one or more selectable markers. In some embodiments of the nucleic acid construct, the one or more selectable markers is selected from aphA1, ble, Cat, CmR, CYH2, nat, kan, pat, AUR1-C and hphNT1. In some embodiments, the selectable marker is hphNT1. In some embodiments of the nucleic acid construct, the gene encoding the essential plasma membrane protein is selected from the group consisting of ALR1, ARP3, AVO1, BNI1, CDC19, CDC42, COF1, CTR1, CYR1, EFR3, ERG25, EXO70, FCY21, GPA1, GUP1, HIP1, HKR1, HRR25, KOG1, LST8, MSC1, MSS4, PAN1, PFY1, PGA3, PGI1, PGK1, PHO90, PKC1, PMA1, PTR3, RHO1, RHO3, RSP5, SEC1, SEC4, SEC9, SSY1, SSY5, STT4, TCP1, TOR2, TPI1, UGP1 and YPP1. In some embodiments of the nucleic acid construct, the gene encoding the essential plasma membrane protein is PMA1. In some embodiments of the nucleic acid construct, the conditional promoter is a temperature-sensitive promoter selected from HSF1 and MET17, a glucose-repressible promoter selected from pGAL1, PCK1 and MAL2, a methionine- and/or cysteine-repressible promoter MET3, or other conditional gene expression system selected from a tetracycline-regulatable system, the Cre-Lox recombination system, the Flp-FRT recombination system and the LexA-ER-AD system. In some embodiments of the nucleic acid construct, the conditional promoter is pGAL1. In some embodiments of the nucleic acid construct, the mother-specific promoter is selected from pHO, HO-TX, TXC and TXC2. In some embodiments of the nucleic acid construct, the mother-specific promoter is pHO.

In one aspect, a vector including said nucleic acid construct is provided. In some embodiments, the vector includes pIDS2GH (SEQ ID NO: 1) or pIDS2RH (SEQ ID NO: 2).

In one aspect, provided herein is a yeast cell including the vector.

DAP Yeast Strains

The nucleic acid constructs and vectors described herein may be used to generate the DAP yeast strains described herein. In one aspect, provided herein is a daughter-arresting program (DAP) yeast strain, including: an exogenous nucleic acid sequence integrated into the genome between a sequence upstream of the start codon of an endogenous gene encoding an essential plasma membrane protein and the start codon of the gene, wherein the integrated nucleic acid sequence includes: (a) a mother-specific promoter driving transcription of an exogenous copy of the gene encoding the essential plasma membrane protein; and (b) a conditional promoter driving transcription of the endogenous gene encoding the essential plasma membrane protein, wherein the mother-specific promoter and the conditional promoter are oriented in opposite transcriptional directions. In some embodiments of the DAP yeast strain, the integrated nucleic acid sequence further includes a first reporter marker transcriptionally linked in-frame to the exogenous copy of the gene encoding the essential plasma membrane protein. In some embodiments of the DAP yeast strain, the integrated nucleic acid sequence further includes a second reporter marker transcriptionally linked in-frame to the endogenous gene encoding an essential plasma membrane protein. In some embodiments of the DAP yeast strain, the first and/or second reporter marker is a fluorescent reporter. In some embodiments of the DAP yeast strain, the fluorescent reporter is GFP or dTomato. In some embodiments of the DAP yeast strain, the integrated nucleic acid sequence further includes one or more selectable markers. In some embodiments of the DAP yeast strain, the one or more selectable markers is selected from aphA1, ble, Cat, CmR, CYH2, nat, kan, pat, AUR1-C and hphNT1. In some embodiments of the DAP yeast strain, the selectable marker is hphNT1. In some embodiments of the DAP yeast strain, the gene encoding the essential plasma membrane protein is selected from the group consisting of ALR1, ARP3, AVO1, BNI1, CDC19, CDC42, COF1, CTR1, CYR1, EFR3, ERG25, EXO70, FCY21, GPA1, GUP1, HIP1, HKR1, HRR25, KOG1, LST8, MSC1, MSS4, PAN1, PFY1, PGA3, PGI1, PGK1, PHO90, PKC1, PMA1, PTR3, RHO1, RHO3, RSP5, SEC1, SEC4, SEC9, SSY1, SSY5, STT4, TCP1, TOR2, TPI1, UGP1 and YPP1. In some embodiments of the DAP yeast strain, the gene encoding the essential plasma membrane protein is PMA1. In some embodiments of the DAP yeast strain, the conditional promoter is a temperature-sensitive promoter selected from HSF1 and MET17, a glucose-repressible promoter selected from pGAL1, PCK1 and MAL2, a methionine- and/or cysteine-repressible promoter MET3, or other conditional gene expression system selected from a tetracycline-regulatable system, the Cre-Lox recombination system, the Flp-FRT recombination system and the LexA-ER-AD system. In some embodiments of the DAP yeast strain, the conditional promoter is pGAL1. In some embodiments of the DAP yeast strain, the mother-specific promoter is selected from pHO, HO-TX, TXC and TXC2. See, for example, Pothoulakis G, Ellis T (2018) Construction of hybrid regulated mother-specific yeast promoters for inducible differential gene expression. *PLoS ONE* 13(3): e0194588.

In some embodiments of the DAP yeast strain, the mother-specific promoter is pHO. In some embodiments, the DAP yeast strain further includes an exogenous nucleic acid barcode sequence.

An exemplary vector and genomic integration scheme for producing a DAP yeast strain as described herein is illustrated schematically in FIG. 1A, wherein pPMA1: promoter of gene PMA1; tADH1: terminator of *Ashbya gossypii* gene ADH1; FP: Fluorescence Protein (dTomato, GFP, etc.); pHO: promoter of mother specific gene HO; hphNT1: cassette of selection marker Hygromycin; pGAL1: yeast GAL1 promoter; tPMA1: terminator of gene PMA1.

Microfluidic Devices, Yeast Cell Culture Devices, and Systems

The present disclosure provides microfluidic devices and yeast cell culture devices, which can be used as components of a high-throughput platform for screening and identifying anti-aging drugs and/or mutations that modulate lifespan in combination with a DAP yeast strain as described herein. Devices and systems are now described in greater detail with reference to FIGS. 8A-18. In one aspect, the present disclosure provides a microfluidic device 102 including a plurality of functional modules 104 for measurement of yeast replicative lifespan (RLS), wherein each module 104 includes (a) an inlet 106 for receiving fluid flow into the module 104, (b) a cell-trapping and observational area 108, in fluid communication with the inlet 106, including an array of trapping units 109 configured to trap budding mother cells and arrested daughter cells produced therefrom, and (c) an outlet 107, in fluid communication with the cell-trapping and observational area 108, for flow out of the module 104.

Also provided is a kit including the DAP yeast strain and a microfluidic device including functional modules for measurement of replicative lifespan (RLS). In some embodiments, the kit further includes a multiwell plate that can be integrated with the microfluidic device, and optionally further includes a cover for the multiwell plate.

In one aspect, provided herein is a yeast cell culture device 100 including a multiwell plate 101 integrated with a microfluidic device 102 positioned beneath the multiwell plate (See FIGS. 8A-8C, 9, and 19), the microfluidic device 102 including a plurality of functional modules 104 for measurement of RLS, wherein each module 104 corresponds to a plurality of wells 105 of the multiwell plate 101, and wherein each module 104 includes (a) an inlet 106 configured to provide fluid flow into the module 104 from a first well 105A of the multiwell plate 101, (b) a cell-trapping and observational area 108 in fluid communication with the inlet 106 and including an array of trapping units 109 for trapping budding mother cells and arrested daughter cells produced therefrom, and (c) an outlet 107 in fluid communication with the cell-trapping and observational area 108, configured to provide fluid flow out of the module 104 to a second well 105B of the multiwell plate 101. In some embodiments, the yeast cell culture device 100 further includes a removable cover 200 configured to mate with the multiwell plate 101. In some embodiments, the removable cover 200 includes (i) a first channel 201 in fluid communication with the inlet 106 of each module 104; (ii) a second channel 202 in fluid communication with the outlet 107 of each module 104; and (iii) a vacuum-sealing channel 203. The removable cover 200 may include a loading hole 204 in fluid communication with first channel 201, a vent hole 205 in fluid communication with the second channel 202, and a vacuum hole 206.

In some embodiments of the yeast cell culture device 100, the cell-trapping and observational area 108 is positioned beneath a third well 105C of the multiwell plate 101. In some embodiments of the yeast cell culture device 100, the third well 105C of the multiwell plate 101 is positioned between the first 105A and second 105B wells. In some embodiments of the yeast cell culture device 100, each module 104 spans the length of three wells (e.g., 105A, 105B and 105C) of the multiwell plate 101. In some embodiments of the yeast cell culture device 100, the multiwell plate has 48, 96 or 384 wells. While a 96 well plate is shown in the figures, this is for illustration purposes only and is not intended to be limiting. In some embodiments of the yeast cell culture device, the multiwell plate has 48 wells and the plurality of functional modules is 16 modules. In some embodiments of the yeast cell culture device, the multiwell plate has 96 wells and the plurality of functional modules is 32 modules. In some embodiments of the yeast cell culture device, the multiwell plate has 384 wells and the plurality of functional modules is 128 modules.

Figure 11:
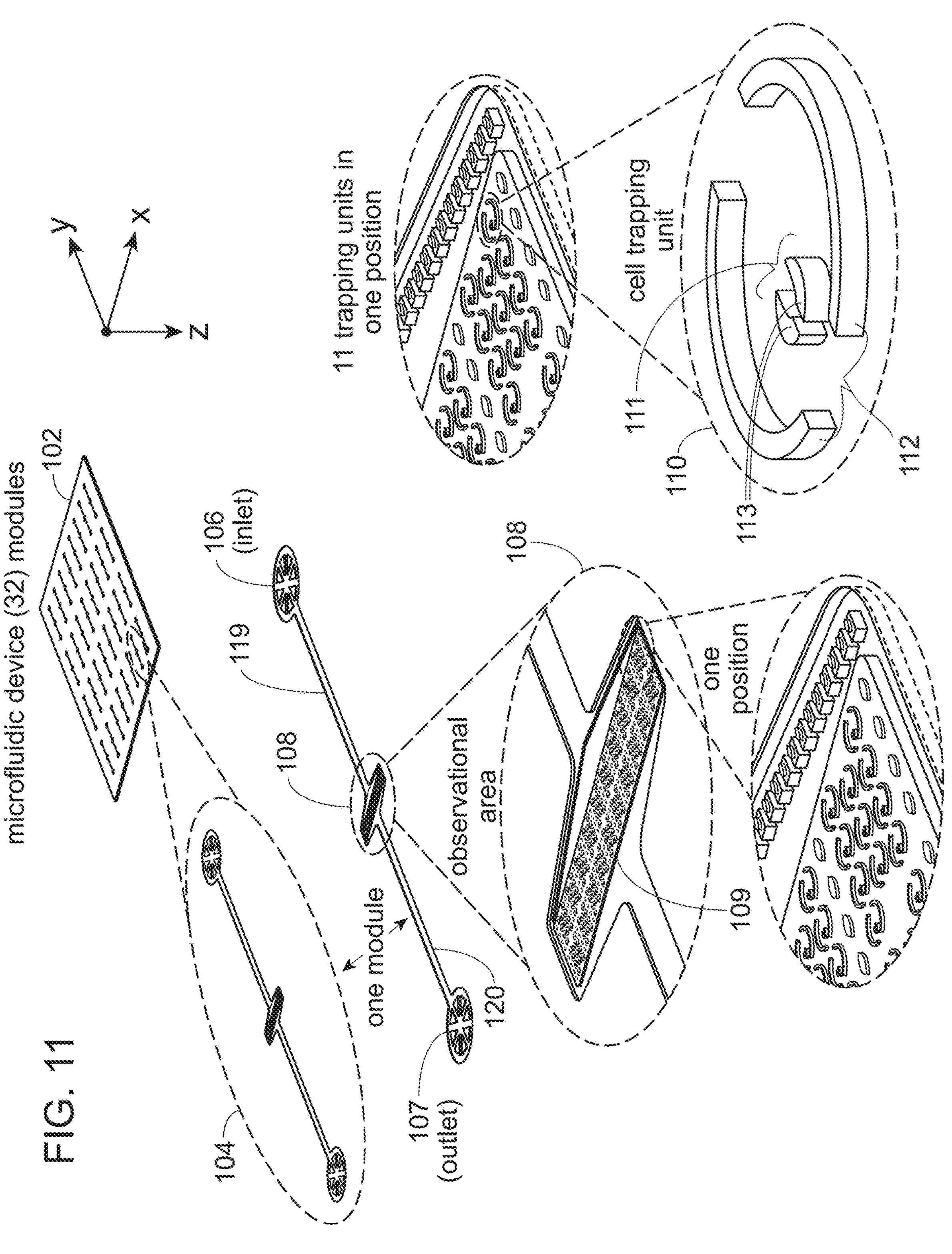
FIG. 11: depicts a microfluidic device corresponding to a 96-well plate having 32 modules, the observational area within one module, one position (of 20 positions per observational area) having eleven trapping units in each position according to an embodiment of the present disclosure.
Figure 13:
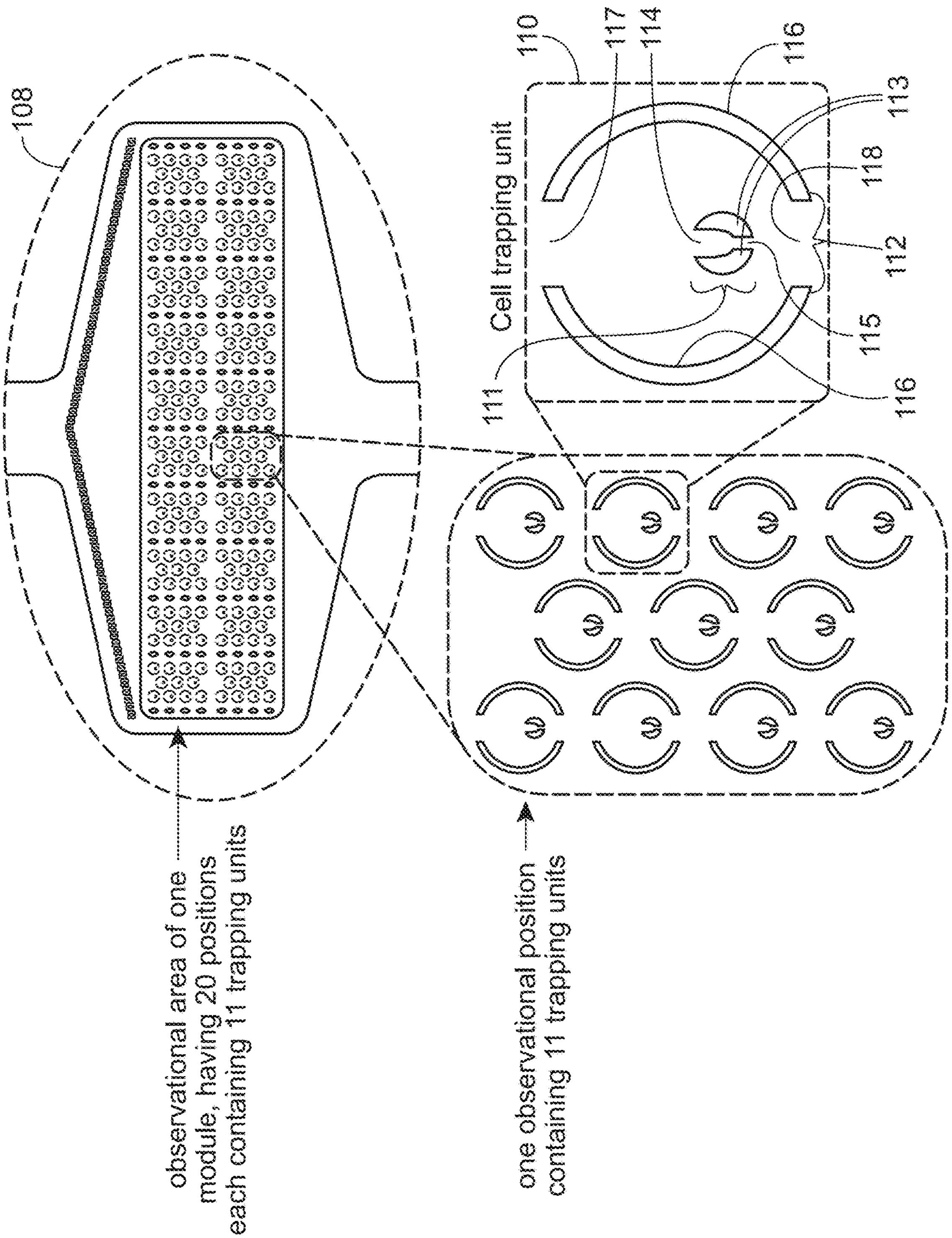
FIG. 13: depicts an observational area within one module, and one observational position having eleven cell trapping units according to an embodiment of the present disclosure.

In some embodiments of the microfluidic device 102 or the yeast cell culture device 100, the array of trapping units 109 includes: a plurality of trapping units 110, each unit 110 comprising a budding-mother cell trapping structure 111, sized and shaped to trap a budding mother cell and allow fluid flow-through prior to trapping a budding mother cell; and an arrested-daughter cell trapping structure 112 associated with each budding-mother cell trapping structure, wherein the arrested-daughter cell trapping structure 112 is configured to allow fluid flow-through and trap the budding-mother and arrested-daughter cells produced as a result of budding of the trapped mother cell. In some embodiments of the microfluidic device 102 or the yeast cell culture device 100, the arrested-daughter cell trapping structure 112 encompasses the budding-mother cell trapping structure 111. In some embodiments of the microfluidic device or the yeast cell culture device, the budding-mother cell trapping structure 111 includes a pair of walls 113 positioned and angled to define a first opening 114 between the two walls 113 and a second opening 115 between the two walls 113, wherein the first opening 114 is positioned to receive a fluid flow and is wider than the average diameter of a budding-mother cell to be trapped, and wherein the second opening 115 is narrower than the average diameter of a budding-mother cell to be trapped. In some embodiments of the microfluidic device 102 or the yeast cell culture device 100, the walls are arcuate, e.g., as shown in FIGS. 11 and 13. In some embodiments of the microfluidic device 102 or the yeast cell culture device 100, the length of the first opening 114 is at least 2 times the length of the second opening 115. In some embodiments of the microfluidic device 102 or the yeast cell culture device 100, the length of the first opening 114 is from about 4.0 μm to about 5 μm and the width of the second opening 115 is from about 1.5 μm to 2.5 μm. In some embodiments of the microfluidic device 102 or the yeast cell culture device 100, the length of the first opening 114 is about 4.5 μm and the width of the second opening 115 is about 2 μm.

In some embodiments of the microfluidic device 102 or the yeast cell culture device 100, the daughter cell trapping structure 112 includes a pair of walls 116 positioned to define a first opening 117 between the two walls and a second opening 118 between the two walls, wherein the first opening 117 is positioned to receive a fluid flow and the second opening 118 is positioned to allow exit of the fluid flow. In some embodiments of the microfluidic device 102 or the yeast cell culture device 100, the walls 116 of the daughter cell trapping structure are arcuate, e.g., as shown in FIGS. 11 and 13, providing a substantially circular trapping structure 112 defining open gates on two sides. In some embodiments of the microfluidic device 102 or the yeast cell culture device 100, the length of the first 117 and/or the second 118 opening of the daughter cell trapping structure 112 is from about 10 μm to about 20 μm. In some embodiments of the microfluidic device 102 or the yeast cell culture device 100, the length of the first 117 and/or the second 118 opening of the daughter cell trapping structure 112 is about 14 μm. In some embodiments, the microfluidic device 102 or the yeast cell culture device 100 further includes a removable cover 200 configured to mate with the multiwell plate 101.

In embodiments of the present disclosure, a yeast cell culture device, e.g., a yeast cell culture device 100, including a multiwall plate, e.g., a multiwall plate 101, integrated with a microfluidic device, e.g., a microfluidic device 102, including an array of modules, e.g., modules 104 is provided. In one embodiment, each module encompasses the equivalent of three wells on the multiwell plate, and has an inlet and an outlet flanking (and in fluid communication with) an observational area aligned with the middle well of each 3-well-sized module. The observational area in between the inlet and outlet of each module allows a microscope objective to view the cell-trapping units within the middle wells of several modules at a time). This design combines the advantages of using 1) a standard multiwell plate which can be automated for liquid/cell culture handling, with 2) a microfluidic device's ability to trap daughter-arrested mother cells within trapping units/microstructures, and 3) long term time-lapse imaging through the observational area. Because of the modular design, each module (including the inlet, observational area and outlet) and the components (e.g., the multiwell plate, microfluidic device, observational area and an optional cover) can be changed to optimize the modules for specific tasks.

In general, cells or strains (either wild type or mutant libraries) are cultured in one or more multiwell plate(s), e.g., a multiwall plate 101. For testing, screening and identifying compounds effective in modulating replicative lifespan (RLS), a library of compounds may also be stored in one or more multiwell plates, e.g., multiwall plates 101. A multichannel pipette or liquid handling robot can be used to transfer or load cells or compounds and/or media (with or without drug compounds to be tested) into a device described herein.

After loading cells or strains into the multiwell plate(s), the cover can be put into place and used to apply compressed air to push the cells to flow through channels and through modules in the device, allowing DAP mother cells to be trapped in the trapping units in the modules of the microfluidic device. The cover is then removed and the remaining water discarded, and appropriate media is added. The cover and compressed air can be used to wash cells, such that pressure causes air or other fluid (e.g., media) to flow through the modules. A microscope may be employed to view the observational area of the microfluidic device. After washing cells, the appropriate media is then added to the device (for example, for each module, corresponding to the wells of a multiwell plate which can be integrated into the device, two wells flank each middle well of a 3-well module, and these flanking wells have inlet-side and outlet-side channels for fluid to flow into and out of the module).

After incubating, image software can be used to automatically take images. Software may be used to automatically gather and analyze data, and to calculate the life span results after the images are uploaded to a server or other (digital or analog) storage medium.

Figure 2A:
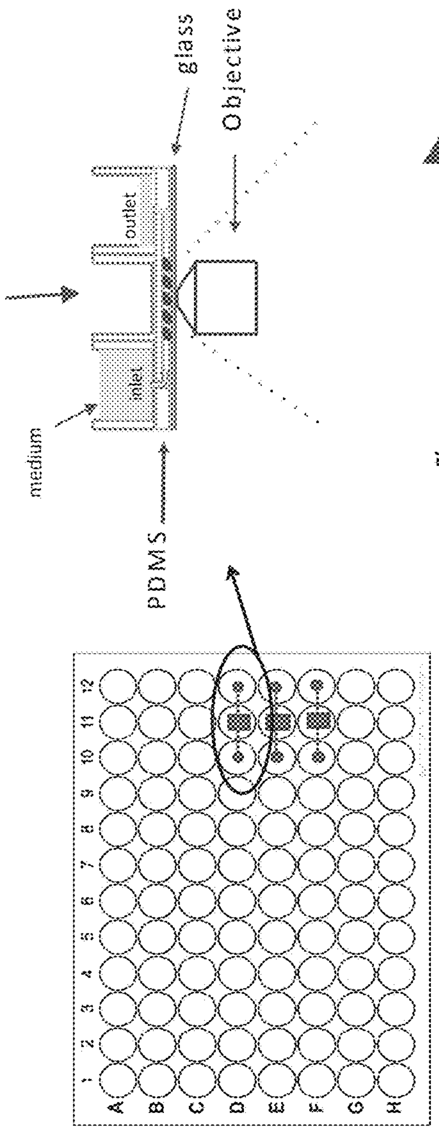
FIG. 2A depicts a high-throughput microfluidic device according to an embodiment of the present disclosure with a 2D array of functional modules interfacing with a 96-well multiwell plate. One module spanning three wells is circled and illustrated in a side view, showing inlet and outlet as well as the observational area.
Figure 2B:
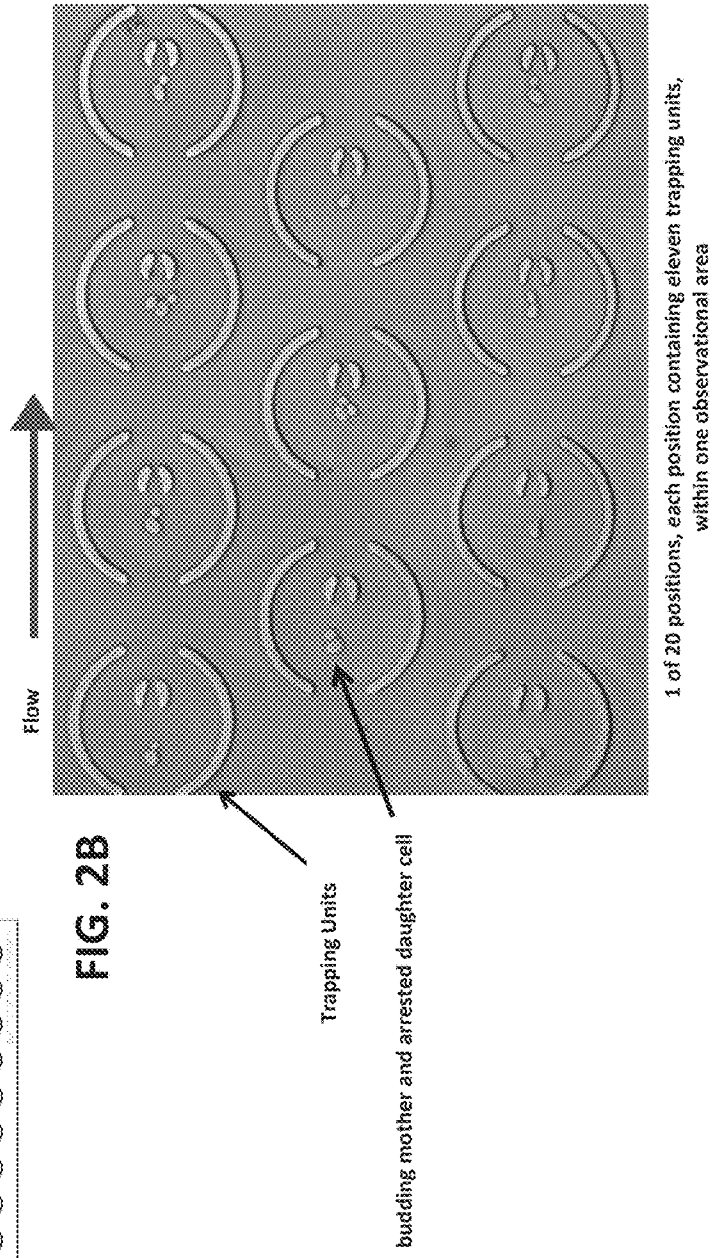
FIG. 2B shows the direction of flow through one position of twenty positions within an observational area according to an embodiment of the present disclosure.

Shown in FIG. 2A is one design of a series of functional modules, each module corresponding to three wells of a 96-well microtiter (multiwell) plate. In this design, each module has an observational area (corresponding to the middle well of a 3-well long module) including a microfluidic device layer having arrays of trapping units designed to trap DAP mother cells (See FIG. 2B showing trapping units shaped in two semi-circles having open gates and two mini-arcs inside). The trapping units in the microfluidic layer favor the trapping and holding of one DAP mother cell per set of trapping units. Together with the DAP yeast strain (i.e., a yeast strain having the DAP construct integrated into its genome), the functional modules allow measurement of the lifespan of the mother cells. Using the presently described microfluidic device and method, the problem of high-throughput counting of daughter cells produced by each mother (a major bottleneck for all existing designs of microfluidic devices for yeast aging studies) has been solved. With this microfluidic device and method employing this multiwell-plate-based design, multiple yeast strains can be handled in parallel and loaded into and/or cultured in the wells of one or more multiwell plates. A multichannel pipette or liquid handling robot can be used to transfer strains to another multiwell plate, or to the device described herein, or to add or change media, and/or to add potential drug compounds for screening for drugs effective to modulate replicative lifespan (RLS).

As described herein, fluid (or air) pressure is used to generate a directional flow through the modules in the microfluidic device, such that flow enters the modules at the inlets, which inlets are in fluid communication with the microfluidic layer's observational area including the cell-trapping units/microstructures, and the cell-trapping and observational area is in fluid communication with outlets, for outflow from the module. Fluid media or air pressure can be applied through a custom designed multi-well plate cover connected to a pump (see FIGS. 8 through 18, and Methods section for more details). The multiwell-plate-based device makes it possible to load/populate all the trapping units in the observational areas corresponding to the middle wells on the multiwell plate in just a few minutes. In addition, when working with yeast strains with DAP construct, there is no need for removing the daughter cells, and thus no pumps and tubes are necessary for media flow during the daughter cell-counting process. The system is easy to set up and operate, and cost effective as a drug screening platform. Because no continuous flow is necessary and the number of cells per cell treatment well remains low, a mere ~200 μL of liquid media may be used for each strain/treatment/drug-concentration, compared to the typical ~300 μL/hour continuous flow over 72 hours as required by previously developed microfluidic devices. Thus, the presently disclosed microfluidic device requires only 1/100 of the drug required by the previous methods, a significant savings.

Figure 8A:
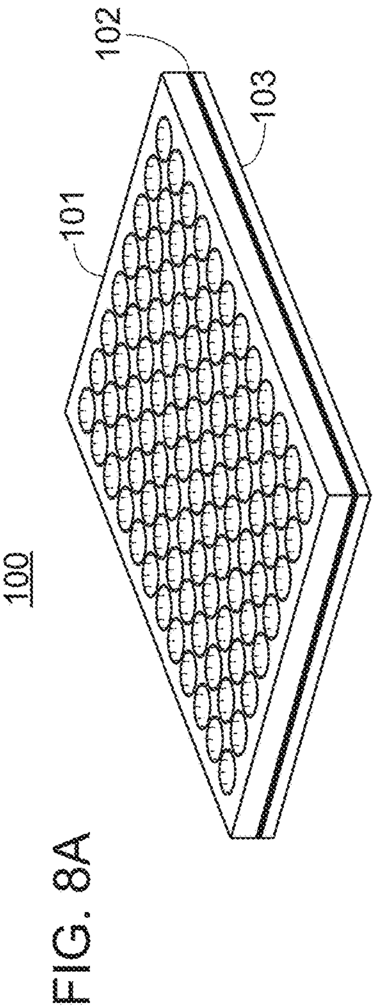
FIG. 8A depicts a yeast cell culture device including a multiwell plate integrated with a microfluidic device positioned beneath the multiwell plate according to an embodiment of the present disclosure.
Figure 8B:
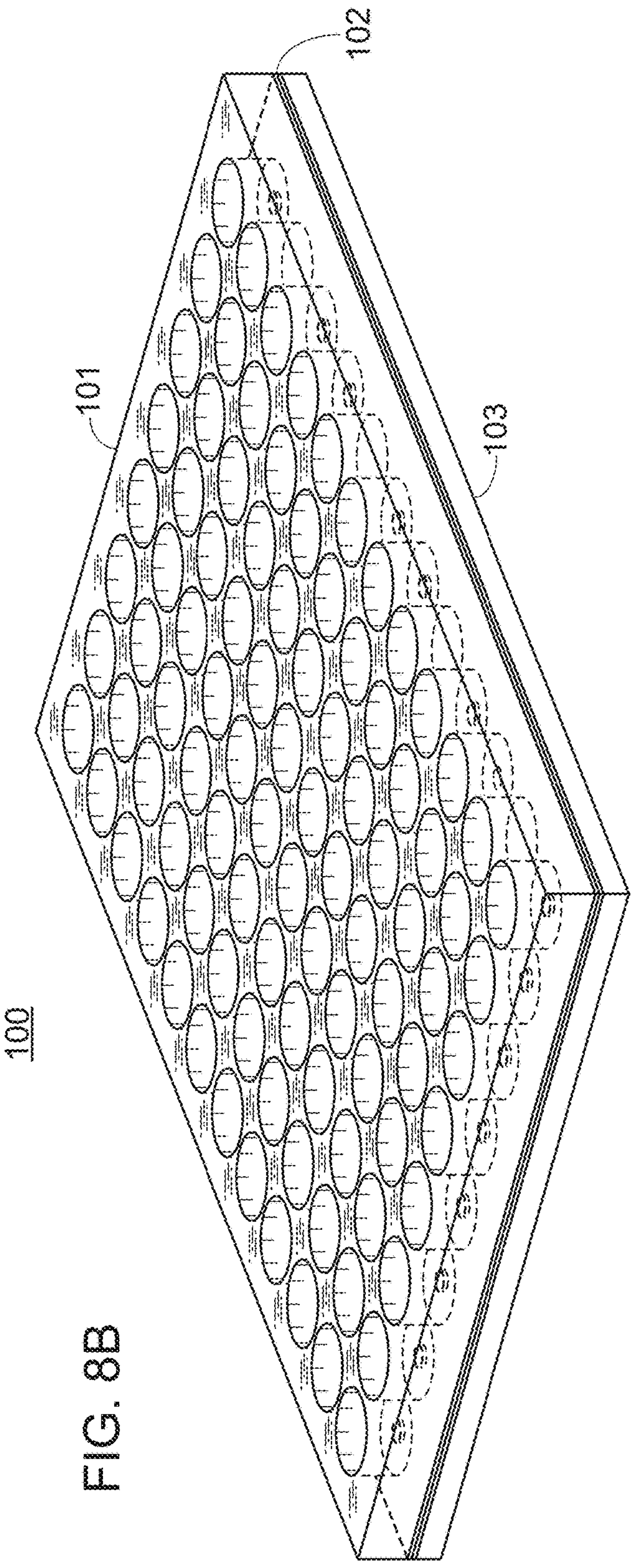
FIG. 8B shows a transparent view of the multiwell plate of FIG. 8A with holes drilled in certain wells to allow flow into the microfluidic device beneath.
Figure 8C:
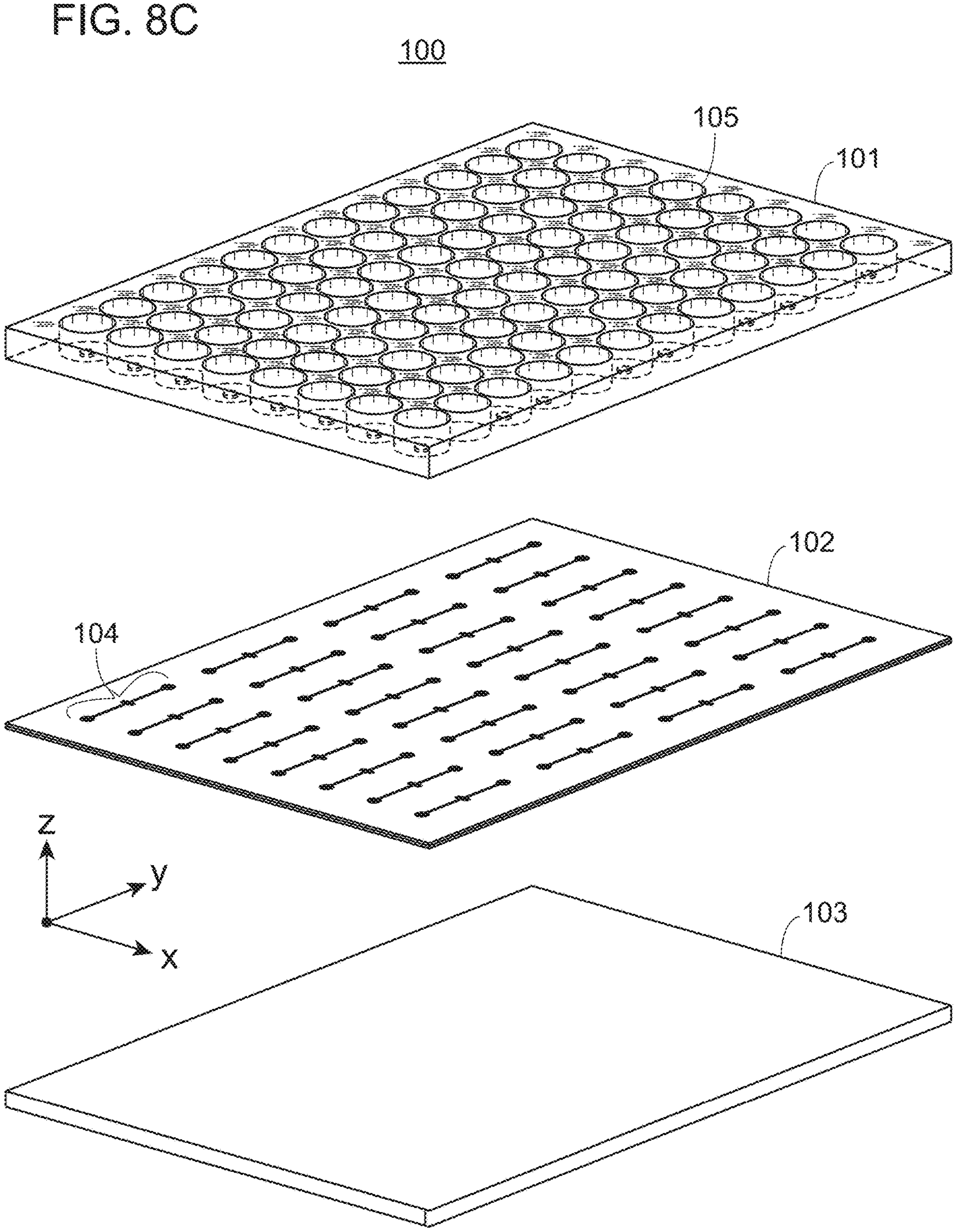
FIG. 8C is an exploded view of the yeast cell culture device of FIG. 8A including the multiwell plate of 8B, and the underlying microfluidic device with 32 modules, and a bottom substrate/layer (e.g. a glass plate).

FIG. 8A depicts a yeast cell culture device 100 including a multiwell plate 101 integrated with a microfluidic device 102 positioned beneath the multiwell plate. FIG. 8B shows a transparent view of the multiwell plate 101 with holes drilled in certain wells to allow flow into the microfluidic device beneath. FIG. 8C is an exploded view of the yeast cell culture device 100 including the multiwell plate 101 of 8B, and the underlying microfluidic device 102 with 32 modules, and a bottom substrate/layer 103 (e.g. a glass plate).

Figure 9:
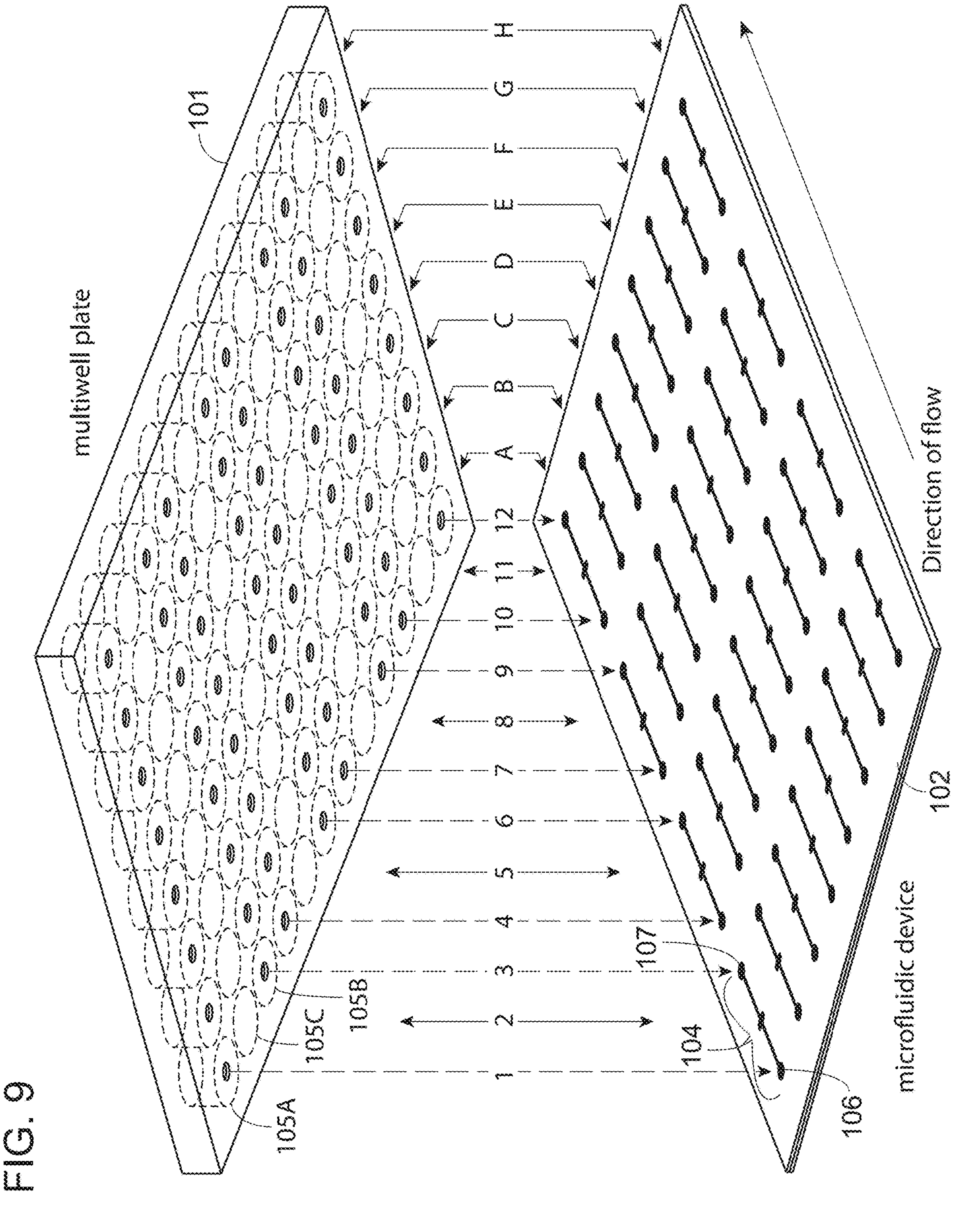
FIG. 9: depicts the multiwell plate of FIG. 8A with holes drilled into wells in columns 1, 3, 4, 6, 7, 9, 10 and 12 of a multiwell plate, and the corresponding microfluidic layer having inlets corresponding to columns 1, 4, 7 and 10, and outlets corresponding to columns 3, 6, 9 and 12.

FIGS. 8B and 9 show the multiwell plate 101 with holes drilled into wells (e.g., 105A-105C) in columns 1, 3, 4, 6, 7, 9, 10 and 12 of the multiwell plate 101, and the corresponding microfluidic device 102 having inlets 106 corresponding to columns 1, 4, 7 and 10, and outlets 107 corresponding to columns 3, 6, 9 and 12. FIGS. 2A, 9, 11-17 illustrate an example of a microfluidic device 102 having 32 modules, wherein each module 104 corresponds to three wells of a 96-well plate. FIG. 16 shows an embodiment in which each module 104 is 18 mm in length (and has 9 mm of space between each module). One of ordinary skill in the art will understand that the specific format and measurements may be altered depending, e.g., on the number of wells in the multiwell plate, density of trapping units, the desired number of modules, etc. The trapping units 110 are arrayed in the observational area 109 corresponding to the middle well of the three wells each module spans, and each observational area has 20 subarrays/positions for observation, with each subarray including 11 trapping units 110 for trapping budding mother and arrested daughter cells. The cell-trapping and observational area of each module 104 in the microfluidic device 102 corresponds to a middle well of the multiwell plate when it is integrated above the microfluidic device 102. Each observational area 108 has 20 subarrays/positions within it (measuring 2292.3 μm in length and 526.7 μm in width/height for the embodiment shown in FIG. 17). The trapping units 110 in this microfluidic device trap single daughter-arrested mother cells as they flow into the inlet 106 (see FIGS. 2A and 14) and through the cell-trapping and observational area 108 of the device. For the illustrated 96 well embodiment, there are 220 trapping units in a single cell-trapping and observational area 108 of each module 104, for trapping up to 220 daughter-arrested mother cells.

Figure 10A:
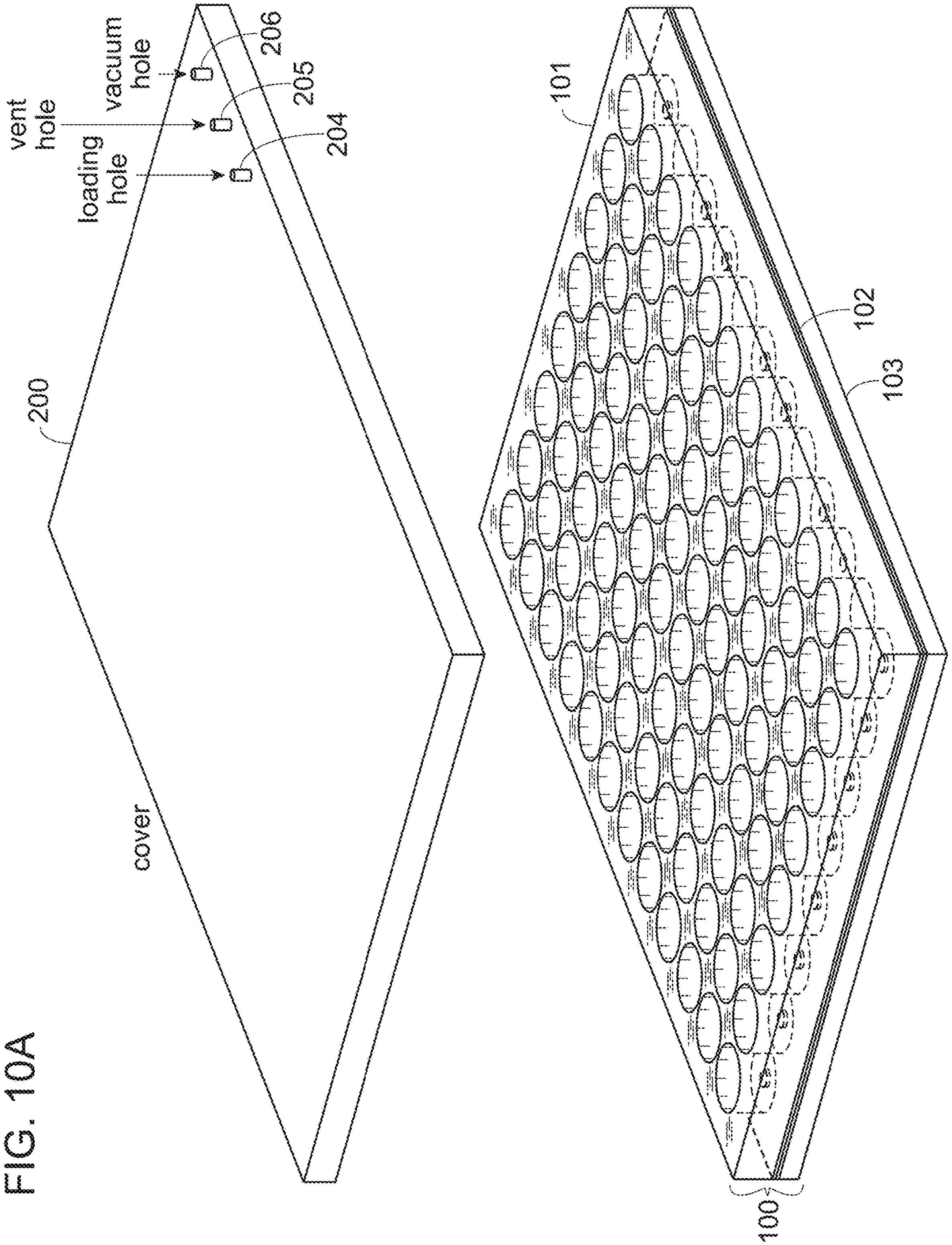
FIGS. 10A and 10B: depicts top (FIG. 10A) and inside (well-facing) (FIG. 10B) views of a device cover according to an embodiment of the present disclosure.
Figure 10B:
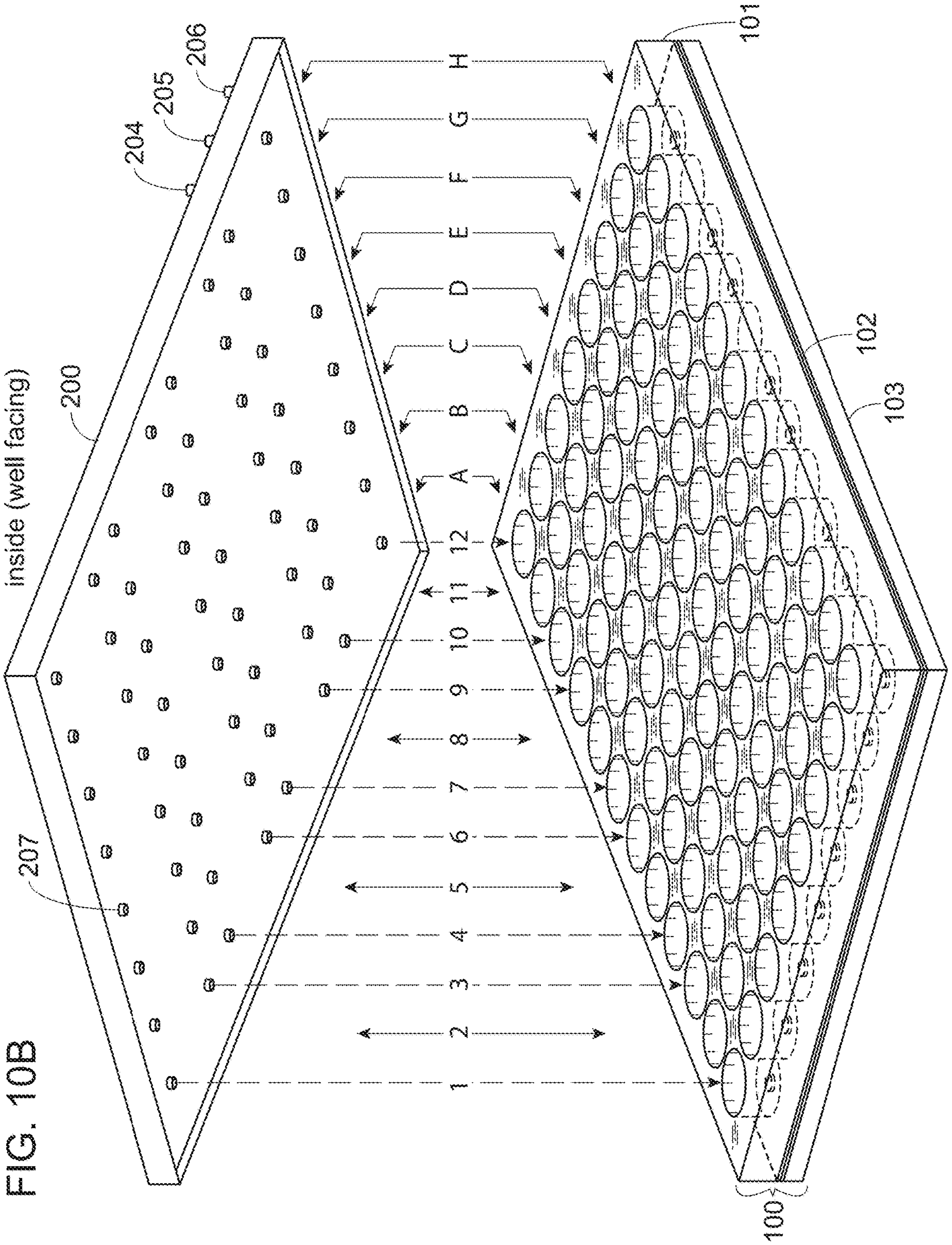

FIGS. 10A and 10B: depicts top (FIG. 10A) and inside (well-facing) (FIG. 10B) views of the optional device cover 200. As in FIG. 2A, the labeling of a 96-well plate is shown with rows labeled A through H and columns labeled 1 through 12. FIGS. 10A and 10B also shows the cover 200, which is positioned above the multiwell plate 101 having holes drilled (as shown in FIG. 9). The cover 200 has holes for loading 204, a vent 205, and application of a vacuum 206 to allow a tight seal. The cover 200 allows fluid (e.g., media) or air pressure to be applied via a loading hole 204. Holes 207 in channels seen in the inside/well-facing side of the cover 200 are in fluid connection with inlets 106 of each module in the microfluidic device 102. Inlet-side channels 119 in the microfluidic device are in fluid connection with the observational area 108, which is in fluid connection with outlet-side channels 120 from each module 104. Thus, when pressure is applied through the loading hole 204 of the cover 200, fluid or air flows through channels 201 (See also FIG. 19) in the cover corresponding to columns 1, 4, 7 and 10 of the multiwell plate, through holes 207 in columns 1, 4, 7 and 10 of the 96-well plate, through inlet-side channels 106 of each module 104, through middle observational area 108 including the trapping units 110, then through outlet-side channels 120 and through the outlet 107 of each module 104, where the outlets correspond to columns 3, 6, 9 and 12 of the multiwell plate, then out through holes 207 and channels 202 (See also FIG. 19) in the cover corresponding to columns 3, 6, 9 and 12 of the 96-well plate, and finally exiting (as air pressure) through a vent hole 205 in the cover (FIGS. 10A and 10B). In one embodiment, the cover has three layers: the bottom layer of the cover is 1 mm in height, the middle layer of the cover is 1 mm in height with inlet 201 and outlet 202 air flow channels each 1 mm in length) (See also FIG. 19), and the top layer of the cover is 3 mm thick. All holes 207 are cylindrical with 1 mm diameter. Again referring to FIGS. 10A and 10B (See also FIG. 19), the cover 200 has four columnar inlet-connected channels 201 in fluid connection with the loading hole 204 in the cover, wherein the four columnar inlet channels 201 allow fluid to enter wells in columns 1, 4, 7 and 10 of the 96-well plate, wherein the inlets 106 of each module 104 correspond to wells in columns 1, 4, 7 and 10 of the 96-well plate. The cover 200 also has four columnar outlet channels 202 in fluid connection with the vent hole 205 in the cover, wherein the four columnar outlet channels 202 allow fluid to exit the wells from columns 3, 6, 9 and 12 of the 96-well plate.

FIG. 11: depicts a microfluidic device 102 corresponding to a 96-well plate having 32 modules 104, the observational area 108 within one module, one position (of 20 positions per observational area) having eleven trapping units 110 in each position. FIG. 11 shows the observational area 108 of one module 104 in the microfluidic device 102, in which channels 119 connect the inlets 106 (see FIGS. 2A and 14) to the observational area 108 (corresponding to the middle well of a 96-well multiwell plate integrated above), and additional channels 120 come out of each observational area 108 to allow flow into the outlets 107. An optional 96-well plate can be integrated with the device. In one embodiment, the budding-mother cell trapping structures 111 and the arrested-daughter cell trapping structures 112 are 3.5 μm high (see, e.g., FIGS. 20 and 21). In one embodiment, the depth of the main and side flow channels (inlet-side and outlet-side flow channels connecting to the middle cell-trapping and observation area having the trapping units) is 33.5 μm. (See, e.g., FIGS. 20 and 21).

Figure 12:
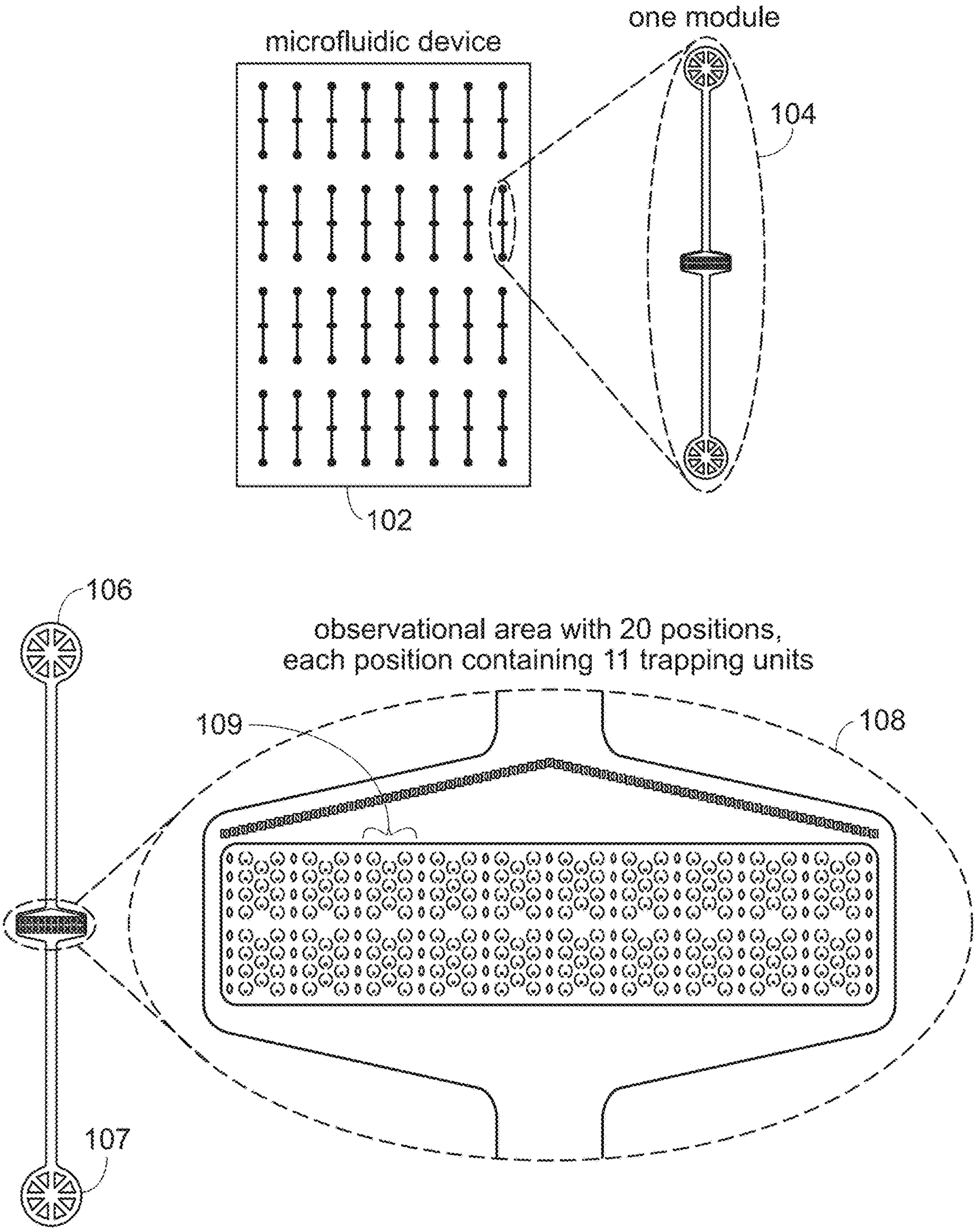
FIG. 12: depicts a microfluidic device having 32 modules, one module, and the observational area within the module, showing 20 positions per observational area according to an embodiment of the present disclosure.

FIG. 12: depicts a microfluidic device 102 having 32 modules, one module 104, and the observational area 108 within the module 104, showing 20 positions per observational area 108.

FIG. 13: depicts an observational area 108 within one module 104, and one observational position having eleven cell trapping units 110.

Figure 14:
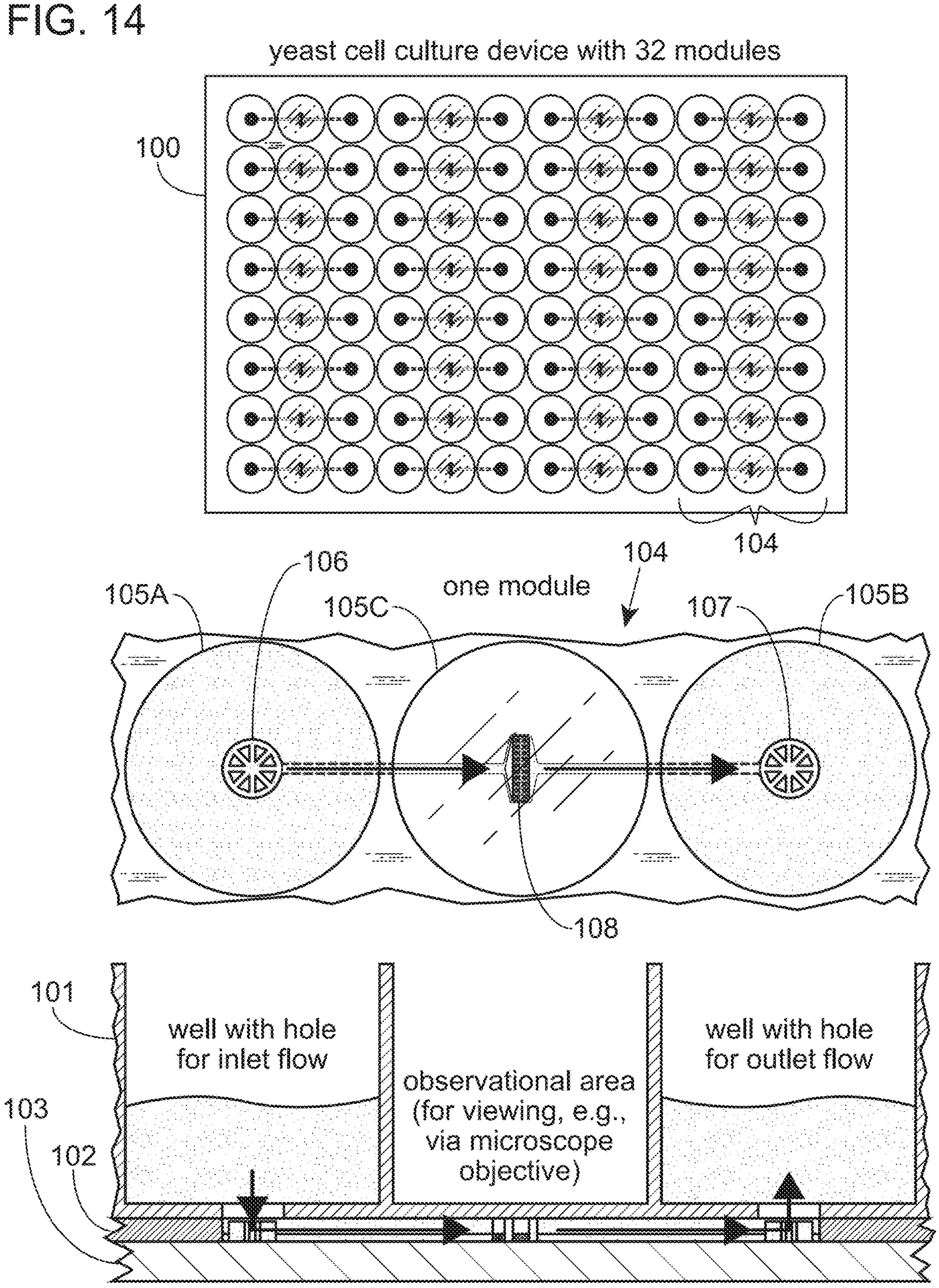
FIG. 14: depicts a microfluidic device with 32 modules, a top view of one module with arrows indicating the direction of flow, and a side view of 3 wells of a multiwell plate integrated with one module of the microfluidic device, indicating the observational area for viewing using a microscope according to an embodiment of the present disclosure.

FIG. 14: depicts a yeast cell culture device 100 with 32 modules 104, a top view of one module with arrows indicating the direction of flow, and a side view of 3 wells of a multiwell plate 101 integrated with one module 104 of the yeast cell culture device 100, indicating the observational area 108 for viewing using a microscope.

Figure 15:
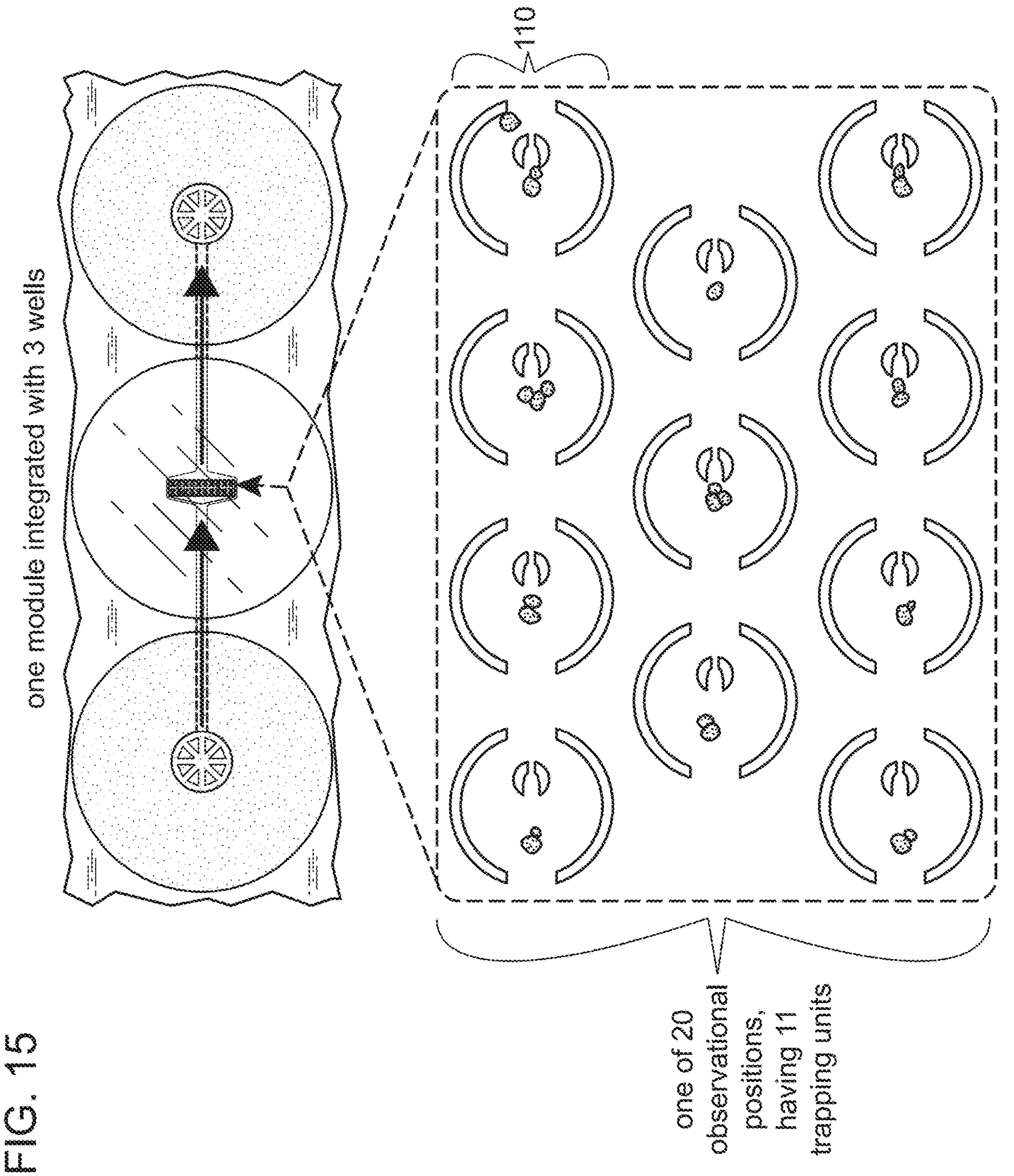
FIG. 15: illustrates a view through the bottom substrate, showing one module of a microfluidic device, and an enlarged view of one of 20 observational positions, each position having 11 trapping units according to an embodiment of the present disclosure.
Figure 16:
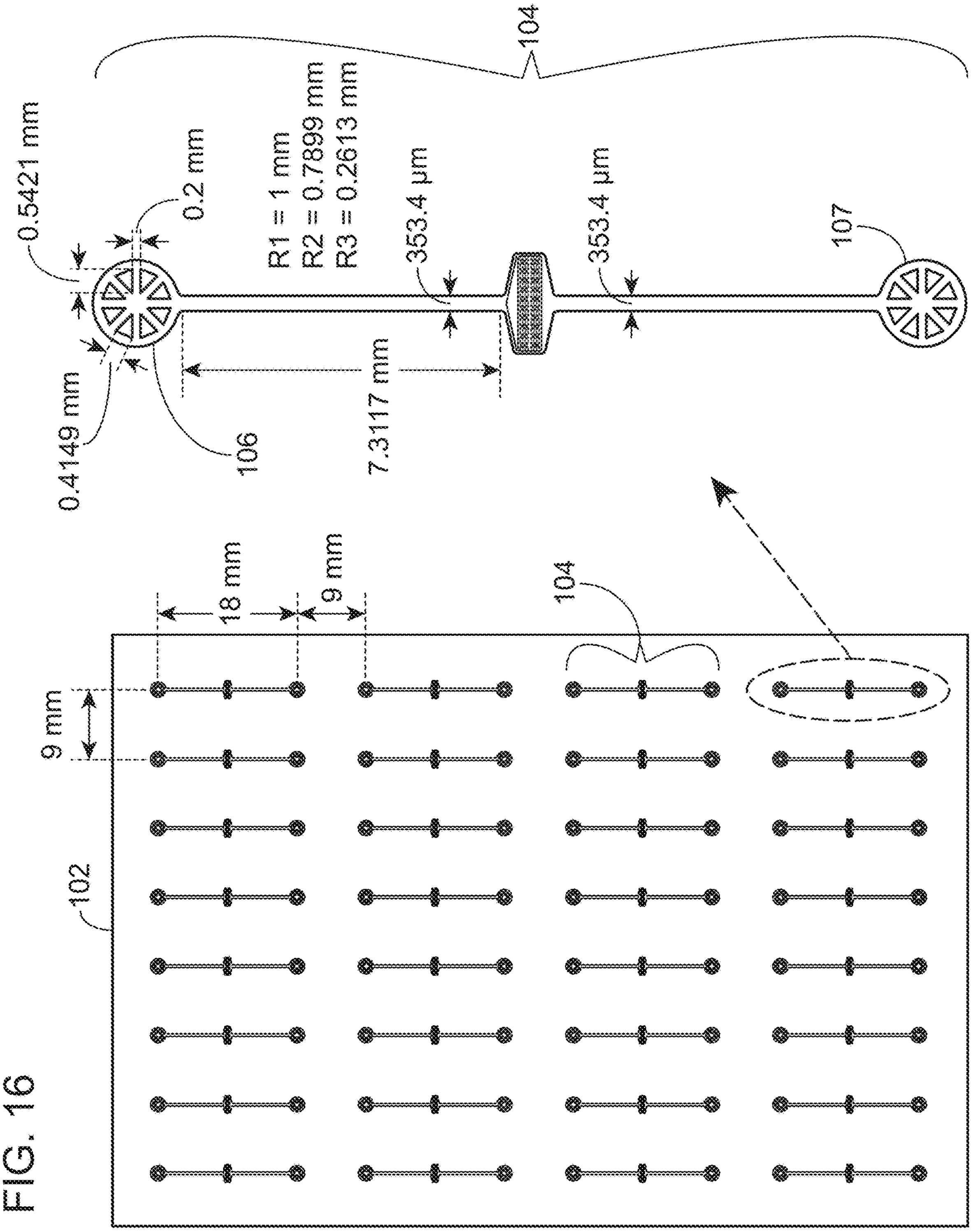
FIG. 16: illustrates a microfluidic device, showing the length of one module, and distance between modules, as well as the measurements, in millimeters (mm), of substructures within a single module according to an embodiment of the present disclosure.

FIG. 15: provides a see-through view, showing one module 104 of a microfluidic device 102, and an enlarged view of one of 20 observational positions, each position having 11 cell trapping units 110.

FIG. 16: illustrates a microfluidic device 102, showing the length of one module 104, and distance between modules 104, as well as the measurements, in millimeters (mm), of substructures within a single module. One of ordinary skill in the art will understand that the specific format and measurements may be altered depending, e.g., on the number of wells in the multiwell plate, density of trapping units, the desired number of modules, etc.

Figure 17:
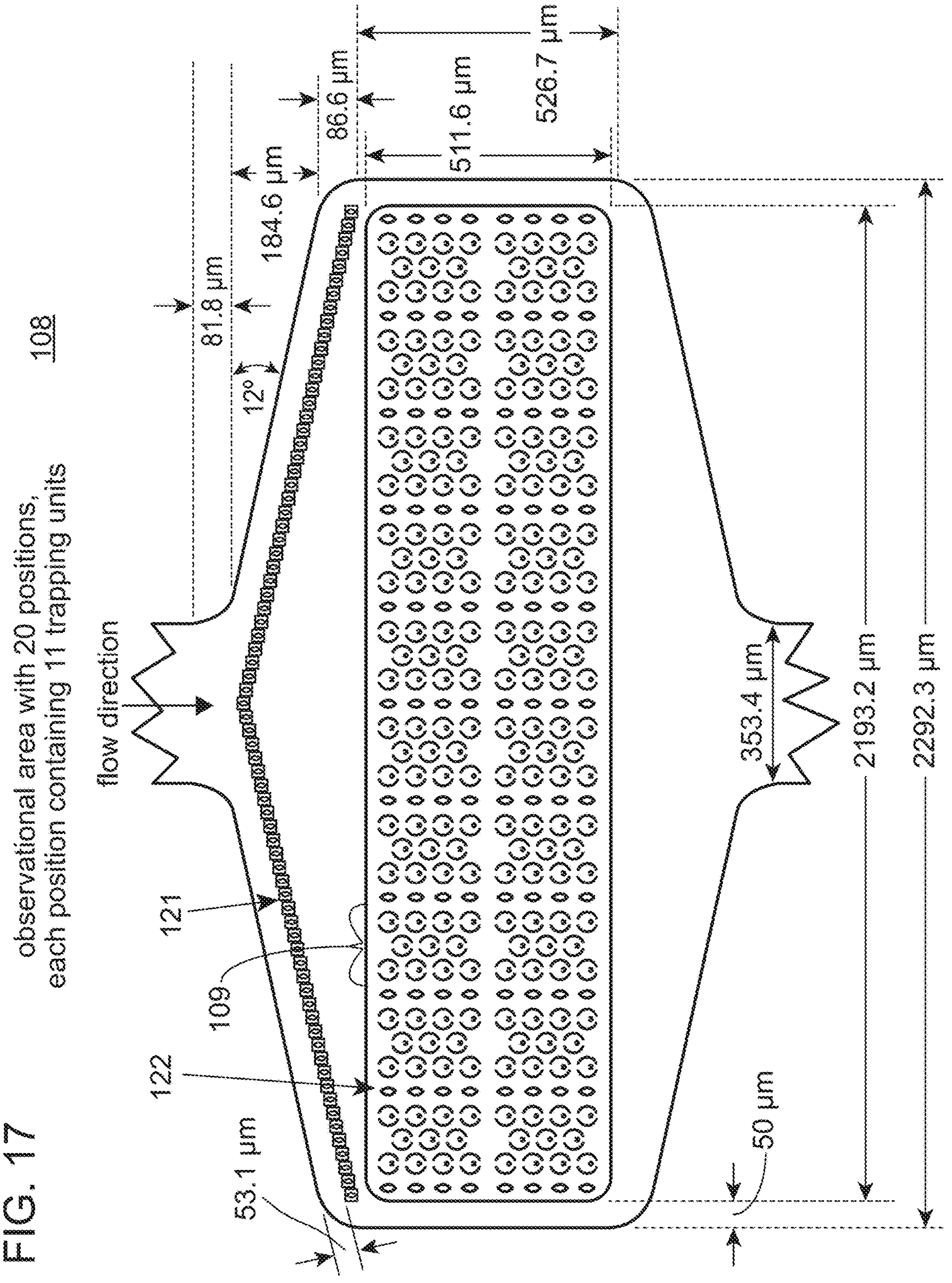
FIG. 17: illustrates the length and width of the observational area of one module, wherein the observational area has 20 positions for observation, each position containing 11 cell-trapping units according to an embodiment of the present disclosure.

FIG. 17: illustrates the length and width of the observational area 108 of one module 104, wherein the observational area 108 has 20 positions for observation, each position containing 11 cell-trapping units 110. One of ordinary skill in the art will understand that the specific format and measurements may be altered depending, e.g., on the number of wells in the multiwell plate, density of trapping units, the desired number of modules, etc. Optional filtering structure 121 is shown, which can be used to prevent larger cells from reaching the observational area of a module 104. Also shown are optional support structures 122, which can perform a variety of functions including separating positions within an observational area, providing landmarks for imaging, and/or providing additional support to prevent channel collapse.

Figure 18:
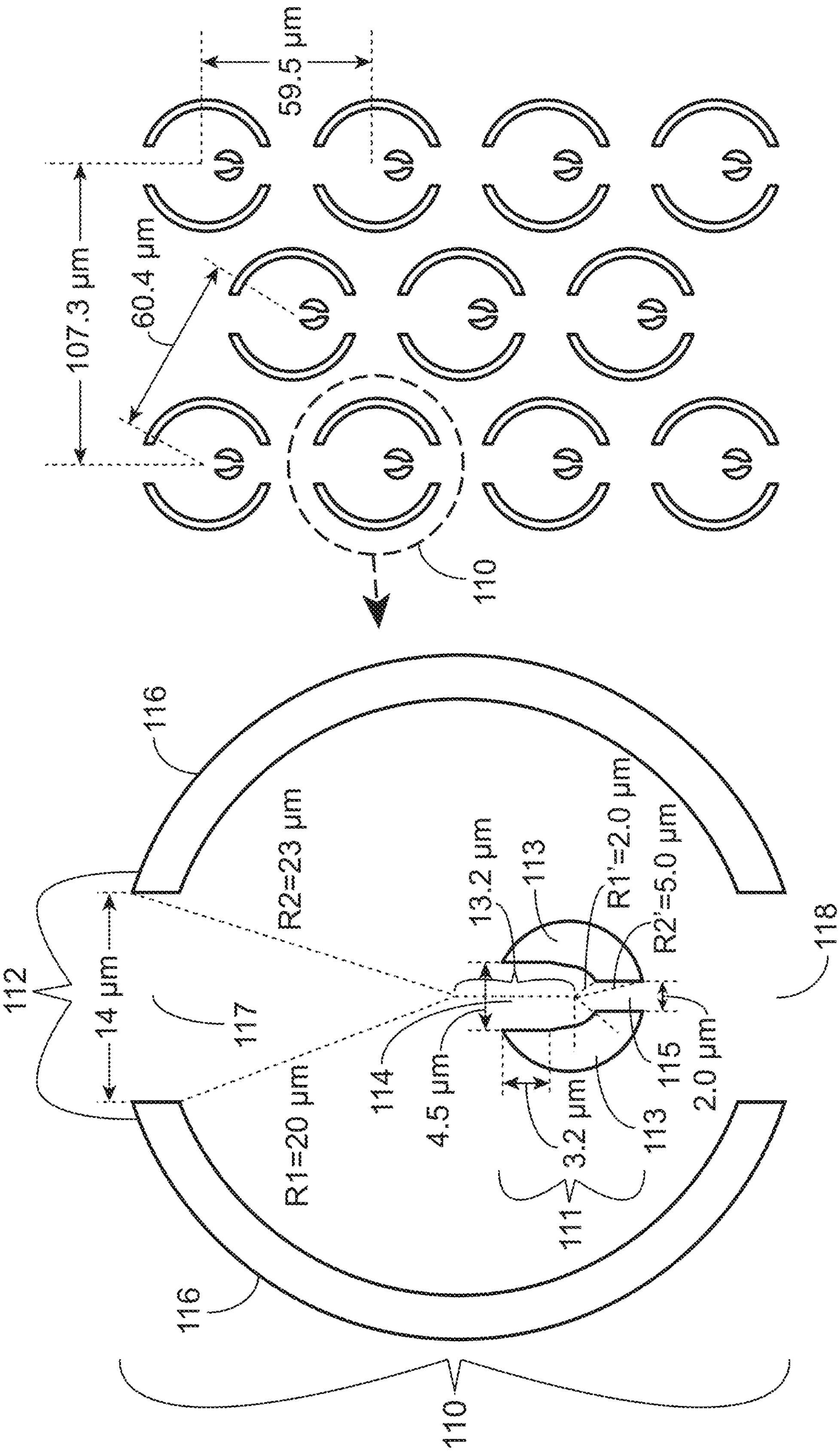
FIG. 18: shows the measurements of one trapping unit (left) in one observational position (right) according to an embodiment of the present disclosure.

FIG. 18: shows the measurements of one trapping unit 110 (left) in one observational position (right). Also shown are exemplary dimensions for a budding-mother cell trapping structure 111 and an arrested-daughter cell trapping structure 112. One of ordinary skill in the art will understand that the specific format and measurements may be altered provided that they allow for efficient capture of budding-mother and arrested daughter cells.

In some embodiments, microfluidic devices of the present disclosure are fabricated using microfabrication technology. Such technology is commonly employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

Materials and Methods for Preparing Microfluidic Devices

Methods and materials which may be used in the preparation of the microfluidic devices described herein are provided.

Substrate: Substrates used in microfluidic systems are the supports in which the necessary elements for fluid transport are provided. The basic structure may be monolithic, laminated, or otherwise sectioned. Commonly, substrates include one or more microchannels serving as conduits for fluid flow. They may also include input ports, output ports, and/or features to assist in flow control.

In certain embodiments, the substrate choice may be dependent on the application and design of the device. Substrate materials are generally chosen for their compatibility with a variety of operating conditions. Limitations in microfabrication processes for a given material are also relevant considerations in choosing a suitable substrate. Useful substrate materials include, e.g., glass, polymers, silicon, metal, and ceramics.

Polymers are standard materials for microfluidic devices because they are amenable to both cost effective and high volume production. Polymers can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Polymers that may be used in the disclosed devices include, e.g., polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS), polysulphone (PSU), and polydimethylsiloxane (PDMS).

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Surface Treatments and Coatings: Surface modification may be useful for controlling the functional mechanics (e.g., flow control) of a microfluidic device. For example, it may be advantageous to keep fluidic species from adsorbing to channel walls.

Polymer devices in particular tend to be hydrophobic, and thus loading of the channels may be difficult. The hydrophobic nature of polymer surfaces also make it difficult to control electroosmotic flow (EOF). One technique for coating polymer surface is the application of polyelectrolyte multilayers (PEM) to channel surfaces. PEM involves filling the channel successively with alternating solutions of positive and negative polyelectrolytes allowing for multilayers to form electrostatic bonds. Although the layers typically do not bond to the channel surfaces, they may completely cover the channels even after long-term storage. Another technique for applying a hydrophilic layer on polymer surfaces involves the UV grafting of polymers to the surface of the channels. First grafting sites, radicals, are created at the surface by exposing the surface to UV irradiation while simultaneously exposing the device to a monomer solution. The monomers react to form a polymer covalently bonded at the reaction site.

Glass channels generally have high levels of surface charge. In some situations, it may be advantageous to apply a polydimethylsiloxane (PDMS) and/or surfactant coating to the glass channels. Other polymers that may be employed to retard surface adsorption include polyacrylamide, glycol groups, polysiloxanes, glyceroglycidoxypropyl, poly(ethyleneglycol) and hydroxyethylated poly(ethyleneimine). Furthermore, for electroosmotic devices it is advantageous to have a coating bearing a charge that is adjustable in magnitude by manipulating conditions inside of the device (e.g. pH). The direction of the flow can also be selected based on the coating since the coating can either be positively or negatively charged.

Specialized coatings can also be applied to immobilize certain species on the channel surface—this process is known by those skilled in the art as "functionalizing the surface." For example, a polymethylmethacrylate (PMMA) surface may be coated with amines to facilitate attachment of a variety of functional groups or targets. Alternatively, PMMA surfaces can be rendered hydrophilic through an oxygen plasma treatment process.

Methods of Fabrication: Microfabrication processes differ depending on the type of materials used in the substrate and the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition): The combination of lithography, etching and deposition techniques may be used to make microcanals and microcavities out of glass, silicon and other "hard" materials. Technologies based on the above techniques are commonly applied in for fabrication of devices in the scale of 0.1-500 micrometers.

Microfabrication techniques based on current semiconductor fabrication processes are generally carried out in a clean room. The quality of the clean room is classified by the number of particles<4 μm in size in a cubic inch. Typical clean room classes for MEMS microfabrication are 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 μm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate—area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physico-chemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 μm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features are usually sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used should ideally have a thermal expansion coefficient near that of silicon (e.g. CORNING® PYREX® 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100 °C.

Polymers/Plastics: A number of techniques may be employed for micromachining plastic substrates in accordance with embodiments of the present disclosure. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In microinjection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is well suited for microchannels between about 5 and 500 μm. Specific properties of PDMS make it particularly suitable for microfluidic purposes:

1) It is optically clear which allows for visualization of the flows;

2) PDMS when mixed with a proper amount of reticulating agent has elastomeric qualities that facilitates keeping microfluidic connections "watertight;"
3) Valves and pumps using membranes can be made with PDMS because of its elasticity;
4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma.
5) PDMS is permeable to gas. Filling of the channel with liquids is facilitated even when there are air bubbles in the canal because the air bubbles are forced out of the material. But it's also permeable to non polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180 °C). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process. Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials such as stainless steel make very durable mold inserts and can be micromachined to form structures down to the 10-μm range. Various other micromachining techniques for microfabrication exist including μ-Electro Discharge Machining (μ-EDM), μ-milling, focused ion beam milling. μ-EDM allows the fabrication of 3-dimensional structures in conducting materials. In μ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices must be closed up before they can become functional. Common problems in the bonding process for microfluidic devices include the blocking of channels and changes in the physical parameters of the channels. Lamination is one method used to seal plastic microfluidic devices. In one lamination process, a PET foil (about 30 μm) coated with a melting adhesive layer (typically 5-10 μm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65 °C for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. Ultrasonic welding is another bonding technique that may be employed in some applications.

In one aspect, a system is provided, the system including the microfluidic device or yeast cell culture device and a camera configured to capture images and/or video of the cell-trapping and observational area. Any suitable camera or image capture device known in the art may be utilized. In some embodiments, a suitable camera will be a digital camera, which can be integrated with a computer processing system to automate the image capture and recording process.

Method of Measuring Replicative Lifespan (RLS)

The present disclosure provides a method of determining replicative age of a yeast cell, including (a) culturing one or more DAP yeast strains as described herein in a first culture medium under non-repressed conditions for the conditional promoter; (b) culturing the one or more DAP yeast strains from step (a) in a second culture medium under repressed conditions for the conditional promoter; and (c) counting arrested daughter cells produced by the one or more DAP yeast strains to determine replicative age of one or more mother cells of the DAP yeast strain. In some embodiments, the method includes contacting one or more of the one or more DAP yeast strains with a test compound and determining the effect of the test compound on replicative age of the one or more DAP yeast strains contacted with the compound. In some embodiments of the method of determining replicative age of a yeast cell, simultaneously with step (a) and/or step (b), introducing a test compound to the culture medium for assessing an effect of the test compound on replicative age of the one or more DAP yeast strains. In some embodiments, one or both of steps (a) and (b) are performed in the microfluidic device or yeast cell culture device (or using the system), and the counting arrested daughter cells produced by the one or more DAP yeast strains to determine replicative age includes counting arrested daughter cells trapped in the cell-trapping and observational area.

In one aspect, also provided is a method of determining replicative age of one or more yeast cells, comprising: culturing one or more DAP yeast strains in a first culture medium under non-repressed conditions for the conditional promoter; flowing the one or more DAP yeast strains into the plurality of functional modules of a microfluidic device or yeast cell culture device described herein, through the inlets; entrapping the one or more DAP yeast strains in the arrays of trapping units in the cell-trapping and observational areas; culturing the entrapped DAP yeast strains in a second culture medium under repressed conditions for the conditional promoter such that a population of non-dividing daughter cells is produced and entrapped within the array of trapping units in proximity to corresponding mother cells of the DAP yeast strain; and quantifying/quantitating or counting arrested daughter cells produced by the one or more DAP yeast strains to determine replicative age of one or more mother cells of the DAP yeast strain. In some embodiments, the method includes imaging the budding mother and arrested daughter cells of the one or more DAP yeast strains prior to quantifying or counting. In some embodiments of the method, the mother cells are trapped in the budding-mother cell trapping structures and the arrested-daughter cells produced as a result of budding of a trapped mother cell are trapped in the arrested-daughter cell trapping structures. In some embodiments of the method, the first culture medium includes galactose and the second culture medium includes glucose in place of galactose. One of ordinary skill in the art will be able to select a suitable culture medium based on the nature of the conditional promoter system being utilized.

In one aspect, is the present disclosure provides a method of measuring replicative lifespan (RLS), the method including: culturing one or more DAP yeast strains in a first culture medium under non-repressed conditions for the conditional promoter; culturing the one or more DAP yeast strains in a second culture medium under repressed conditions for the conditional promoter; amplifying barcode sequences of mother cells and arrested daughter cells resulting from the culturing; sequencing the amplified barcode sequences; and quantitating arrested daughter cells based on the sequencing thereby measuring RLS of the one or more DAP yeast strains. In some embodiments of the method, the one or more DAP yeast strains further include one or more genomic mutations.

In one aspect, also provided is a method of screening and identifying compounds that modulate replicative lifespan (RLS), including (a) culturing one or more DAP yeast strains in a first culture medium under non-repressed conditions for the conditional promoter; (b) switching the one or more DAP yeast strains to a second culture medium under repressed conditions for the conditional promoter, and for each of the one or more DAP yeast strains under repressed conditions, treating with one or more test compounds; (c) counting or quantifying arrested daughter yeast cells to determine replicative age; and (d) identifying test compounds that modulate RLS as compared to an untreated control. In some embodiments of the method, the one or more test compounds are members of a library of test compounds. In some embodiments, the method further includes, after the DAP strains are in the second culture medium under repressed conditions, applying each of the strains to a microfluidic device or yeast cell culture device as described herein and, and imaging arrested daughter yeast cells in the cell-trapping and observational area. In some embodiments, the method further includes, before step (a), barcoding the strains to produce unique strains with individual barcodes. In some embodiments, the method further includes sequencing and quantifying cells having individual barcodes.

In one aspect, also provided herein is a method of screening and identifying mutant yeast strains having an altered/enhanced replicative lifespan (RLS), including (a) culturing a library of mutant DAP strains in a first culture medium in one or more multiwell plates under non-repressed conditions for the conditional promoter, where the mutant DAP strains are DAP strains, which further include one or more genomic mutations; (b) switching the library of mutant DAP strains to a second culture medium under repressed (daughter-arrested) conditions for the conditional promoter; (c) applying each member of the library of mutant DAP strains under repressed (daughter-arrested) conditions to a microfluidic device or yeast cell culture device; (d) counting or quantifying arrested daughter yeast cells to determine RLS; and (e) identifying mutant DAP strains having an altered/enhanced RLS as compared to an unmutated DAP strain control. In some embodiments, each member in the library of mutant DAP strains being screened resides in a well of one or more multiwell plates.

Barcodes allow for individual identification of each member of a population having hundreds to thousands of distinct members. Thus, an entire library, population, pool and/or mixture of hundreds to thousands of cells, strains or mutants can be treated en masse and later distinguished, and the effects on individual members (e.g., strains, mutants, drug treatments) can be assessed, and any effects on replicative life span (RLS) noted. In some embodiments, the method provided herein allows replicative lifespan measurement using multiplexed barcode sequencing. In some embodiments, the method provided herein allows high throughput drug screening by combining the DAP system with multiplexed barcode sequencing.

For the system described herein, barcode sequencing methods may be employed. In some embodiments, the DAP yeast strain is barcoded. In some embodiments, a library of yeast mutants also includes the DAP genomic integration, and the entire library is barcoded. In some embodiments, a library, population, pool and/or mixture of hundreds to thousands of cells, strains or mutants is barcoded and the barcoded library, population, pool or mixture is used in the presently described methods of assessing replicative lifespan (with or without using the device, and/or with or without the camera or imaging systems described herein).

In some embodiments of the method provided herein, multiplex barcode sequencing of DAP strains is used for screening compounds for effects on RLS. In some embodiments, the barcoded cells are cultured in one or more multiwell plates and treated with a library of compounds/drugs potentially affecting RLS, where one barcode corresponds to one unique drug, and then the cells in each of the wells treated with a barcoded drug are combined into a pool for genomic DNA extraction and barcode sequencing.

In one aspect, also provided herein is a method of screening and identifying mutant yeast strains having an altered/enhanced replicative lifespan (RLS), including (a) culturing a pooled library of mutant DAP strains in a starting liquid culture under repressed, daughter-arrested conditions, wherein the mutant DAP strains are DAP strains which further include one or more genomic mutations and a nucleic acid barcode sequence; (b) aliquoting the starting liquid culture into two or more liquid cultures with equal volume, where each aliquot is allowed to grow for a different length of time ($t_i$, where i=0, . . . N−1), at which time a fixed amount of external reference cells having distinguishing barcodes is added, cells are harvested, DNA extracted and barcodes PCR-amplified with an ith index sequence added; and (c) pooling together all N sequence samples and performing next generation sequencing to identify mutant yeast strains having an altered/enhanced replicative lifespan (RLS).

In one aspect, also provided herein is a method of screening and identifying compounds that modulate replicative lifespan (RLS), including (a) culturing, under non-repressed conditions, a library of wildtype barcoded DAP strains in one or more multiwell plates, each well containing one member of the library with a unique barcode; (b) at time $t_0$, transferring and culturing each member of the library to an equivalent well in one or more duplicate multiwell plates under repressed, daughter-arrested conditions, where each duplicate plate is allowed to grow for a different length of time ($t_i$, where i=0, . . . N−1), and adding a test compound; (c) pooling cultures of the ith duplicate for each timepoint i, and adding a fixed amount of external reference cells having distinguishing barcodes; and (d) harvesting, extracting and PCR-amplifying barcodes with an ith index sequence added; and (e) performing next generation sequencing to identify compounds that modulate RLS.

In one aspect, also provided herein is a method of simultaneously measuring the effects on replicative lifespan of $10^2$-$10^3$ mutations and/or compounds/candidate drugs by quantifying barcoded DAP yeast strain daughter cells in liquid culture using next generation sequencing.

In some embodiments, synthetic genetic array technology is used to generate a library of barcoded wild type strains with a DAP construct (as described herein) integrated. In some embodiments, a barcoded, haploid wild type library is mated with a DAP strain, to generate a library of diploids with barcodes and the DAP construct integrated. The diploids thereby generated are then sporulated, followed by selecting for haploids using selectable markers for both the barcode and DAP. In some embodiments, each member of the library of barcoded wild type strains resides in a well of one or more multiwell plates and has a unique barcode.

In some embodiments, a library of mutant DAP strains is generated by obtaining and mating a library of haploid mutant strains of one mating type with a haploid DAP strain of opposite mating type and sporulating the resulting diploids, then selecting for haploids having selectable markers for both the DAP integration and the mutation from the library. In some embodiments, each member of the library of haploid mutant strains of one mating type resides in a well of one or more multiwell plates.

In some embodiments, the one or more test compounds are members of a library of test compounds in one or more multiwell plates.

The technology disclosed herein was validated using known longevity mutants and drugs. The system/platform described herein was used for preliminary screening and discovery of new genes/drugs that extend yeast lifespan. Compared to previous studies, the present system allows for high throughput screening of small molecule drugs using replicative lifespan as the direct readout, instead of using surrogate markers. The presently disclosed system drastically improves and accelerates the discovery of anti-aging drugs and the study of conserved mechanisms of aging across species.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

1. A nucleic acid construct for integration into a specific locus of a yeast cell genome, comprising:
   (a) an integration sequence at each end of the nucleic acid construct configured to effect integration into a yeast genomic locus between a sequence upstream of the start codon of an endogenous gene encoding an essential plasma membrane protein and the start codon of the gene; and
   (b) two cassettes oriented in opposite transcriptional directions, comprising:
      (i) a first cassette comprising a mother-specific promoter configured to control transcription of an exogenous copy of the gene encoding the essential plasma membrane protein; and
      (ii) a second cassette comprising a conditional promoter configured to control transcription of the endogenous gene upon integration into the yeast genomic locus.
2. The nucleic acid construct of 1, wherein the construct is configured such that, upon integration into the yeast genomic locus between the sequence upstream of the start codon of the gene encoding the essential plasma membrane protein and the start codon of the gene:

(a) the first cassette drives transcription, via the mother-specific promoter, of the integrated exogenous copy of the gene encoding the essential plasma membrane protein; and (b) the second cassette drives transcription, via the conditional promoter, of the endogenous gene encoding an essential plasma membrane protein.

3. The nucleic acid construct of 1 or 2, further comprising a first reporter marker transcriptionally linked in-frame to the exogenous copy of the gene encoding the essential plasma membrane protein.

4. The nucleic acid construct of any one of 1-3, comprising a second reporter marker operably linked to the conditional promoter, such that upon integration into the yeast genomic locus between the sequence upstream of the start codon of the gene encoding the essential plasma membrane protein and the start codon of the gene, the second reporter marker is transcriptionally linked in-frame to the endogenous gene encoding an essential plasma membrane protein.

5. The nucleic acid construct of 3 or 4, wherein the first and/or second reporter marker is a fluorescent reporter.

6. The nucleic acid construct of 5, wherein the fluorescent reporter is GFP or dTomato.

7. The nucleic acid construct of any one of 1-6, further comprising one or more selectable markers.

8. The nucleic acid construct of 7, wherein the one or more selectable markers is selected from aphA1, ble, Cat, CmR, CYH2, nat, kan, pat, AUR1-C and hphNT1.

9. The nucleic acid construct of 8, wherein the selectable marker is hphNT1.

10. The nucleic acid construct of any one of 1-9, wherein the gene encoding the essential plasma membrane protein is selected from the group consisting of ALR1, ARP3, AVO1, BNI1, CDC19, CDC42, COF1, CTR1, CYR1, EFR3, ERG25, EXO70, FCY21, GPA1, GUP1, HIP1, HKR1, HRR25, KOG1, LST8, MSC1, MSS4, PAN1, PFY1, PGA3, PGI1, PGK1, PHO90, PKC1, PMA1, PTR3, RHO1, RHO3, RSP5, SEC1, SEC4, SEC9, SSY1, SSY5, STT4, TCP1, TOR2, TPI1, UGP1 and YPP1.

11. The nucleic acid construct of 10, wherein the gene encoding the essential plasma membrane protein is PMA1.

12. The nucleic acid construct of any one of 1-11, wherein the conditional promoter is a temperature-sensitive promoter selected from HSF1 and MET17, a glucose-repressible promoter selected from pGAL1, PCK1 and MAL2, a methionine- and/or cysteine-repressible promoter MET3, or other conditional gene expression system selected from a tetracycline-regulatable system, the Cre-Lox recombination system, the Flp-FRT recombination system and the LexA-ER-AD system.

13. The nucleic acid construct of 12, wherein the conditional promoter is pGAL1.

14. The nucleic acid construct of any one of 1-13, wherein the mother-specific promoter is selected from pHO, HO-TX, TXC and TXC2.

15. The nucleic acid construct of 14, wherein the mother-specific promoter is pHO.

16. A vector comprising the nucleic acid construct of any one of 1-15.

17. The vector of 16, comprising pIDS2GH (SEQ ID NO: 1) or pIDS2RH (SEQ ID NO: 2).

18. A yeast cell, comprising the vector of 16 or 17.

19. A daughter-arresting program (DAP) yeast strain, comprising:

an exogenous nucleic acid sequence integrated into the genome between a sequence upstream of the start codon of an endogenous gene encoding an essential plasma membrane protein and the start codon of the gene, wherein the integrated nucleic acid sequence comprises:

(a) a mother-specific promoter driving transcription of an exogenous copy of the gene encoding the essential plasma membrane protein; and (b) a conditional promoter driving transcription of the endogenous gene encoding the essential plasma membrane protein, wherein the mother-specific promoter and the conditional promoter are oriented in opposite transcriptional directions.

20. The DAP yeast strain of 19, wherein the integrated nucleic acid sequence further comprises a first reporter marker transcriptionally linked in-frame to the exogenous copy of the gene encoding the essential plasma membrane protein.

21. The DAP yeast strain of 19 or 20, wherein the integrated nucleic acid sequence further comprises a second reporter marker transcriptionally linked in-frame to the endogenous gene encoding an essential plasma membrane protein.

22. The DAP yeast strain of 20 or 21, wherein the first and/or second reporter marker is a fluorescent reporter.

23. The DAP yeast strain of 22, wherein the fluorescent reporter is GFP or dTomato.

24. The DAP yeast strain of any one of 19-23, wherein the integrated nucleic acid sequence further comprises one or more selectable markers.

25. The DAP yeast strain of 24, wherein the one or more selectable markers is selected from aphA1, ble, Cat, CmR, CYH2, nat, kan, pat, AUR1-C and hphNT1.

26. The DAP yeast strain of 25, wherein the selectable marker is hphNT1.

27. The DAP yeast strain of any one of 19-26, wherein the gene encoding the essential plasma membrane protein is selected from the group consisting of ALR1, ARP3, AVO1, BNI1, CDC19, CDC42, COF1, CTR1, CYR1, EFR3, ERG25, EXO70, FCY21, GPA1, GUP1, HIP1, HKR1, HRR25, KOG1, LST8, MSC1, MSS4, PAN1, PFY1, PGA3, PGI1, PGK1, PHO90, PKC1, PMA1, PTR3, RHO1, RHO3, RSP5, SEC1, SEC4, SEC9, SSY1, SSY5, STT4, TCP1, TOR2, TPI1, UGP1 and YPP1.

28. The DAP yeast strain of 27, wherein the gene encoding the essential plasma membrane protein is PMA1.

29. The DAP yeast strain of any one of 19-28, wherein the conditional promoter is a temperature-sensitive promoter selected from HSF1 and MET17, a glucose-repressible promoter selected from pGAL1, PCK1 and MAL2, a methionine- and/or cysteine-repressible promoter MET3, or other conditional gene expression system selected from a tetracycline-regulatable system, the Cre-Lox recombination system, the Flp-FRT recombination system and the LexA-ER-AD system.

30. The DAP yeast strain of 29, wherein the conditional promoter is pGAL1.

31. The DAP yeast strain of any one of 19-30, wherein the mother-specific promoter is selected from pHO, HO-TX, TXC and TXC2.

32. The DAP yeast strain of 31, wherein the mother-specific promoter is pHO.

33. The DAP yeast strain of any one of 19-32, wherein the strain further comprises an exogenous nucleic acid barcode sequence.

34. A method of measuring replicative lifespan (RLS), the method comprising:
   culturing one or more DAP yeast strains according to 33 in a first culture medium under non-repressed conditions for the conditional promoter;
   culturing the one or more DAP yeast strains in a second culture medium under repressed conditions for the conditional promoter;
   amplifying barcode sequences of mother cells and arrested daughter cells resulting from the culturing;
   sequencing the amplified barcode sequences; and
   quantitating arrested daughter cells based on the sequencing thereby measuring RLS of the one or more DAP yeast strains.
35. The method of 34, wherein the one or more DAP yeast strains further comprise one or more genomic mutations.
36. A kit comprising the DAP yeast strain of any one of 19-33 and a microfluidic device comprising functional modules for measurement of replicative lifespan (RLS).
37. The kit of 36, further comprising a multiwell plate that can be integrated with the microfluidic device, and optionally further comprising a cover for the multiwell plate.
38. A microfluidic device comprising a plurality of functional modules for measurement of yeast replicative lifespan (RLS), wherein each module comprises:
   (a) an inlet for receiving fluid flow into the module,
   (b) a cell-trapping and observational area, in fluid communication with the inlet, comprising an array of trapping units configured to trap budding mother cells and arrested daughter cells produced therefrom, and
   (c) an outlet, in fluid communication with the cell-trapping and observational area, for flow out of the module.
39. A yeast cell culture device comprising a multiwell plate integrated with a microfluidic device positioned beneath the multiwell plate, the microfluidic device comprising a plurality of functional modules for measurement of RLS, wherein each module corresponds to a plurality of wells of the multiwell plate, and wherein each module comprises:
   (a) an inlet configured to provide fluid flow into the module from a first well of the multiwell plate,
   (b) a cell-trapping and observational area in fluid communication with the inlet and comprising an array of trapping units for trapping budding mother cells and arrested daughter cells produced therefrom, and
   (c) an outlet in fluid communication with the cell-trapping and observational area, configured to provide fluid flow out of the module to a second well of the multiwell plate.
40. The device of 39, wherein the cell-trapping and observational area is positioned beneath a third well of the multiwell plate.
41. The device of 40, wherein the third well of the multiwell plate is positioned between the first and second wells.
42. The device of 41, wherein each module spans the length of three wells of the multiwell plate.
43. The device of any one of 39-42, wherein the multiwell plate has 48, 96 or 384 wells.
44. The device of 43, wherein the multiwell plate has 48 wells and the plurality of functional modules is 16 modules.
45. The device of 43, wherein the multiwell plate has 96 wells and the plurality of functional modules is 32 modules.
46. The device of 43, wherein the multiwell plate has 384 wells and the plurality of functional modules is 128 modules.
47. The microfluidic device of 38 or the yeast cell culture device of any one of 39-46, wherein the array of trapping units comprises:
   a plurality of trapping units, each unit comprising
      a budding-mother cell trapping structure, sized and shaped to trap a budding mother cell and allow fluid flow-through prior to trapping a budding mother cell; and
      an arrested-daughter cell trapping structure associated with each budding-mother cell trapping structure, wherein the arrested-daughter cell trapping structure is configured to allow fluid flow-through and trap the budding-mother and arrested-daughter cells produced as a result of budding of the trapped mother cell.
48. The microfluidic device or yeast cell culture device of 47, wherein the arrested-daughter cell trapping structure encompasses the budding-mother cell trapping structure.
49. The microfluidic device or yeast cell culture device of 47 or 48, wherein the budding-mother cell trapping structure comprises a pair of walls positioned and angled to define a first opening between the two walls and a second opening between the two walls, wherein the first opening is positioned to receive a fluid flow and is wider than the average diameter of a budding-mother cell to be trapped, and wherein the second opening is narrower than the average diameter of a budding-mother cell to be trapped.
50. The microfluidic device or yeast cell culture device of 49, wherein the walls are arcuate.
51. The microfluidic device or yeast cell culture device of 49 or 50, wherein the length of the first opening is at least 2 times the length of the second opening.
52. The microfluidic device or yeast cell culture device of any one of 49-51, wherein the length of the first opening is from about 4.0 μm to about 5 μm, and the length of the second opening is from about 1.5 μm to about 2.5 μm.
53. The microfluidic device or yeast cell culture device of 52, wherein the length of the first opening is about 4.5 μm, and the length of the second opening is about 2 μm.
54. The microfluidic device or yeast cell culture device of any one of 47-53, wherein the daughter cell trapping structure comprises a pair of walls positioned to define a first opening between the two walls and a second opening between the two walls, wherein the first opening is positioned to receive a fluid flow and the second opening is positioned to allow exit of the fluid flow.
55. The microfluidic device or yeast cell culture device of 54, wherein the walls of the daughter cell trapping structure are arcuate, providing a substantially circular trapping structure defining open gates on two sides.
56. The microfluidic device or yeast cell culture device of any one of 54-55, wherein the length of the first and/or the second opening of the daughter cell trapping structure is from about 10 μm to about 20 μm.

57. The microfluidic device or yeast cell culture device of 56, wherein the length of the first and/or the second opening of the daughter cell trapping structure is about 14 μm.
58. The yeast cell culture device of any one of 39-57, further comprising a removable cover configured to mate with the multiwell plate.
59. The yeast cell culture device of 58, wherein the removable cover comprises (i) a first channel in fluid communication with the inlet of each module; (ii) a second channel in fluid communication with the outlet of each module; and (iii) a vacuum-sealing channel.
60. A system comprising the microfluidic device or yeast cell culture device of any one of 38-59 and a camera configured to capture images and/or video of the cell-trapping and observational area.
61. A method of determining replicative age of a yeast cell, comprising:
 (a) culturing one or more DAP yeast strains according to any one of 19-33 in a first culture medium under non-repressed conditions for the conditional promoter;
 (b) culturing the one or more DAP yeast strains from (a) in a second culture medium under repressed conditions for the conditional promoter; and
 (c) counting or quantifying arrested daughter cells produced by the one or more DAP yeast strains to determine replicative age of one or more mother cells of the DAP yeast strain.
62. The method of 61, comprising contacting one or more of the DAP yeast strains with a test compound and determining the effect of the test compound on replicative age of the one or more DAP yeast strains contacted with the compound.
63. The method of 61, comprising, simultaneously with step (a) and/or step (b), introducing a test compound to the culture medium for assessing an effect of the test compound on replicative age of the one or more DAP yeast strains.
64. The method of any one of 61-63, wherein one or both of (a) and (b) are performed in the microfluidic device or yeast cell culture device of any one of 38-60 or using the system of 60, and wherein counting arrested daughter cells produced by the one or more DAP yeast strains to determine replicative age comprises counting arrested daughter cells trapped in the cell-trapping and observational area.
65. A method of determining replicative age of one or more yeast cells, comprising:
 culturing one or more DAP yeast strains according to any one of 19-33 in a first culture medium under non-repressed conditions for the conditional promoter;
 flowing the one or more DAP yeast strains into the plurality of functional modules of the microfluidic device or yeast cell culture device of any one of 38-60 through the inlets;
 entrapping the one or more DAP yeast strains in the arrays of trapping units in the cell-trapping and observational areas;
 culturing the entrapped DAP yeast strains in a second culture medium under repressed conditions for the conditional promoter such that a population of non-dividing daughter cells is produced and entrapped within the array of trapping units in proximity to corresponding mother cells of the DAP yeast strain; and
 counting arrested daughter cells produced by the one or more DAP yeast strains to determine replicative age of one or more mother cells of the DAP yeast strain.
66. The method of 65, comprising imaging mother and daughter cells of the one or more DAP yeast strains prior to the counting.
67. The method of 64 or 65, wherein the mother cells are trapped in the budding-mother cell trapping structures and the budding-mother and arrested-daughter cells produced as a result of budding of a trapped mother cell are trapped in the arrested-daughter cell trapping structures.
68. The method of any one of 61-67, wherein the first culture medium comprises galactose and the second culture medium comprises glucose in place of galactose.
69. A method of screening and identifying compounds that modulate replicative lifespan (RLS), comprising:
 (a) culturing one or more DAP yeast strains according to any one of 19-33 in a first culture medium under non-repressed conditions for the conditional promoter;
 (b) switching the one or more DAP yeast strains to a second culture medium under repressed conditions for the conditional promoter, and for each of the one or more DAP yeast strains under repressed conditions, treating with one or more test compounds;
 (c) counting or quantifying arrested daughter yeast cells to determine replicative age; and
 (d) identifying test compounds that modulate RLS as compared to an untreated control.
70. The method of 69, wherein the one or more test compounds are members of a library of test compounds.
71. The method of 69 or 70, further comprising, after the DAP strains are in the second culture medium under repressed conditions, applying each of the strains to a microfluidic device or yeast cell culture device of any one of 69-70, and imaging arrested daughter yeast cells in the cell-trapping and observational area.
72. The method of any one of 69-71, further comprising, before step (a), barcoding the strains to produce unique strains with individual barcodes.
73. The method of 72, wherein the quantifying comprises sequencing cells with the individual barcodes.
74. A method of screening and identifying mutant yeast strains having an altered/enhanced replicative lifespan (RLS), comprising:
 (a) culturing a library of mutant DAP strains in a first culture medium in one or more multiwell plates under non-repressed conditions for the conditional promoter, where the mutant DAP strains are DAP strains according to any one of 19-33, which further comprise one or more genomic mutations;
 (b) switching the library of mutant DAP strains to a second culture medium under repressed (daughter-arrested) conditions for the conditional promoter;
 (c) applying each member of the library of mutant DAP strains under repressed (daughter-arrested) conditions to a microfluidic device or yeast cell culture device of any one of 38-60;
 (d) counting arrested daughter yeast cells to determine RLS; and
 (e) identifying mutant DAP strains having an altered/enhanced RLS as compared to an unmutated DAP strain control.

75. The method of 74, wherein each member in the library of mutant DAP strains resides in a well of one or more multiwell plates.
76. A method of screening and identifying mutant yeast strains having an altered/enhanced replicative lifespan (RLS), comprising:
(a) culturing a pooled library of mutant DAP strains in a starting liquid culture under non-repressed conditions for the conditional promoter, wherein the mutant DAP strains are DAP strains according to any one of 19-33, which further comprise one or more genomic mutations and a nucleic acid barcode sequence;
(b) switching the pooled library of mutant DAP strains to a second culture medium under repressed, daughter-arrested conditions for the conditional promoter;
(c) aliquoting the pooled library of mutant DAP strains into two or more liquid cultures with equal volume, where each aliquot is allowed to grow for a different length of time ($t_i$, where i=0, . . . N−1), at which time a fixed amount of external reference cells having distinguishing barcodes is added, cells are harvested, DNA extracted and barcodes PCR-amplified with an ith index sequence added; and
(d) pooling together all N sequence samples and performing next generation sequencing to identify mutant yeast strains having an altered/enhanced replicative lifespan (RLS).
77. A method of screening and identifying compounds that modulate replicative lifespan (RLS), comprising:
(a) culturing, under non-repressed conditions for the conditional promoter, a library of wildtype barcoded DAP strains according to any one of 19-33 in one or more multiwell plates, each well containing one member of the library with a unique barcode;
(b) at time $t_0$, transferring and culturing each member of the library to an equivalent well in one or more duplicate multiwell plates under repressed, daughter-arrested conditions for the conditional promoter, where each duplicate plate is allowed to grow for a different length of time ($t_i$, where i=0, . . . N−1), and adding a test compound;
(c) pooling cultures of the ith duplicate for each timepoint i, and adding a fixed amount of external reference cells having distinguishing barcodes;
(d) harvesting, extracting and PCR-amplifying barcodes with an ith index sequence added; and
(e) performing next generation sequencing to identify compounds that modulate RLS.
78. A method of simultaneously measuring the effects on replicative lifespan of $10^2$-$10^3$ mutations and/or compounds/candidate drugs by quantifying barcoded DAP yeast strain daughter cells in liquid culture using next generation sequencing, wherein the DAP yeast strain is a DAP yeast strain according to any one of 19-33.

EXAMPLES

The following examples are put forth so as to provide those of ordinary skill in the art with a complete disclosure and description of how to make and use the present invention, and are not intended to limit the scope of the invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); or sec, second(s); min, minute(s); h or hr, hour(s); aa, amino acid(s); nt, nucleotide (s); i.m., intramuscular (ly); i.p., intraperitoneal (ly); s.c., subcutaneous (ly); and the like.

Materials and Methods

The following materials and methods generally apply to the results presented in the Examples described herein except where noted otherwise.

Part I. Engineering of the Yeast Strain with the Daughter Arresting Program (DAP)

1.1 Constructing pIDS2RH and pIDS2GH Plasmids

TABLE 1

Primers used for constructing pIDS2RH and pIDS2GH plasmids

| Name | Sequence |
|---|---|
| pGAL1-S SacI | 5'-AAC GAG CTC-AGT ACG GAT TAG AAG CCG-3' (SEQ ID NO: 3) |
| pGAL1-A SpeI | 5'-GGT ACT AGT-GTT TTT TCT CCT TGA CGT TAA AGT-3' (SEQ ID NO: 4) |
| GFP-S SpeI | 5'-AAC ACT AGT ACC-ATG AGT AAA GGA GAA GAA CTT TTC-3' (SEQ ID NO: 5) |
| dTomato-S SpeI | 5'-AAC ACT AGT ACC-ATG GTG AGC AAG GGC GAG GAG-3' (SEQ ID NO: 6) |
| gtADH1-A ClaI | 5'-ATC ATC GAT-TCG AGG ACT GCT CTG C-3' (SEQ ID NO: 7) |
| pHO-5S AscI | 5'-TCT GG CGCG CC-ACT GGT GAA ATA GTA GGG AGA ACG-3' (SEQ ID NO: 8) |
| pHO-3A NheI | 5'-CAT GGT GCT AGC-TTT AAA GTA TAG ATA GAA TTG ATT GCT G-3' (SEQ ID NO: 9) |
| GFP-S NheI | 5'-CTA TAC TTT AAA-GCT AGC ACC-ATG AGT AAA GGA GAA GAA CTT TTC-3' (SEQ ID NO: 10) |

TABLE 1-continued

Primers used for constructing pIDS2RH and pIDS2GH plasmids

| Name | Sequence |
|---|---|
| GFP-A | 5'-CTT ATA CAA CTC GTC CAT ACC GTG-TGT AAT CCC AGC AGC TGT TAC-3' (SEQ ID NO: 11) |
| dTomato-S NheI | 5'-CTA TAC TTT AAA-GCT AGC ACC-ATG GTG AGC AAG GGC GAG GAG-3' (SEQ ID NO: 12) |
| dTomato-A | 5'-TTT ATA TAA TTC ATC CAT ACC ATA TAA-GAA CAG GTG GTG GCG G-3' (SEQ ID NO: 13) |
| PMA1-S GFP | 5'-CAC GGT ATG GAC GAG TTG TAT AAG-GGA GGC GGA GGC-ATG ACT GAT ACA TCA TCC-3' (SEQ ID NO: 14) |
| PMA1-S dTomato | 5'-TTA TAT GGT ATG GAT GAA TTA TAT AAA-GGA GGC GGA GGC-ATG ACT GAT ACA TCA TCC-3' (SEQ ID NO: 15) |
| PMA1-A | 5'-TTA GGT TTC CTT TTC GTG TTG-3' (SEQ ID NO: 16) |
| gtADH1-S BclI | 5'-CAA CAC GAA AAG GAA ACC TAA-TGA TCA-GCC CGC TAT TAA CGC-3' (SEQ ID NO: 17) |
| gtADH1-A XmaI | 5'-ATC CCC GGG-TCG AGG ACT GCT CTG C-3' (SEQ ID NO: 18) |
| pFA6a-PMA1-HRS | 5'-ATT GAA AAG AAT AAG AAG ATA AGA AAG ATT TAA TTA TCA AAC AAT ATC AAT ATG-CGA TTT AGG TGA CAC TAT AGA ACG-3' (SEQ ID NO: 19) |
| GFP-PMA1-HRA | 5'-TGA AAC AGA AGA TGC TGA AGA GGA TGA TGA AGA GGA TGA TGT ATC AGT CAT-ACC ACC ACC ACC-TTT GTA TAG TTC ATC CAT GCC ATG-3' (SEQ ID NO: 20) |
| dTomato-PMA1-HRA | 5'-TGA AAC AGA AGA TGC TGA AGA GGA TGA TGA AGA GGA TGA TGT ATC AGT CAT-ACC ACC ACC ACC-CTT GTA CAG CTC GTC CAT GCC-3' (SEQ ID NO: 21) |

Figure 7A:
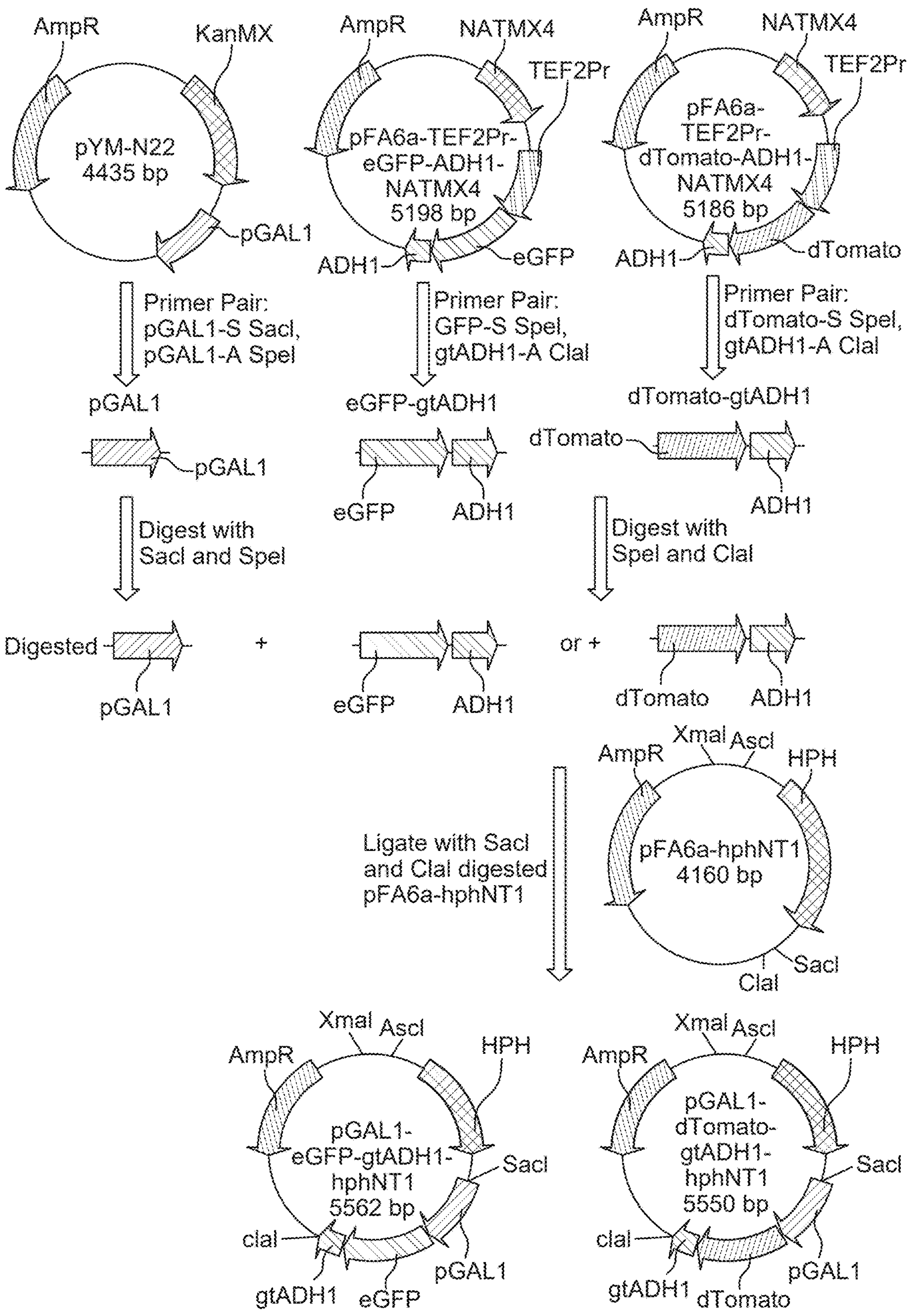
FIGS. 7A-7E depict the steps involved in plasmid construction and genomic integration as used in the DAP system according to an embodiment of the present disclosure.

Step 1: Construction of pGAL1-eGFP-gtADH1-hphNT1 and pGAL1-dTomato-gtADH1-hphNT1 Plasmids A primer pair, pGAL1-S SacI and pGAL1-A SpeI, was used with plasmid pYM-N22 (26) as a template for PCR to amplify GAL1 promoter (pGAL1). A primer pair, GFP-S SpeI and gtADH1-A ClaI, was used with plasmid pFA6a-TEF2Pr-eGFP-ADH1-NATMX4 (19) as a template for PCR to amplify eGFP-gtADH1. A primer pair, dTomato-S SpeI and gtADH1-A ClaI, was used with plasmid pFA6a-TEF2Pr-dTomato-ADH1-NATMX4 (19) as a template for PCR to amplify dTomato-gtADH1. (FIG. 7A).

The PCR product pGAL1 was digested with restriction endonucleases SacI and SpeI. The PCR products eGFP-gtADH1 and dTomato-gtADH1 were digested with restriction endonucleases SpeI and ClaI. The pFA6a-hphNT1 plasmid (26) was digested with restriction endonucleases SacI and ClaI, and the appropriate digested fragments pGAL1, eGFP-gtADH1 and vector pFA6a-hphNT1 were ligated to generate pGAL1-eGFP-gtADH1-hphNT1 plasmid. Similarly, fragments pGAL1, dTomato-gtADH1 and vector pFA6a-hphNT1 were ligated to generate pGAL1-dTomato-gtADH1-hphNT1 plasmid. (FIG. 7A).

Step 2: Constructing pHO-eGFP-PMA1-gtADH1 and pHO-dTomato-PMA1-gtADH1 Inserts

Figure 7B:
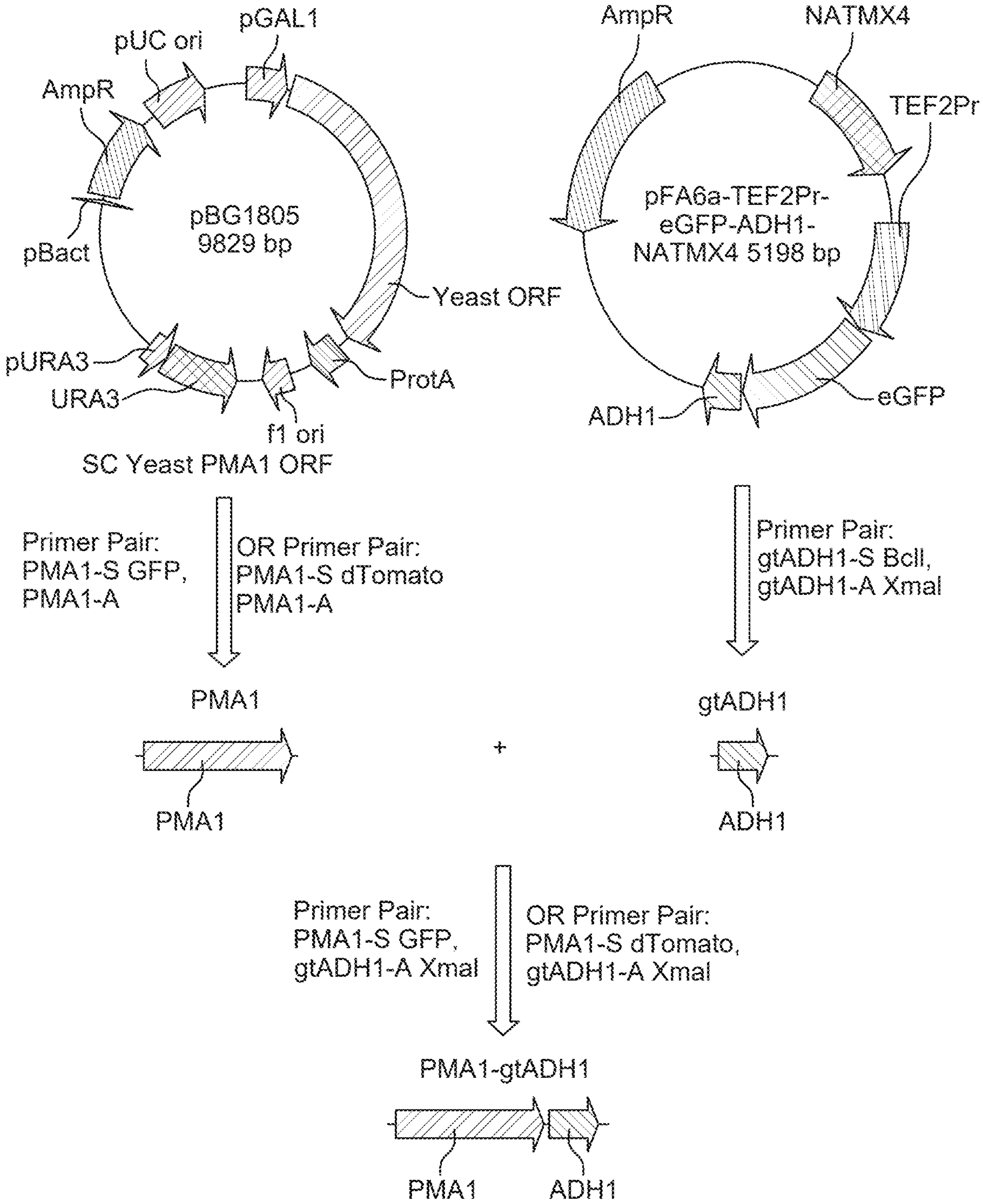
Figure 7C:
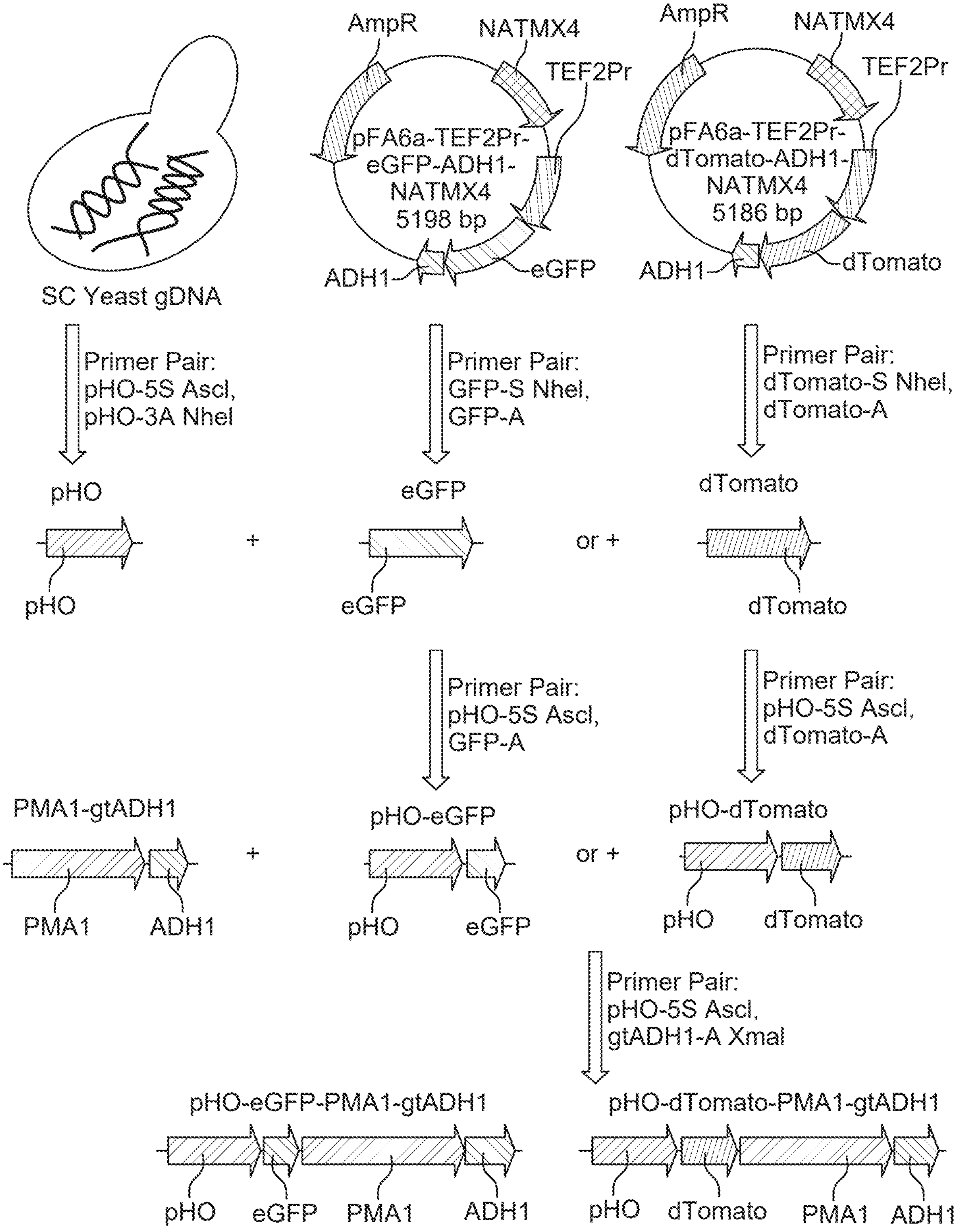

A primer pair, pHO-5S AscI and pHO-3A NheI, was used with *Saccharomyces cerevisiae* yeast genomic DNA as a template for PCR to amplify the promoter of HO gene (pHO). A primer pair, GFP-S NheI and GFP-A, was used with plasmid pFA6a-TEF2Pr-eGFP-ADH1-NATMX4 (19) as template for PCR to amplify eGFP. A primer pair, dTomato-S NheI and dTomato-A, was used with plasmid pFA6a-TEF2Pr-dTomato-ADH1-NATMX4 (19) as template for PCR to amplify dTomato. (FIG. 7C).

A primer pair pHO-5S AscI and GFP-A, and using the PCR-amplified pHO and eGFP DNA products as templates, or primer pair pHO-5S AscI and dTomato, and using the PCR-amplified pHO and dTomato DNA products as templates, were used to generate pHO-eGFP and pHO-dTomato respectively. (FIG. 7C).

A primer pair PMA1-S GFP and PMA1-A, or a primer pair PMA1-S dTomato and PMA1-A, and using a plasmid expressing PMA1 (YGL008C) from yeast ORF collection (Plate 52, A2, Catalog #YSC3868, Open Biosystems) as template for PCR, were used to amplify the PMA1 gene. A primer pair gtADH1-S BclI and gtADH1-A XmaI, and using plasmid pFA6a-TEF2Pr-eGFP-ADH1-NATMX4 (19) as template for PCR, were used to amplify the gtADH1 terminator. (FIG. 7B).

Note: For the following components, mutations were introduced into the 3' ends of eGFP and dTomato, without changing the encoded amino acid sequences. The 3' end of eGFP was modified from CAT GGC ATG GAT GAA CTA TAC AAA GGT GGT GGT GGT (SEQ ID NO: 22) to CAC GGT ATG GAC GAG TTG TAT AAG GGA GGC GGA GGC (SEQ ID NO: 23). The 3' end of dTomato was modified from CTG TAC GGC ATG GAC GAG CTG TAC AAG GGT GGT GGT GGT (SEQ ID NO: 24) to TTA TAT GGT ATG GAT GAA TTA TAT AAA GGA GGC GGA GGC (SEQ ID NO: 25). Using unique primers, it was thereby ensured that the desired full-length PCR products were obtained.

A primer pair, PMA1-S GFP and gtADH1-A XmaI, was used with PCR product pair PMA1 and gtADH1 above as template to run another PCR to generate PMA1-gtADH1. A primer pair, PMA1-dTomato and gtADH1-A XmaI, was used with PCR product pair PMA1 and gtADH1 above as template to run another PCR to generate PMA1-gtADH1. (FIG. 7B).

A primer pair, pHO-5S AscI and gtADH1-A XmaI, was used with PCR product pair pHO-eGFP and PMA1-gtADH1, or pHO-dTomato and PMA1-gtADH1 as a template to run another PCR and amplify pHO-eGFP-PMA1-gtADH1 or pHO-dTomato-PMA1-gtADH1, respectively. (FIG. 7C).

Step 3: Constructing the Final Plasmids pIDS2GH and pIDS2RH

Figure 7D:
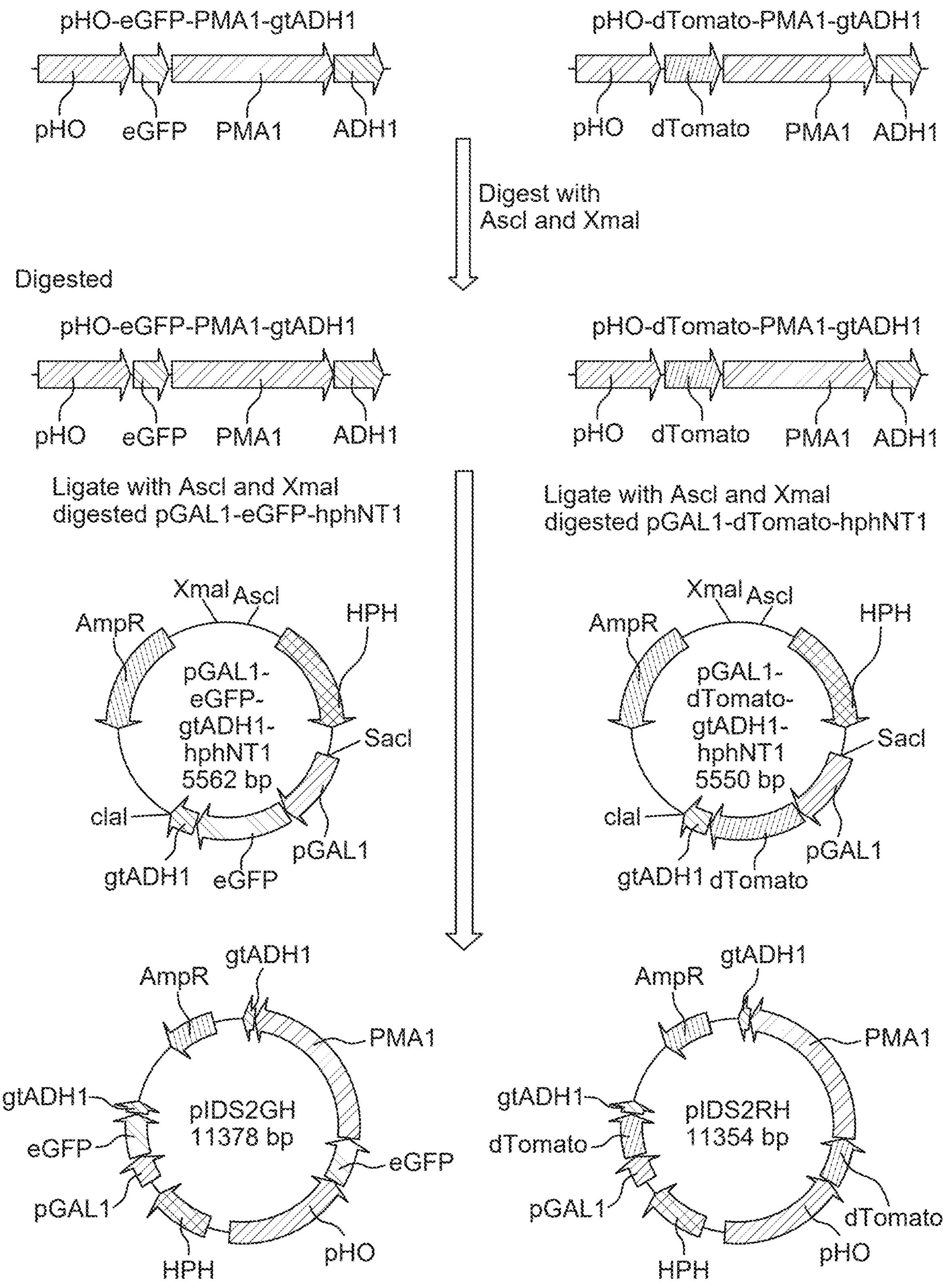

The PCR products above and pGAL1-eGFP-gtADH1-hphNT1 and pGAL1-dTomato-gtADH1-hphNT1 plasmids were digested with restriction endonucleases AscI and XmaI, and the appropriate fragments were ligated to generate pIDS2GH (pFA6a-pHO-eGFP-PMA1-gtADH1 (RC)-hphNT1-pGAL1-eGFP-gtADH1) and pIDS2RH (pFA6a-pHO-dTomato-PMA1-gtADH1 (RC)-hphNT1-pGAL1-dTomato-gtADH1) plasmids, where "RC"=reverse complement. The DNA sequences of the final plasmids pIDS2GH (SEQ ID NO: 1) and pIDS2RH (SEQ ID NO: 2) are set forth in the sequence listing and are illustrated in the drawings submitted herewith. (FIG. 7D).

1.2 Transformation

Figure 7E:
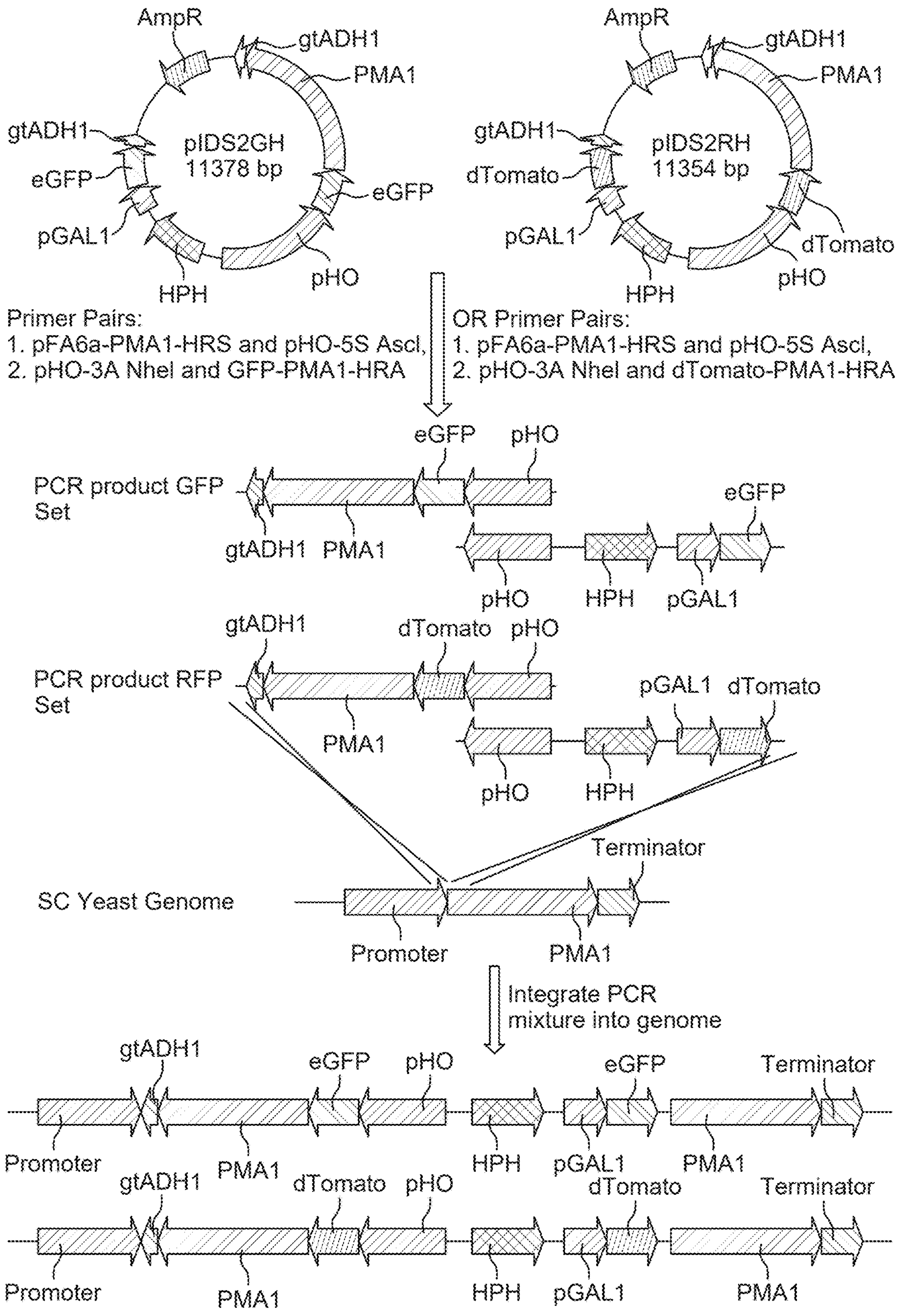
Figure 7F:
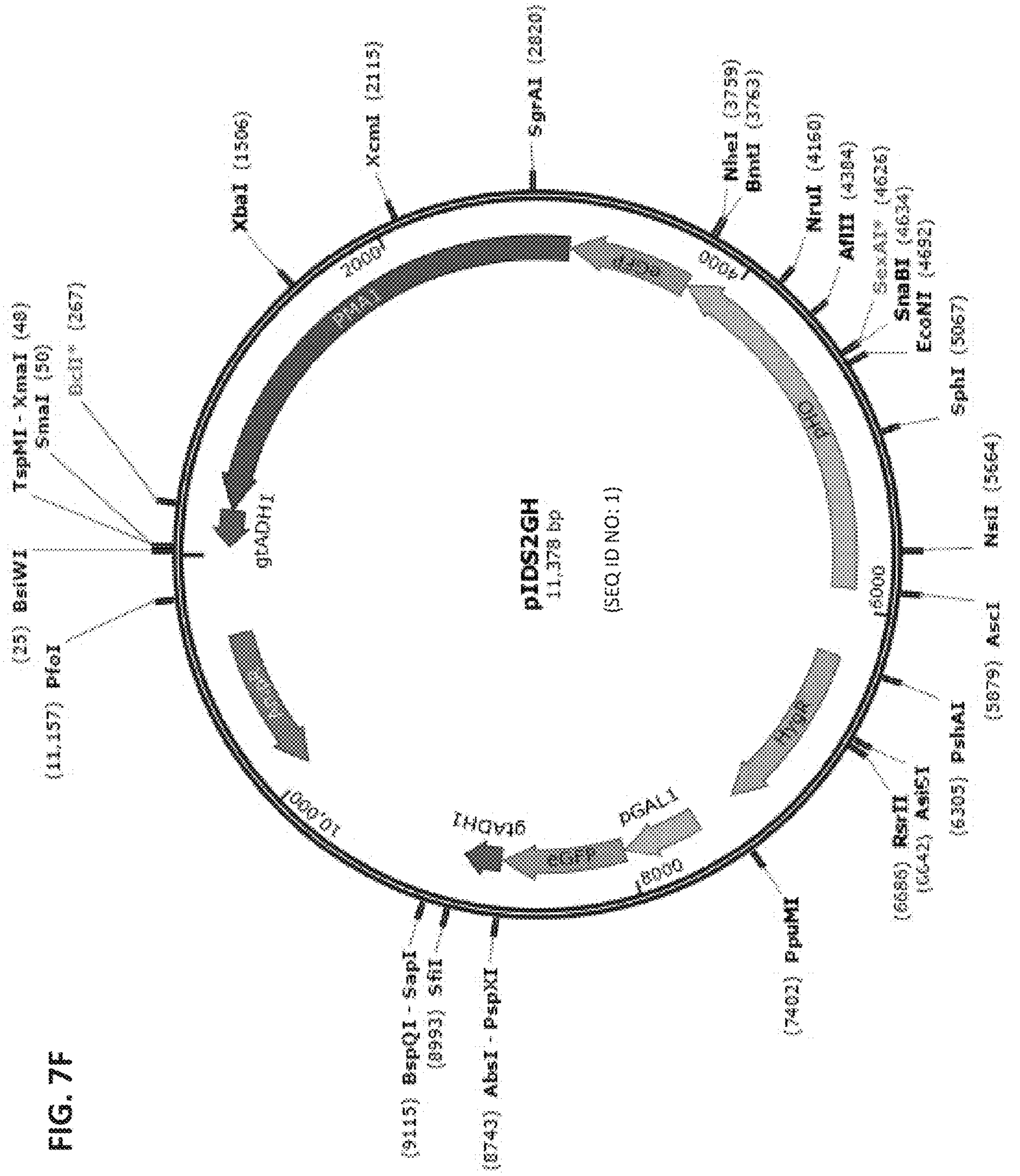
FIGS. 7F and 7G depict the plasmids pIDS2GH (herein identified in the Sequence Listing as SEQ ID NO: 1) and pIDS2RH (herein identified in the Sequence Listing as SEQ ID NO: 2) according to an embodiment of the present disclosure.
Figure 7G:
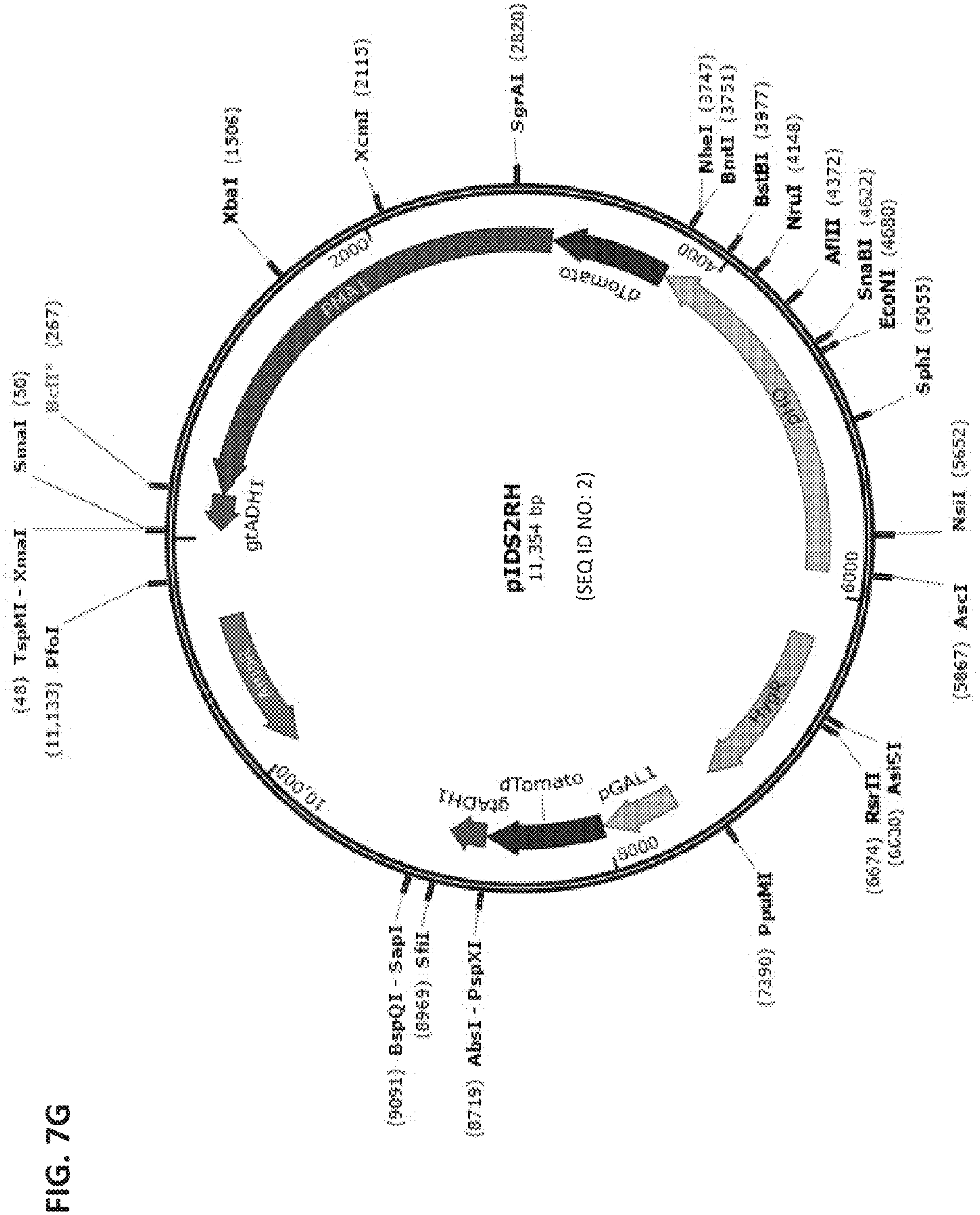

Using plasmid pIDS2GH or pIDS2RH as a template in PCR reactions, primer pair pFA6a-PMA1-HRS and pHO-5S AscI was used to generate the 5' fragment, primer pair pHO-3A NheI and GFP-PMA1-HRA was used to generate the 3' fragment, and primer pair pHO-3A NheI and dTomato-PMA1-HRA was used to generate the 3' fragment. The mixture of appropriate 5' and 3' PCR products was used for the transformation of *Saccharomyces cerevisiae* yeast strains BY4741 (MATα his3Δ1 leu2Δ0 met15Δ0 ura3Δ0) and BY4742 (MATα his3Δ1 leu2Δ0 lys2Δ0 ura3Δ0) (27), resulting in integration of pHO-eGFP-PMA1-gtADH1 (RC)-hphNT1-pGAL1-eGFP or pHO-dTomato-PMA1-gtADH1 (RC)-hphNT1-pGAL1-dTomato into the locus between PMA1 promoter and the start codon (ATG) of the PMA1 gene. Positive colonies were selected on YPAG [BACTO™ yeast extract (DIFCO™ 0127-17) (1%) 10 g, BACTO™ peptone (DIFCO™ 0118-17) (2%) 20 g, Galactose (2%) 20 g, BACTO™ agar (DIFCO™ 0140-01) (2%) 20 g, Adenine sulfate (0.004%) 40 mg in 1 liter medium] plates with 100 μg/ml hygromycin. (FIG. 7E).

Part II. Design and Fabrication of the Microfluidic Device 2.1 Photomask Design Using AutoCAD To trap yeast cells, 16- and 32-channel trapping unit/microstructure arrays were designed to fit a 96-well microplate. Each middle-well within each 3-well module has 20 subarrays, and each subarray is composed of 11 trapping units. In total, there are 220 trapping units in a single microfluidic layer module, for trapping 220 yeast DAP mother cells (see FIGS. 8 through 18). The photomask was designed using commercially available AutoCAD software.

Figure 20:
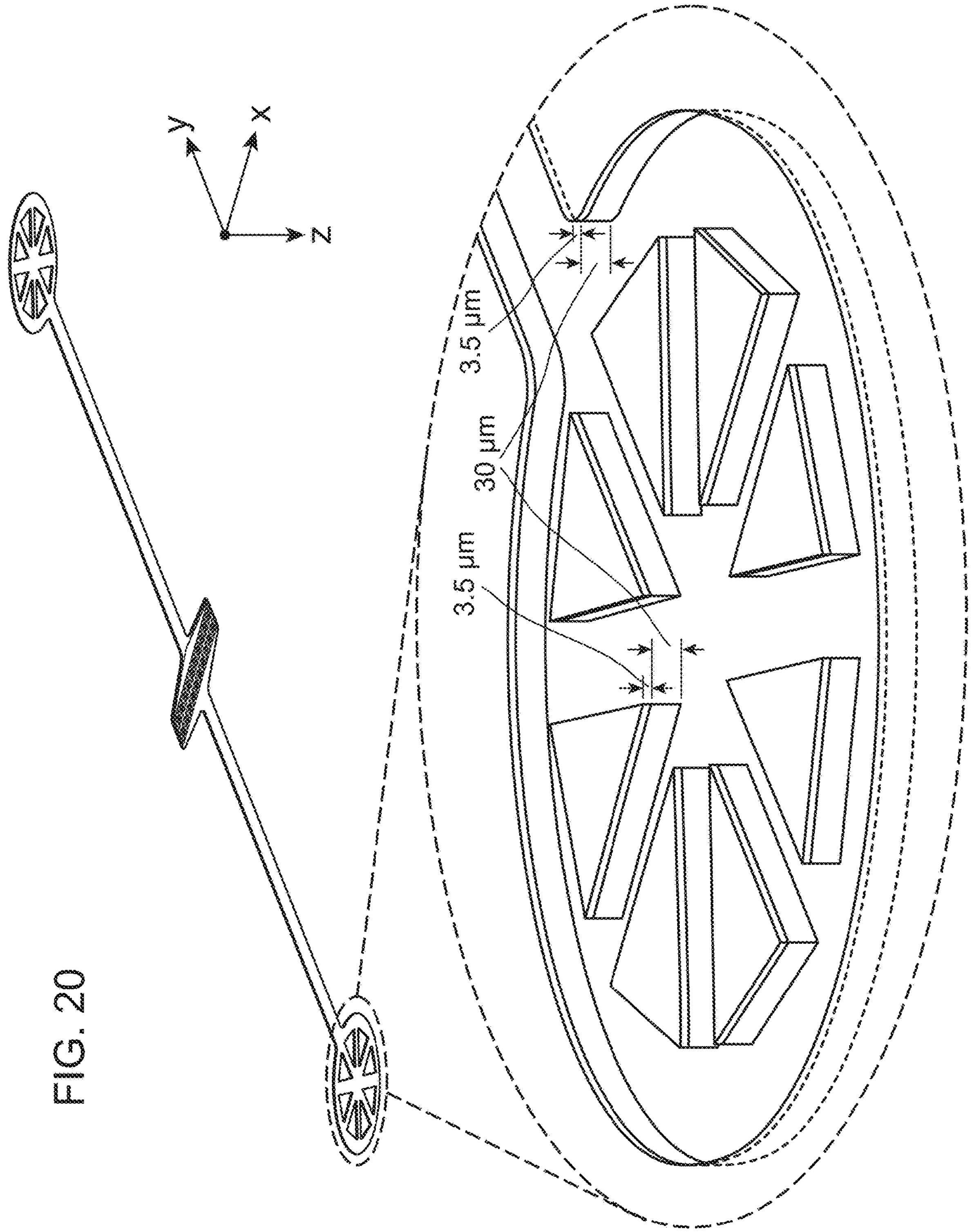
FIGS. 20 and 21: show expanded views of portions of a module including an observational area according to an embodiment of the present disclosure. Exemplary channel depths and microstructure heights are shown.
Figure 21:
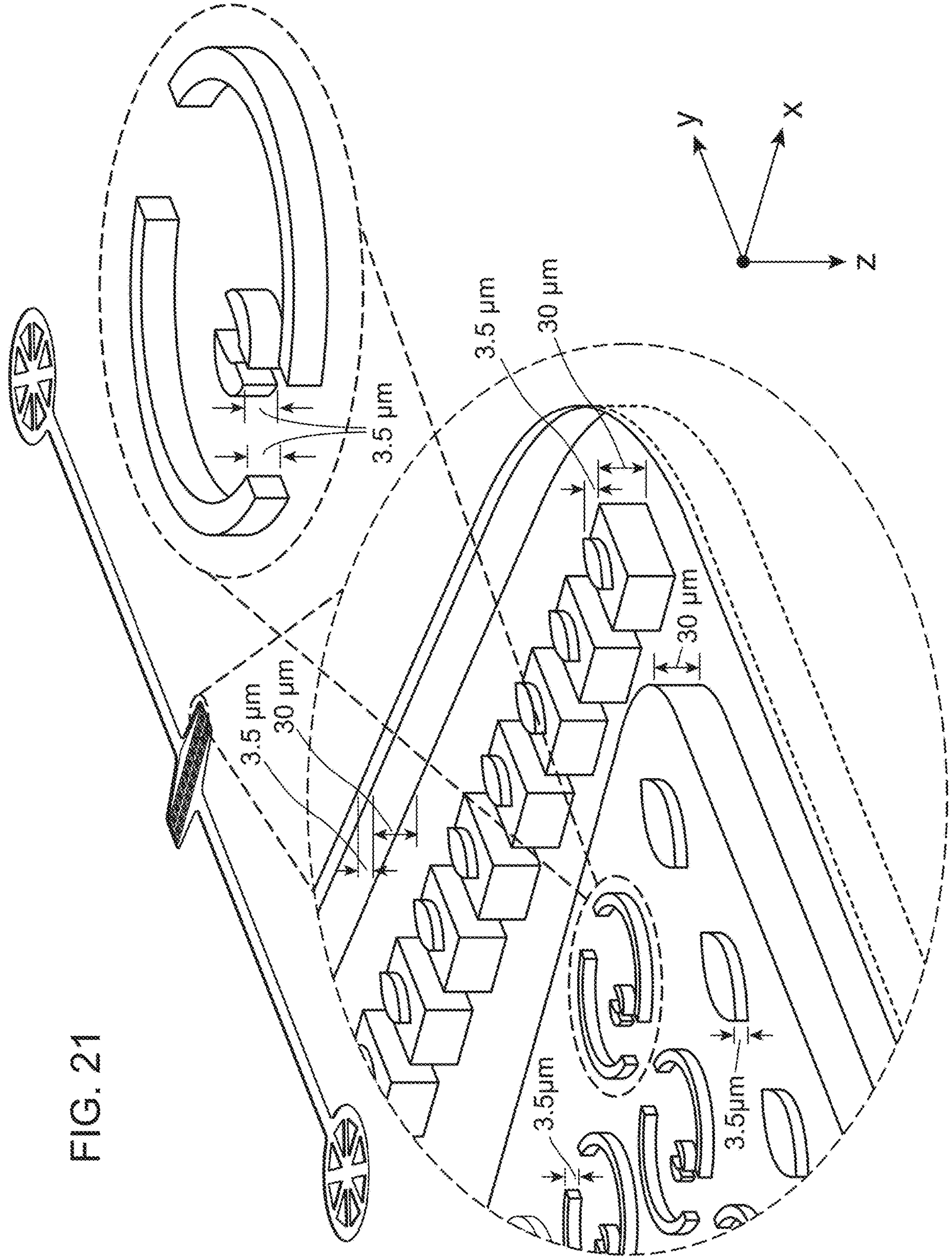

To fabricate the microfluidic device, two photomasks were designed for two-layer UV exposure. The first layer was for the trapping unit with 3.5 μm of the floor-to-top height and the second layer was for a deeper flow channel with 30 μm of the floor-to-top height surrounding the island of the trapping units (FIGS. 20 and 21).

Each module spans 3 wells with the inlet corresponding to one flanking well for entry of fluid media or air pressure to provoke flow into the middle observational area of the microfluidic layer (which corresponds to the middle well) including the cell-trapping units, and then flowing out of the observational area through the outlet corresponding to the other flanking well for media or air flow out. The observational area (corresponding to the middle well) is configured for microscopic observation and allows photographic and/or video recording.

The bottom-most layer, layer 1 of the microfluidic device, is provided on a glass substrate. This layer 1 corresponds to the 32 modules on a 96-well plate, where each module is 18 mm in length (corresponding to 3 wells of the microtiter plate, with 9 mm of space between each well). The trapping units are in the observational area in the middle wells of each module, and each middle well has 20 positions for observation×11 trapping units (the 20 positions in an array measuring 2292.3 μm, and shown in FIGS. 16, 17). The trapping units on this bottom-most layer 1 trap single DAP mother cells as they flow into the middle well of the device.

Layer 2 (above layer 1 in the device); layer 2 increases the depth of the microfluidic device and has inlet-side channels connecting the inlet wells to the observational area in layer 1 (corresponding to the middle well of each module), as well as outlet-side channels connecting each observational area in layer 1 to the outlets. A 96-well plate is positioned between the cover and layer 2. The trapping units of layer 1 are 3.5 μm high, and the depth of layer 1 is not affected by layer 2. The depth of layer 2 is 30 μm, so the depth of the main and side flow channels (inlet-side and outlet-side channels connecting to the cell-trapping and observation area bearing the trapping units) is 3.5 μm trapping units floor-to-top height+30 μm second layer floor-to-top height for deeper flow channel=33.5 μm height of layers 1 and 2 together (FIGS. 20, 21).

Figure 19:
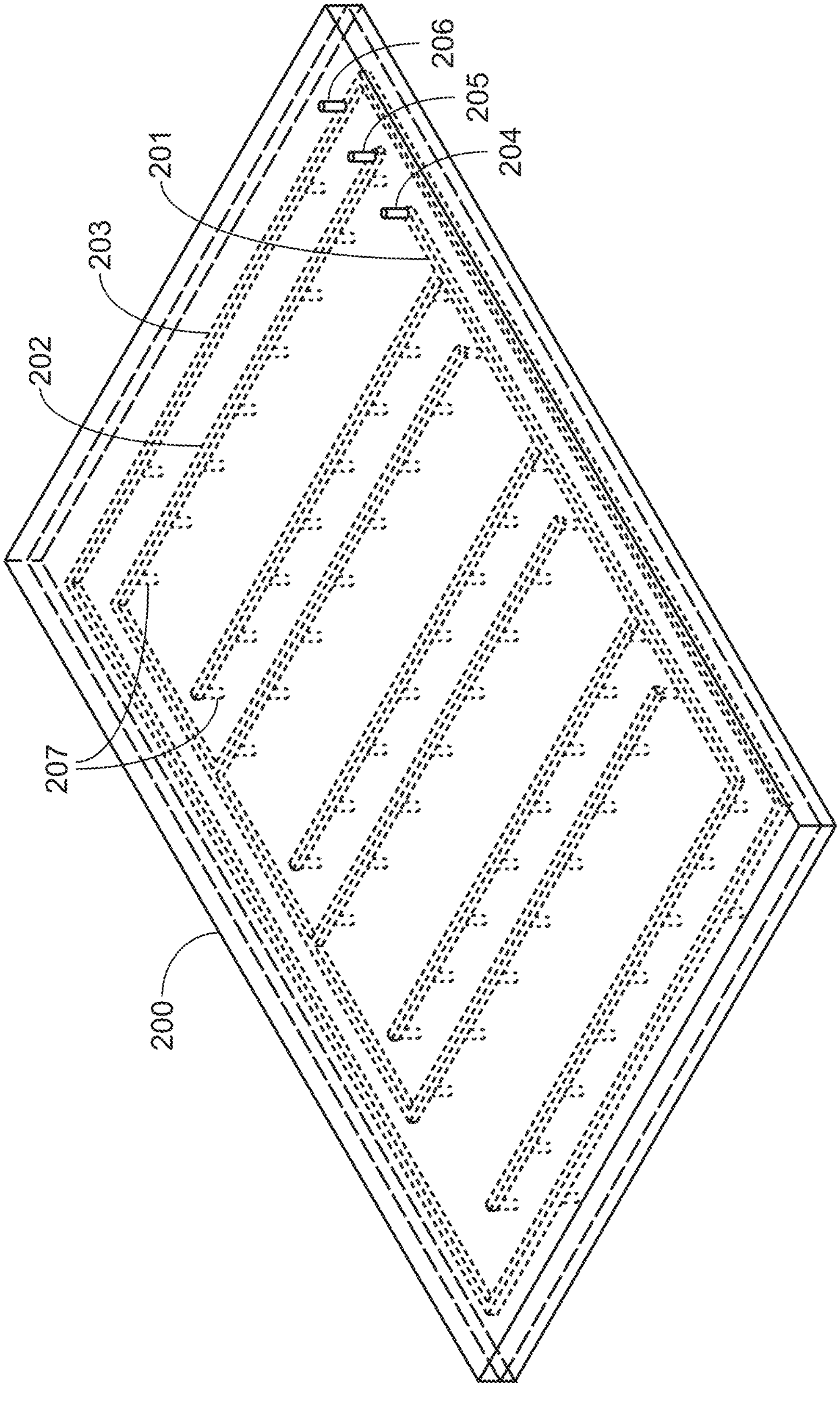
FIG. 19: shows a cover which may be used in connection with a yeast cell culture device as described herein according to an embodiment of the present disclosure.

Using the labeling of a 96-well plate shown in FIG. 2A, with rows labeled A through H and columns labeled 1 through 12, the cover is illustrated (FIGS. 10A and 10B). The cover is positioned on top of the multiwell plate and a vacuum is applied through the vacuum hole to allow a tight seal. The cover allows fluid (e.g., media) or air pressure to be added using a loading hole. Thus, the added fluid or air can move through channels from the loading hole, and these channels are in fluid communication with the inlets of several modules. When fluid or air pressure is added, a directional flow through the microfluidic layer is created, such that the flow is into inlets, through inlet-side channels connecting inlets to the middle cell-trapping and observational area of the modules, and then flowing out through outlet-side channels through outlets and finally through a vent hole in the cover. In some embodiments, the cover has three layers: the bottom layer of the cover is 1 mm in height, the middle layer of the cover is 1 mm in height with inlet-side and outlet-side flow channels each 1 mm in length), and the top layer of the cover is 3 mm thick, and the holes into the channels of the cover are cylindrical with 1 mm diameter (FIG. 19).

As illustrated in FIGS. 10A and 10B, the cover has four columnar inlet channels in fluid connection with the loading hole in the cover, wherein the four columnar inlet channels allow fluid to enter wells in columns 1, 4, 7 and 10 of the 96-well plate. The cover also has four columnar outlet channels in fluid connection with the vent hole in the cover, wherein the four columnar outlet channels allow fluid to exit the wells in columns 3, 6, 9 and 12 of the 96-well plate.

2.2 3D Printing of 32-Channel Cover

To wash cells, and/or to fill the microfluidic device with water or cell culture media (with or without a test compound/drug), a 32-module cover with three flow channels was designed: (1) a vacuum sealing channel, (2) a loading channel (for inflow; with vent holes in wells in columns 1, 4, 7, 10), and (3) an outflow channel (with vent holes in wells in columns 3, 6, 9, 12) (FIGS. 10A, 10B and 19). The 3D structure of the cover was designed with AutoCAD and was fabricated by 3D printing. The side of the cover facing the multiwell plate and having channel vent holes is covered by a soft, transparent PDMS gel with holes at appropriate positions, which can help seal the cover and the multiwell plate by applying vacuum.

2.3 Fabrication of the Mold

The wafer was baked at 200 °C for 5 minutes to evaporate water vapor, followed by cooling down at room temperature for 5 minutes. For the first layer, 4 ml of SU-8 3005 was dispensed on a 4-inch silicon wafer (for 16-channel) or 5 ml of SU-8 3005 was dispensed on a 5-inch silicon wafer (for 32-channel), and centrifuged at 500 rpm for 10 seconds with acceleration of 100 rpm/second, then at 5000 rpm for 30 seconds with acceleration of 300 rpm/second. The coated wafer was then baked at 60 °C for 3 minutes, followed by baking at 95 °C for 3 minutes, then cooled at room temperature for 5 minutes.

The SU-8 3005 photoresist was exposed to UV light of 12.7 $mW/cm^2$ 365 nm for 2 seconds, followed by baking at 60 °C for 3 minutes and 95 °C for 3 minutes, then cooled at room temperature for 5 minutes.

For the second layer, 4 ml of SU-8 2015 was dispensed on a 4-inch silicon wafer (for 16-channel) or 5 ml of SU-8 2015 was dispensed on a 5-inch wafer (for 32-channel), centrifuged at 500 rpm for 10 seconds with acceleration of 100 rpm/second, then at 1500 rpm for 30 seconds with acceleration of 300 rpm/second. Bake the coated wafer at 60 °C for 5 minutes, followed by baking at 95 °C for 5 minutes, then cooled at room temperature for 5 minutes.

The second layer photomask was aligned with the first layer alignment marks, and the photoresist exposed under 12.7 $mW/cm^2$ 365 nm UV light for 12 seconds, followed by baking at 60 °C for 5 minutes and 95 °C for 5 minutes, then cooled at room temperature for 5 minutes.

The UV exposed photoresist was developed in SU-8 developer with gentle shaking for 5 minutes, and the developed image spray-washed with fresh developer solution for approximately 3×10 seconds, followed by a second spray/wash with Isopropyl Alcohol (IPA) for another 3×10 seconds. The image was air dried with filtered, pressurized air or nitrogen. The imaged resist was baked at 200 °C for 30 minutes, then cooled at room temperature for 5 minutes.

2.4 Fabrication of the Microfluidic Device

The silicon wafer mold was immobilized on a 15 cm-diameter plastic Petri dish using scotch tape, with the pattern side facing up. Each mold can be re-used many times to fabricate microfluidic devices.

A clean weighing boat was placed on a balance and the balance tared. 50 g of PDMS base was poured into the weigh boat, and 5 g of PDMS curing agent was then added to the weigh boat (w/w ratio of 1:10 to the PDMS base). This volume was based on a 15 cm-diameter Petri dish with the mold (the amount of reagent is adjusted if a different size Petri dish is to be used).

The PDMS base and the curing agent were stirred with a disposable pipette, starting from the edge of the weighing boat and slowly moving inwards. For PDMS polymerization, the mixture was stirred thoroughly for several minutes until small bubbles formed throughout.

The mixture was poured slowly into the Petri dish to completely cover the silicon wafer mold. The Petri dish was then placed in a vacuum for 30 minutes to remove all the air bubbles from the PDMS mixture. If bubbles remain on the surface of the mixture, a pipette was used to blow them out.

The silicon wafer mold filled with PDMS was incubated in an oven at 70 °C for about 2 hours, then cooled at room temperature for 30 minutes, and the PDMS cut directly from the silicon wafer mold leaving a minimum 5-mm margin around the pattern using a single-edge industrial razor blade, and the PDMS layer gently peeled off the wafer mold, being careful to avoid any damage to the construction of the wafer mold.

The PDMS layer was placed on the cutting pad with the pattern side facing up, and a punch pen (1.2 mm I.D.) used to punch holes through the inlet and outlet circles on each side of the channels. The punched holes created the pathway for the flow of medium. The holes through the inlet and outlet circles were confirmed to completely perforate the PDMS layer, and the PDMS columns were removed from the hole.

Every punched hole was checked for complete penetration by inserting the punch pen needle again into the hole. The needle should come out the other side, indicating that there is no blockage in the pathway being created. Tape was applied to the pattern surface, and then gently peeled off to remove dust particles, and this step was performed at least three times. A clean piece of scotch tape was left on the PDMS to maintain sterility. The same procedure was repeated on the opposite side of the PDMS and the last piece of tape let on this opposite side as well.

A 50×75 mm (for 16-channel) or 105×75 mm (for 32-channel) cover glass with a thickness of 0.13-0.17 mm was prepared by spraying 70% ethanol on the glass and drying with dust remover to clean the surface. Additionally, the glass can be washed with sterile water and dried with dust remover.

The cover glass and PDMS was transferred to a plastic plate, and the scotch tape removed from the PDMS. The PDMS was placed with the pattern side facing up, while avoiding any contact with the pattern surface during transfer.

The plastic plate was placed in the plasma machine. Oxygen plasma treatment was applied to the PDMS and the cover glass to render the surfaces hydrophilic with the following operation parameters: exposure, 90 seconds; gas stabilization, 20 cc/min; pressure, 200 mTorr; and power, 100 W.

The PDMS was carefully aligned and placed onto the cover glass, connecting both hydrophilic surfaces (the surfaces that faced up during the plasma treatment), ensuring that there were no air bubbles between the PDMS and the cover glass. The PDMS microfluidic device was incubated in an oven at 70 °C for at least 2 h. The bond between the PDMS and the cover glass was confirmed by slightly lifting the PDMS from the edges with tweezers; a successful bond will not separate the PDMS from the cover glass by this lifting.

2.5 Assembly of Microfluidic Device and Multiwell Plates

Holes were drilled with a 2 mm diameter drill bit at columns 1, 3, 4, 6, 7, 9, 10, 12 in a 96-well flat bottom polystyrene microtiter plate (see FIG. 9). The plate was washed with double distilled water to remove the plastic debris and dried at 70 °C for 30 minutes.

The bottom surface of the plate and the PDMS surface opposite to the cover glass on the chip were cleaned once with scotch tape. Oxygen plasma treatment was applied to the PDMS and the bottom surface of the plate to render the surfaces hydrophilic with the following operation parameters: exposure, 90 seconds; gas stabilization, 20 cc/min; pressure, 200 mTorr; and power, 100 W.

Two layers of kimwipe tissues were placed on the plate bottom surface. 3 ml 1% APTMS [(3-Aminopropyl)

trimethoxysilane] aqueous solution was evenly added on the tissue and the air bubble between the surface and the tissue was removed, followed by incubation at room temperate for 30 minutes.

3 ml 1% GOTMS [(3-Glycidyloxypropyl)trimethoxysilane] aqueous solution was evenly added on the PDMS surface, followed by incubation at room temperate for 30 minutes.

The excess APTMS or GOTMS aqueous solution was removed, the plate bottom and the PDMS surface were washed with double distilled water, and the remaining water was removed with the dust remover, followed by drying them at 37 °C for 30 minutes.

The PDMS surface was aligned and attached on the plate bottom, and the PDMS was gently pressed around the edge of the bottom to form a sealed environment. The plate was sealed with the 32-channel cover and vacuum applied to remove the air between the PDMS and the surface of the plate bottom, keeping the bonding at room temperature for 30 minutes, to tightly attach the microfluidic layer to the bottom of the multiwell plate. The vacuum was then released.

300 μl autoclaved double-distilled water was added to the wells in columns 1, 4, 7, 10, and the plate was sealed with the 32-channel cover by applying vacuum to the sealing channel. The microfluidic channels were filled with water by applying 2 psi air pressure to the loading channel for 240 seconds, and 200 μl autoclaved double-distilled water was added to the wells in columns 3, 6, 9, 12. The lid of the 96-well plate was then placed on the microfluidic plate, which was then left at room temperature overnight. At this point, the plate is ready for the use. In the meanwhile, the microfluidic layer is stored filled with water to help prevent the channels from collapsing.

Part III. High Throughput Measurements of Replicative Lifespan 3.1 Lifespan Measurement Using the Microfluidic Device and Microscope The IDS2GH or IDS2RH transformed yeast cells were cultured in YEPG [For 1 L medium: BACTO™ yeast extract (DIFCO™ 0127-17) (1%) 10 g, BACTO™ peptone (DIFCO™ 0118-17) (2%) 20 g, Galactose (2%) 20 g] at 30 °C for 15 hours, after which time the cells were diluted 1:20 in fresh YEPG and grown for another 3 hours. The cells were centrifuged and washed 3 times with YEP [For 1 L medium: BACTO™ yeast extract (DIFCO™ 0127-17) (1%) 10 g, BACTO™ peptone (DIFCO™ 0118-17) (2%) 20 g]. Finally, the cells were resuspended in an equal volume of YEP, then diluted at a 1:5 ratio in fresh YEP and incubated at 30 °C for another 3 hours; this last step allowed separation of any aggregates of cells.

The water in the wells was discarded, and 100 μl of cells (~$1\times10^6$ cells/ml) were loaded into inlet wells in columns 1, 4, 7, 10 of the multiwell plate. The plate was then sealed with the 32-channel cover by applying vacuum to the sealing channel, and cell flow started by applying 4 psi air pressure to the loading channel for 10 seconds. Any remaining cells in the wells are discarded, and 300 μl autoclaved ddH2O added to wash the cells, applying 25 psi air pressure to the loading channel for 10 seconds. The remaining water in the wells was again discarded, and 300 μl YEPD [For 1 L medium: BACTO™ yeast extract (DIFCO™ 0127-17) (1%) 10 g, BACTO™ peptone (DIFCO™ 0118-17) (2%) 20 g, Dextrose (2%) 20 g] added, and the cells were washed by applying 2 psi air pressure to the loading channel for 240 seconds. The remaining YEPD in the wells was discarded and 300 μl fresh YEPD added to each well in columns 1, 3, 4, 6, 7, 9, 10, 12. For drug screening, cells were washed and cultured by adding YEPD with appropriate concentration of drug, and the plate incubated with loaded cells at 30 °C overnight.

Images were captured after the cells were incubated for 84 hours, and images were uploaded to the server for next-step analysis. The dTomato signals were used for counting initial mother cells and the bright-field signals were used for counting total cell number. To calculate replicative life span (RLS), the trapping units having multiple mother cells in one circular capture region were discarded and thus, for one selected yeast daughter-arrested mother cell, the RLS=total cell number in the circle−1.

3.2 Lifespan Measurement Using Multiplexed Barcode Sequencing

The lifespan of deletion mutants was measured by pooling together deletion strains with barcodes and counting the number of cells for each strain by sequencing the barcodes after the cell culture was grown for a fixed amount of time. At the beginning of the experiment, media was switched from galactose to glucose media (DAP program on, daughters arrested), and the culture was partitioned into N identical aliquots with equal volume. Each aliquot was grown for a different time, at which point a fixed amount of external reference cells with distinguishing bar codes was added, cells were harvested and genomic DNAs were extracted. PCR barcodes were then amplified, with an index sequence added to the sample from each time point. All the N sequence samples were then pooled together for next generation sequencing. The external reference cells with distinguishing bar codes were used to normalize out the variability due to cell harvesting, DNA extraction, and PCR amplification. The replicative lifespan was then calculated for each barcoded stain as described above.

Results

Figure 1B:
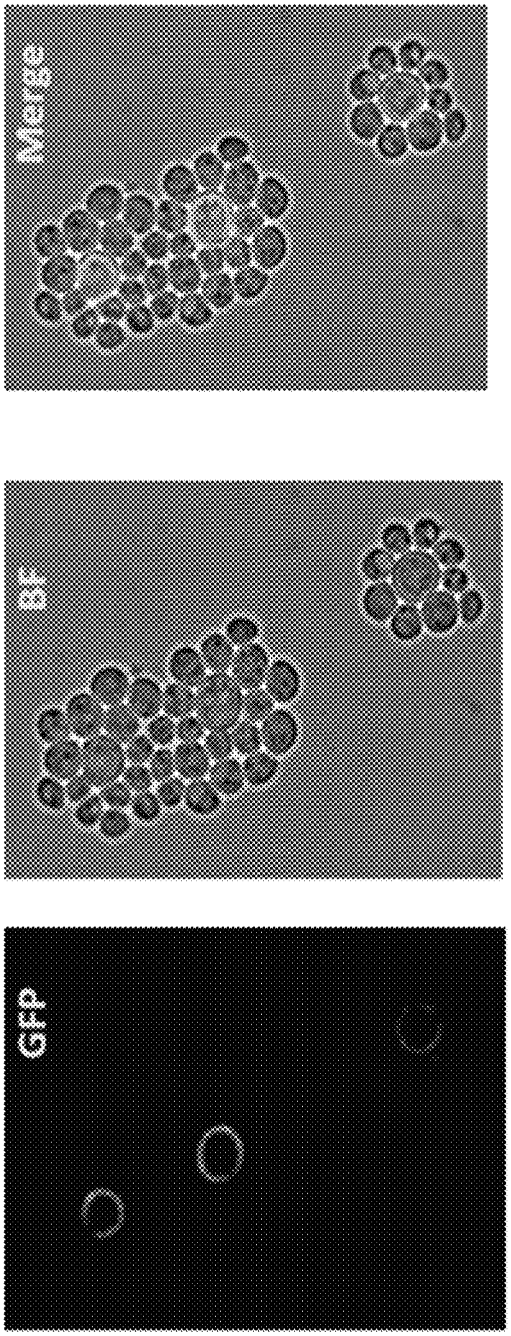
FIG. 1B depicts GFP-tagged plasma membrane protein expressed in mother cells but not in arrested daughter cells according to an embodiment of the present disclosure.
Figure 1C:
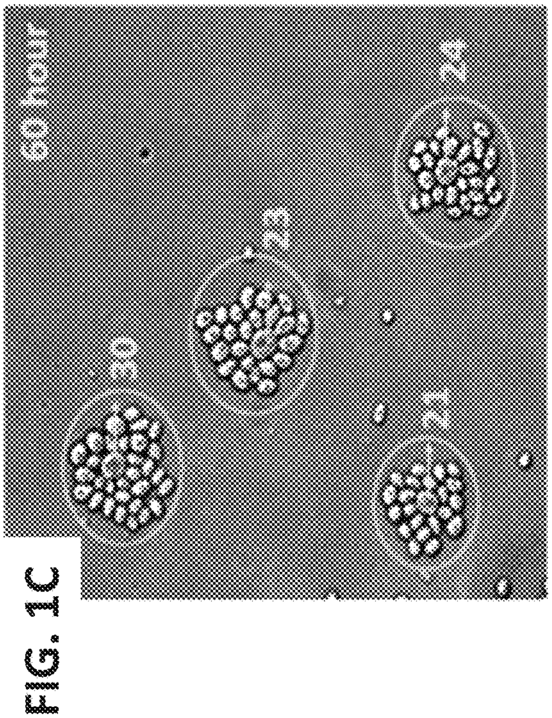
FIG. 1C shows microcolonies having a mother cell surrounded by 21, 23, 24 and 30 arrested daughter cells, indicating the replicative lifespan (RLS) for each mother cell in a microcolony according to an embodiment of the present disclosure.

Example 1: Development of the Daughter Arresting Program (DAP) that Enables High-Throughput Lifespan Measurement Utilizing the power of yeast genetics, an exemplary daughter-arresting-program (DAP) was developed in which, upon switching actively dividing yeast cells from galactose media to glucose media nearly immediately arrests daughter cells and prevents them from budding while leaving the mother cell budding process unaffected (see FIG. 1A for the genetic construct). When growing on a plate (e.g., a multiwell, microtiter plate), the DAP allows the measurement of lifespan by counting the number of arrested daughter cells surrounding a mother cell in a micro-colony (FIG. 1C).

As shown in FIG. 1A and described below, the exemplary daughter arresting program (DAP) system uses a single genetic construct integrated into a genomic locus: a glucose-repressible promoter replacing the native promoter of the essential gene PMA1—encoding an abundant plasma membrane-anchored protein that acts as a proton pump and belonging to a widespread family of cation transporters known as the $P_2$-type ATPases—fused in-frame with a fluorescent tag. The construct also contains a mother-specific promoter (HO promoter) driving transcription of PMA1 in the opposite direction (FIG. 1A). When cells are cultured in galactose media, Pma1 protein is expressed and localized to the cell membrane. After switching to glucose media, expression of PMA1 is repressed, and the Pma1 protein is no longer produced in the daughter cells. However, at the time of the switch, the existing mother cells have Pma1 protein on their membranes and can still maintain normal function (Pma1 is a long-lived protein). Mother cells continue to express PMA1 from the HO promoter to maintain a normal level throughout their lifespan. Daughter cells produced after the switch will not inherit Pma1 protein from their mothers due to the fact that daughter cells do not inherit plasma membrane from their mothers (FIG. 1B); thus, cell division arrests in the daughter cells. The arrest of daughter cell division was found to be clean and nearly immediate. Employing the DAP system in different genetic backgrounds and under different nutrient conditions, thousands of mother cells, and thus more than $10^4$ daughter cells, have been assayed and analyzed (data not shown); no leakiness (i.e., daughter cell divisions) was observed. Therefore, the rate of the suppressor mutations can be estimated at $<10^{-4}$ per cell division, indicating that the system is very robust.

As shown in FIG. 1A, an essential gene (PMA1) whose protein product localizes to the cell membrane is placed under the control of a glucose repressible promoter (pGAL1). (FIG. 1B) Upon switching media from galactose to glucose, the expression of PMA1 (tagged with GFP) is turned off. Mother cells already have the protein in their cell membrane while newly budded daughter cells do not inherit this protein due to asymmetric cell division. (FIG. 1C) Micro-colonies with mother cells surrounded by their daughters. The numbers indicate the number of daughter cells. (FIG. 1D) Replicative life spans of WT, fob1Δ, sir2Δ measured by using the DAP cells.

The nucleic acid construct used to produce the exemplary DAP yeast strain has two expression cassettes. The first includes a glucose repressible promoter and a fluorescent tag (pGAL1-eGFP/dTomato). The second includes a mother-specific promoter, a copy of the PMA1 gene, and a fluorescent tag (pHO-eGFP/dTomato-PMA1-gtADH1). Other parts: HygR (hygromycin resistance; "hphNT1") gene for selection of yeast transformants, AmpR for *E. coli* selection. After PCR and transformation, the whole DNA, consisting of part one-HygR-part two, i.e., from 5' to 3', gtADH1-PMA1-eGFP/dTomato-pHO (reverse complimentary sequence)-HygR-pGAL1-eGFP/dTomato is integrated into the genome between the endogenous PMA1 promoter and the start codon (ATG) of PMA1. Therefore, upon integration, both copies of PMA1 are fused with eGFP/dTomato, one is regulated by yeast GAL1 promoter—a glucose repressible promoter, the other is regulated by yeast HO promoter—a mother specific promoter. PMA1 is an essential gene which encodes a plasma membrane $P_2$-type $H^+$-ATPase, a major regulator of cytoplasmic pH and plasma membrane potential. The Pma1 protein is long-lived and distributed in the plasma membrane. When cells are cultured in galactose media, GAL1 promoter is turned on and eGFP/dTomato-Pma1 is expressed and localized to the cell membrane; cells grow and bud normally. After switching to glucose media, eGFP/dTomato-Pma1 expression is repressed, and the protein is no longer produced in the daughter cells, and the daughter cells do not inherit eGFP/dTomato-PMA1 from mother cells. In contrast, the existing mother cells at the time of the media switch have long-lived Pma1 protein on their membranes and still maintain normal budding/division. Mother cells also maintain a normal level of Pma1 protein expressed throughout their lifespan via the mother-specific HO promoter. Daughter cells produced after the media switch do not inherit plasma membrane (and therefore Pma1 protein) from their mothers due to asymmetric cell division (FIG. 1B) and because the PMA1 gene is essential for viability, cell division stops immediately in the daughter cells. The fused eGFP/dTomato was found to enhance the asymmetrical distribution and block the inheritance of PMA1 in daughter cells.

Figure 1D:
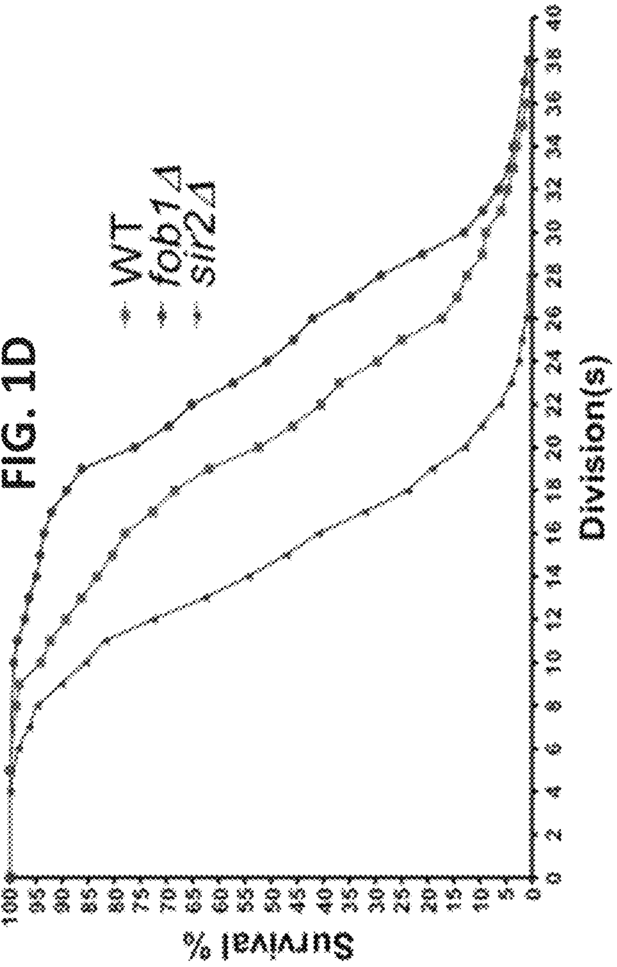
FIG. 1D compares the RLS of wildtype (WT), fob1Δ and sir2Δ mutants, as measured in the DAP strain according to an embodiment of the present disclosure.

The DAP construct does not affect the lifespan of the mother cells, i.e., wild type cells with or without DAP construct integrated into their genome have the same lifespan, and by using DAP strains, long- and short-lived mutations have been correctly identified (FIG. 1D).

Two other genes encoding membrane proteins, VHT1, encoding a high-affinity plasma membrane $H^+$-biotin (vitamin H) symporter, and SLN1, a transmembrane histidine phosphotransfer kinase and osmosensor that regulates the MAP kinase cascade, were tested for their performance in the DAP system, but were found to be unsuitable (data not shown).

Example 2: Development of a High Throughput Microfluidic Device that Utilizes DAP for High-Throughput Molecular Phenotyping and Lifespan Assay A newly conceived and designed microfluidic device was engineered employing the DAP construct, in conjunction with a new concept for parallelization; thus, a high throughput device was developed for reporter analysis and RLS assays, that is robust and easy to operate (FIG. 2A). The device contains a 96-well microtiter plate interfacing with a microfluidic layer including an array of modules. Each module encompasses the equivalent of three wells on the microtiter plate, and has an inlet and an outlet flanking (and in fluid communication with) an observational area aligned with the middle well of each 3-well-sized module. The observational area in between the inlet and outlet of each module allows a microscope objective to view the cell-trapping microstructures/units. This design combines the advantages of using 1) a standard 96-well plate which can be automated for liquid/cell culture handling, with 2) a microfluidic device's ability to trap DAP mother cells within trapping units, and 3) long term time-lapse imaging through the observational area. Because of the modular design, each module (including the inlet, observational area and outlet) and the components (e.g., the multiwell plate, microfluidic layer, observational area and an optional cover) can be changed to optimize the modules for specific tasks.

In general, cells or strains (either wild type or mutant libraries) are cultured in one or more multiwell plate(s). For testing, screening and identifying compounds effective in modulating replicative lifespan (RLS), a library of compounds may also be stored in one or more multiwell plates. Thus, a multichannel pipette or liquid handling robot can be used to transfer or load cells or compounds into the device described herein, and/or media (with or without drug compounds to be tested) may be added to the modules in the microfluidic layer.

After loading cells or strains into the multiwell plate(s), the cover is put into place and used to apply compressed air to push the cells to flow through channels and modules in the device, allowing DAP mother cells to be trapped in the trapping units in the modules of the microfluidic layer. The cover is then removed and the remaining water discarded, and appropriate media is added. The cover and compressed air can be used to wash cells, such that pressure causes air or other fluid (e.g., media) to flow through the modules. A microscope may be employed to view the observational area of the microfluidic device. After washing cells, the appropriate media is then add to the device (for example, for each module, corresponding to the wells of a multiwell plate which can be integrated into the device, two wells flank each middle well of a 3-well module, and these flanking wells have inlet-side and outlet-side channels for fluid to flow into and out of the module).

After incubating at 30 °C for 84 hours, the programmed image software can be used to automatically take images. Software may be used to automatically gather and analyze data, and to calculate the life span results after the images are uploaded to a server or other (digital or analog) storage medium.

Example 3: Mutants and Drug Screening Using the DAP and the High Throughput Microfluidic Device Using the DAP system and the high-throughput microfluidic devices, the lifespan of a number of mutants and the effect of several drugs on lifespan were analyzed. Yeast mother cells were loaded onto a device based on a 96 well plate device (FIG. 2A). Each of the 32 independent modules on the device (each module corresponds to a set of three wells in the microtiter plate) was loaded with one mutant strain, or a wild type strain treated with a particular drug at a given concentration, or a control wild type strain with no drug (typically two wild type controls are loaded to two different modules on the same plate at different positions). The cell loading protocol was optimized such that the majority of the trapping units (generally >80%) were loaded with a single mother cell. After cell loading, the multiwell plate was incubated at 30 °C for 84 hours, at which time almost all of the mother cells had died. After the incubation period, images were taken at 20 positions within each observational area (aligned with the middle well of each module). Because there are twenty positions within each observational area, and each of the twenty positions contains 11 trapping units (See FIG. 2B for an image of one of the twenty positions within the observational area of one a module), such that a total of 220 trapping units are imaged per module. Because there are 32 modules per 96-well plate, a total of 7040 trapping units can be imaged per plate. The total number of cells in each trapping unit was counted and the fluorescent signal was used to determine the number of DAP mother cells loaded in the trapping unit, allowing the lifespan of the mother cells to be determined unambiguously.

With more than 80% of the trapping units loaded with a single DAP mother cell, the RLS of more than 160 cells per module was obtained (80% of 220), leading to robust lifespan curves for each mutant or drug treatment. Overall, the DAP system and 96-well device allows the measurement of lifespan of mutants and/or drug treatments with high throughput, and without the need for media flow or continuous time-lapse imaging (which requires hundreds of images at each position). An exemplary throughput achieved was 640 strains/drug-concentrations per person per microscope per week.

Many genes that affect replicative lifespan (RLS) in the budding yeast *S. cerevisiae* also affect aging in other organisms such as *C. elegans* and *M. musculus*. The RLS of yeast mutants with single deletions in non-essential genes has been analyzed systematically by using the traditional microdissection technique, and years of work has been compiled (See M. A. McCormick et al., (2015) A Comprehensive Analysis of Replicative Lifespan in 4,698 Single-Gene Deletion Strains Uncovers Conserved Mechanisms of Aging. *Cell Metab.*22 (5): 895-906). In that analysis, many single gene deletions found to extend RLS in yeast were clustered in functional pathways, and a highly significant amount of overlap was found in the functional clusters of genes associated with RLS extension in yeast and the genes associated with lifespan extension in the worm *C. elegans*. Because there is such a high degree of conservation in lifespan regulation between these very distantly related species (yeast and worms), the genetic pathways that can alter lifespan and aging in other organisms, such as humans are predicted to also be conserved.

Previous studies indicate that deletions of the yeast genes FOB1, GPA2, or SGF73 extend replicative lifespan. FOB1 deletion extends lifespan by reducing extra-chromosomal ribosomal DNA circles (ERCs) (Defossez et al., (1999) Elimination of replication block protein Fob1 extends the life span of yeast mother cells. *Mol. Cell* 3:447-455). Viability of mother cells in liquid culture is regulated by SIR2 and FOB1, two opposing regulators of RLS in yeast, and viability curves of these short- and long-lived strains can be easily distinguished from wild type, using a colony formation assay. (Lindstrom and Gottschling, 2009, Genetics, 183: 413-422). Furthermore, studies have shown that dietary restriction fails to increase the RLS of sir2Δ single mutant cells lacking the Sir2 histone deacetylase, but robustly increases the RLS of sir2Δ fob1Δ double mutant cells (M. A. McCormick et al., (2015). *Cell Metab.*22 (5): 895-906; Delaney et al., 2011b; Kaeberlein et al., 2004; Lin et al., 2000).

Figure 3A:
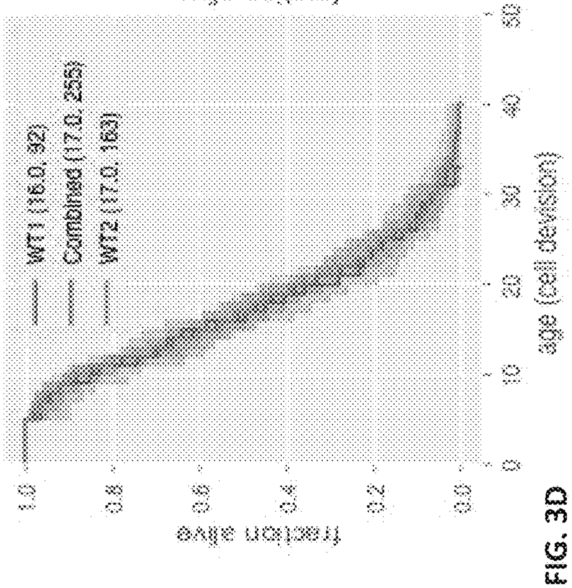
FIGS. 3A-3F depict the identification of genetic mutations that extend RLS using the yeast DAP strain and microfluidic device according to an embodiment of the present disclosure. Lifespan curves are shown for wildtype (WT) controls (FIG. 3A), fob1Δ deletion mutant (FIG. 3B), hom2Δ deletion mutant (FIG. 3C)
Figure 3B:
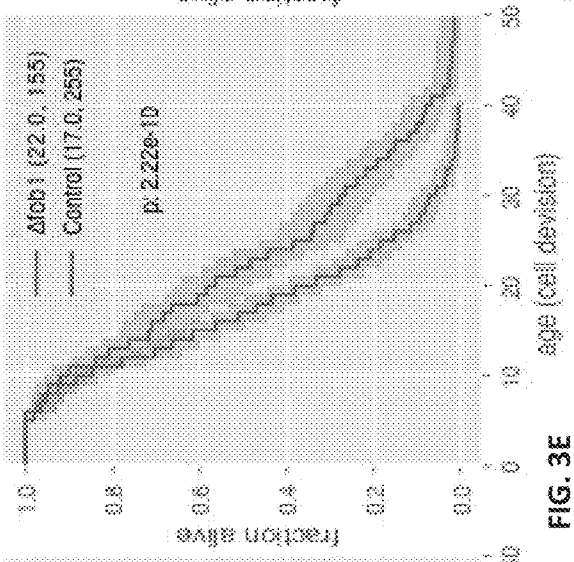
Figure 3C:
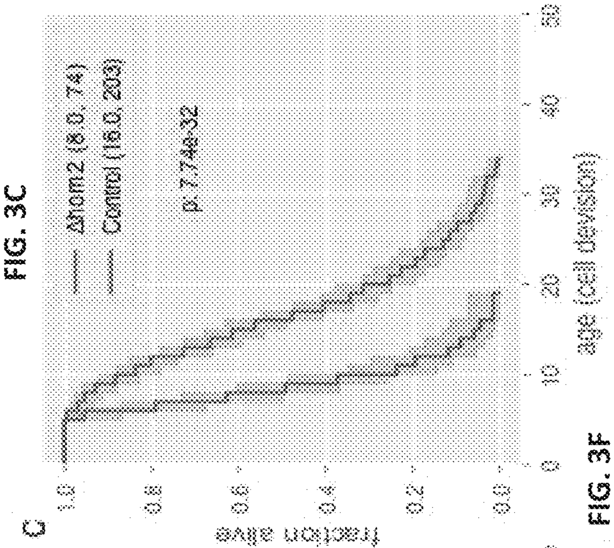

Several of the previously identified genetic mutations associated with aging in yeast were tested for their effects on lifespan by deleting the genes in the parental strain with DAP construct and measuring replicative lifespan with the described device. In general, the lifespan measurements agreed well with those obtained using the original mutants without DAP and the traditional micro-dissection technique. Two examples are shown in FIGS. 3B and 3C, where fob1Δ is a classical long-lived mutant discovered from yeast aging studies (Defossez et al., (1999) *Mol. Cell* 3:447-455). Fob1 encodes a nucleolar protein required for replication fork blocking, and deletion of Fob1 is thought to extend lifespan by reducing the toxic extra-chromosomal rDNA circles. Hom2 encodes an enzyme in the homoserine biosynthesis pathway and the deletion mutant was found to be short lived from the systematic deletion library screen (M. A. McCormick et al., (2015). *Cell Metab.*22 (5): 895-906). The measured lifespan showed that fob1Δ and hom2Δ deletion mutants are long and short lived with strong statistical confidence with 30% lifespan extension ($p=2.2\times10^{-10}$) and 50% lifespan reduction ($p=7.7\times10^{-32}$) respectively (FIGS. 3B-3C). The lifespan assay herein disclosed is robust and reproducible, as shown from the two nearly identical lifespan curves for the wild type controls from two modules at different positions on the same plate (FIG. 3A).

To further demonstrate the utility and power of the DAP system, a screen was conducted for long-lived mutants, having mutations in essential genes. Essential genes are those required for the viability of the cell, and which are more likely to be conserved in mammals. Due to their essentiality, these genes cannot be deleted in haploid yeast cells. As a consequence, these genes have rarely been analyzed in the context of aging. Previously, a library of hypomorphic alleles of essential genes was constructed (called the DAmP—The Decreased Abundance by mRNA Perturbation Library) (19); each of the strains in the library has the expression of one of the essential genes reduced by reducing the stability of the mRNA through the disruption of the 3' UTR. Fifty DAmP strains were selected from this library, focusing on several functional categories known to influence lifespan, including genes related to protein translation (tRNA synthetase) and glucose metabolism. Starting from the disclosed DAP strain, the DAmP strains were constructed by altering the 3'UTR of the gene of interest to destabilize the mRNA, using a technique described by Breslow et al. (19). The 96 well device was then used to measure their replicative lifespans.

Figure 3D:
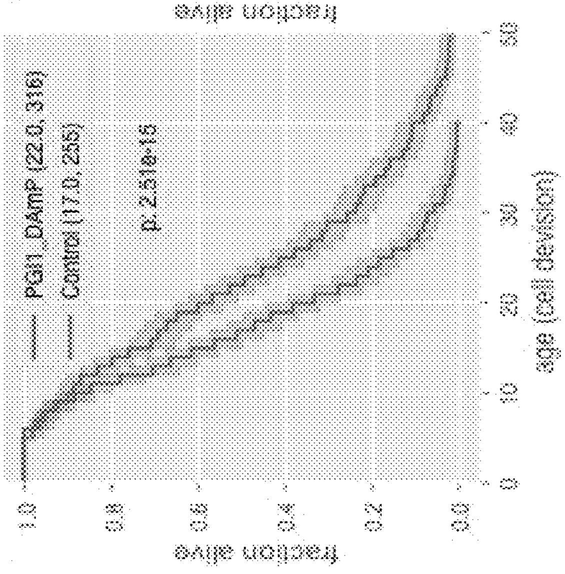
Figure 3E:
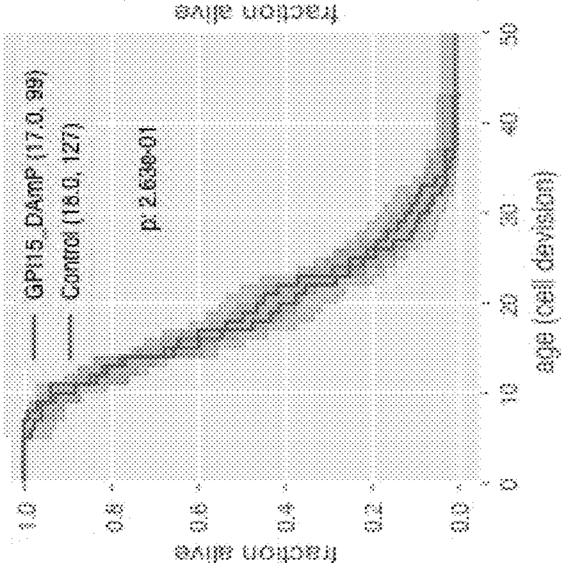
Figure 3F:
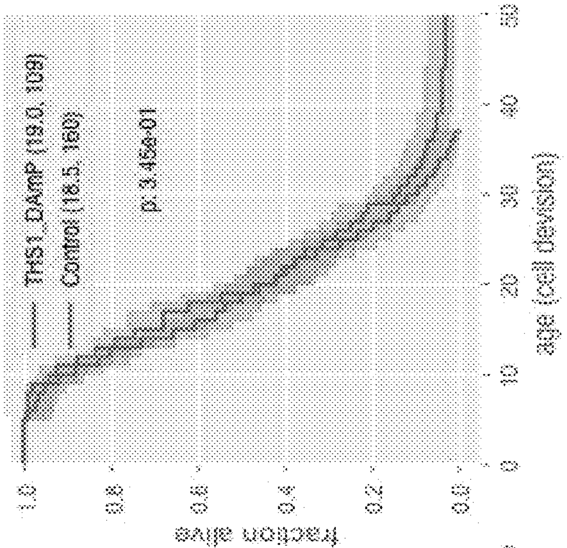

Shown in FIGS. 3A-3F are the lifespan curves allowing identification of genetic mutations that extend replicative lifespan (RLS) using the yeast DAP strain and the microfluidic device. Lifespan curves are shown for wildtype (WT) controls (3A), fob1Δ deletion mutant (3B), hom2Δ deletion mutant (3C), and FIGS. 3D-3F are DAmP alleles having reduced expression of the essential genes PGI1 (3D), GPI15 (3E) and THS1 (3F).

Most of these strains have the same lifespan as that of the wild type strain (FIGS. 3E, 3F), and some have shortened lifespan. An interesting candidate, PGI1, was identified with strong lifespan extension (30% increase, $p=2.5\times10^{-15}$) (FIG. 3D). The PGI1 gene encodes the glycolytic enzyme phosphoglucose isomerase that catalyzes the inter-conversion of glucose-6-phosphate and fructose-6-phosphate, which is a key step of glucose metabolism. It is likely that the reduction of this enzyme leads to an effect similar to glucose restriction, known to extend yeast lifespan. The lifespan extension observed in the strain carrying the PGI1 DAmP allele was remarkable, on par with the classical Fob1 deletion mutant, yet having a distinct mechanism. Because the structure of the protein encoded by PGI1 is known, the power and utility of present system and method was demonstrated and led to the identification of a promising target for design of small molecule drugs to delay aging.

Figure 4A:
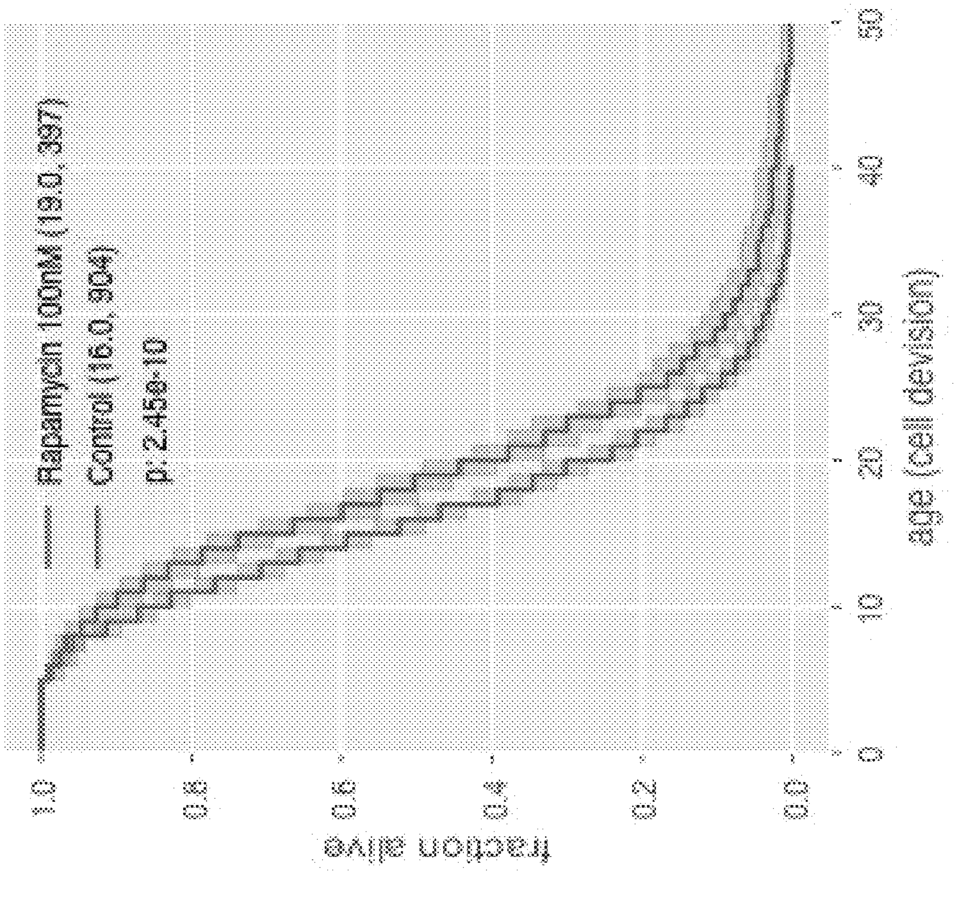
FIGS. 4A and 4B illustrate the effect of the compounds rapamycin (FIG. 4A) and spermidine (FIG. 4B), known to affect RLS, as confirmed using the DAP strain according to an embodiment of the present disclosure.
Figure 4B:
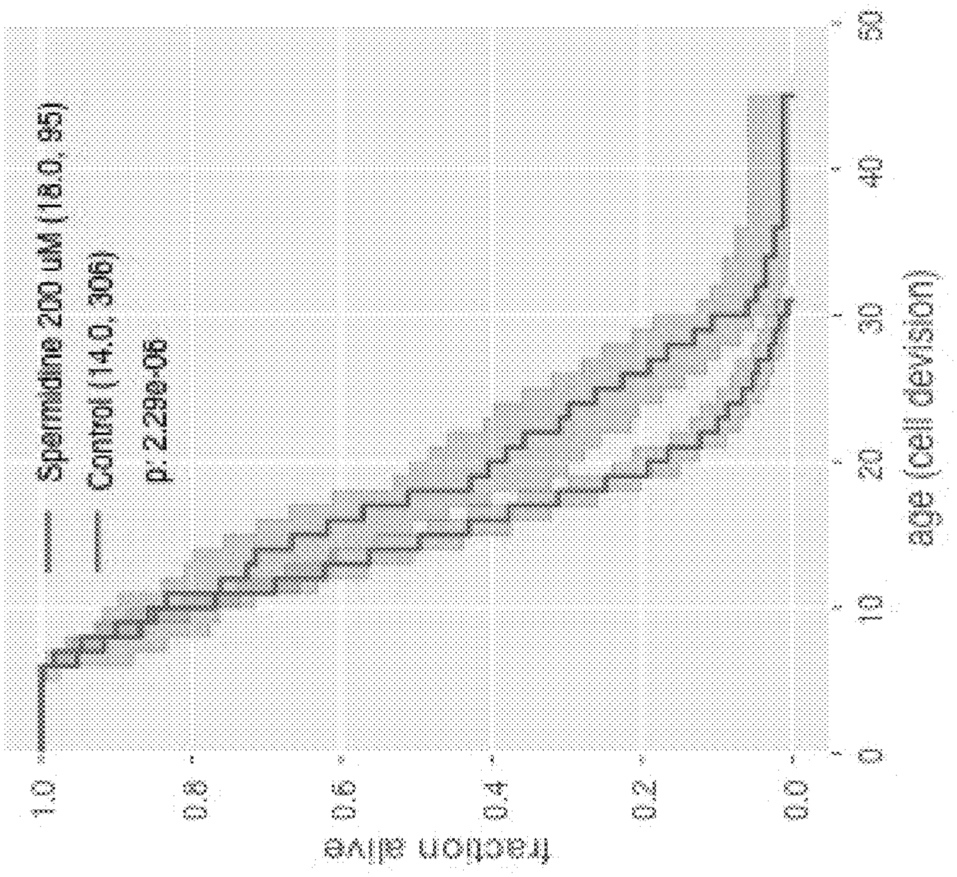

The system was further demonstrated to be useful as a drug screening platform; drugs known to extend the lifespan of yeast and other species, including rapamycin, metformin, and spermidine, were tested. For example, rapamycin is known to inhibit the TOR pathway and was shown to extend the lifespan of multiple species (1, 2, 20). Spermidine is a polyamine known to have a lifespan extension effect in several species, which has been attributed to its ability to induce autophagy (21). For each of these drugs, the lifespan of yeast cells was measured under a range of concentrations. Consistent lifespan extension by rapamycin at 100 nM concentration was observed across three independent experiments (19% lifespan extension, $p=2.4\times10^{-10}$), FIG. 4A). For spermidine, significant lifespan extension at 200 μM concentration (28% lifespan extension, $p=6\times10^{-6}$) was observed (FIG. 4B). The lifespan extension effect of metformin was not observed in the range of concentrations tested (from 4 μM to 8 mM) (data not shown).

Example 4: High Throughput Lifespan Assay by Combining DAP with Multiplex Barcode Sequencing A new high-throughput technology for measuring lifespan was developed by combining DAP with multiplexed barcoding and next generation sequencing, allowing the method to be used for cell counting in liquid culture without the need for the microfluidic device. As a proof-of-principle, a library of ORF deletion strains with the DAP and barcodes was constructed using SGA (systematic genetic analysis) technology, originally developed for double mutant construction (A. H. Tong et al., (2001) *Science* 294:2364-2368). The library was built by mating the DAP strain with the original barcoded deletion library strains in 96 well plates, sporulating, and selecting for haploids with markers for both the deletion/barcode and DAP (23). Using this method, approximately 3500 strains in the library were made. Some may interrupt the glucose repression system or the asymmetric partitioning of the cell membrane, thus leading to leakage in daughter cells. Any obviously leaky strains were removed by picking out those colonies that expand geometrically on glucose media plates. The less obvious, but still leaky strains can be identified from the growth curves.

Using the DAP system library of deletion strains bearing barcodes, initial experiments to measure their lifespan were performed. The experimental design was as follows (FIG. 5A): At time $t_0$, strains were pooled together into liquid media with glucose (DAP program on, daughters arrested), and the culture was partitioned into N identical aliquots with equal volume. Each aliquot i grows for a different time $t_i$ (i=0, . . . N−1), at which point a fixed amount of external reference cells with distinguishing bar codes were added and cells were harvested. After DNA extraction, barcodes were PCR-amplified, with an ith index sequence added. All the N sequence samples were then pooled together for next-generation sequencing. The external reference cells with distinguishing bar codes were used to normalize out the variability due to cell harvesting, DNA extraction, and PCR amplification. Taking Ng(i) as the number of sequence reads at time point i for the barcode of gene deletion g, the normalized read N'g(i)=Ng(i)/Nc(i) is proportional to the number of cells with barcode g at time i, where Nc(i) is the number of sequence reads at time i for the external reference cells. N'g(i)/N'g(0) then gives the ratio of the total number of cells over the number of mother cells for strain g at time i. For sufficient large $t_i$ (>3 days), this ratio will plateau, and the lifespan for strain g is given by the plateau value −1.

Figure 5B:
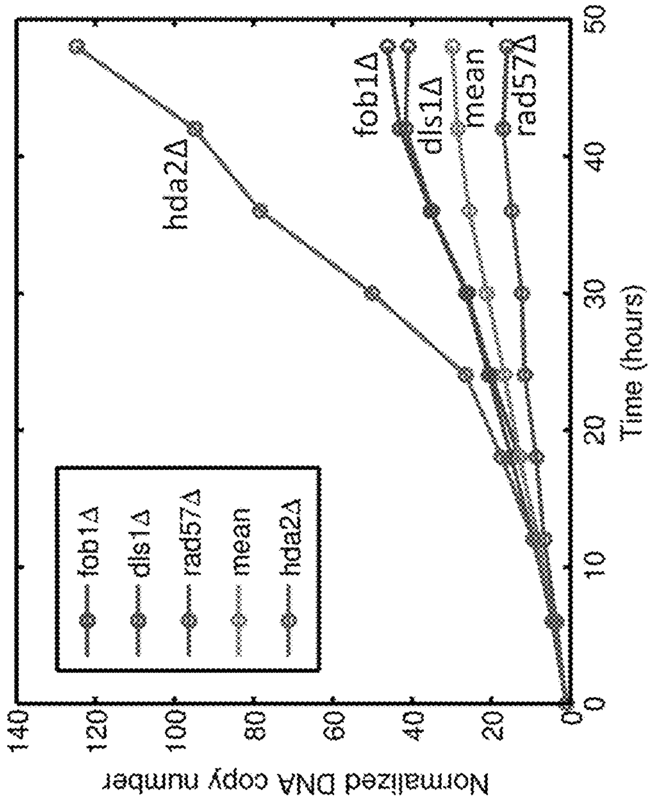
FIG. 5B shows long- and short-lived deletion strains identified in the screen according to an embodiment of the present disclosure. The fob1Δ mutant was known to have enhanced longevity, and RLS extension was confirmed in the dls1Δ mutant by direct measurement using the DAP system. The rad57Δ mutant is short-lived. The mean growth curve for all strains is also shown for comparison. The hda2Δ mutant is a leaky strain, as seen from the exponential growth curve.
Figure 5A:
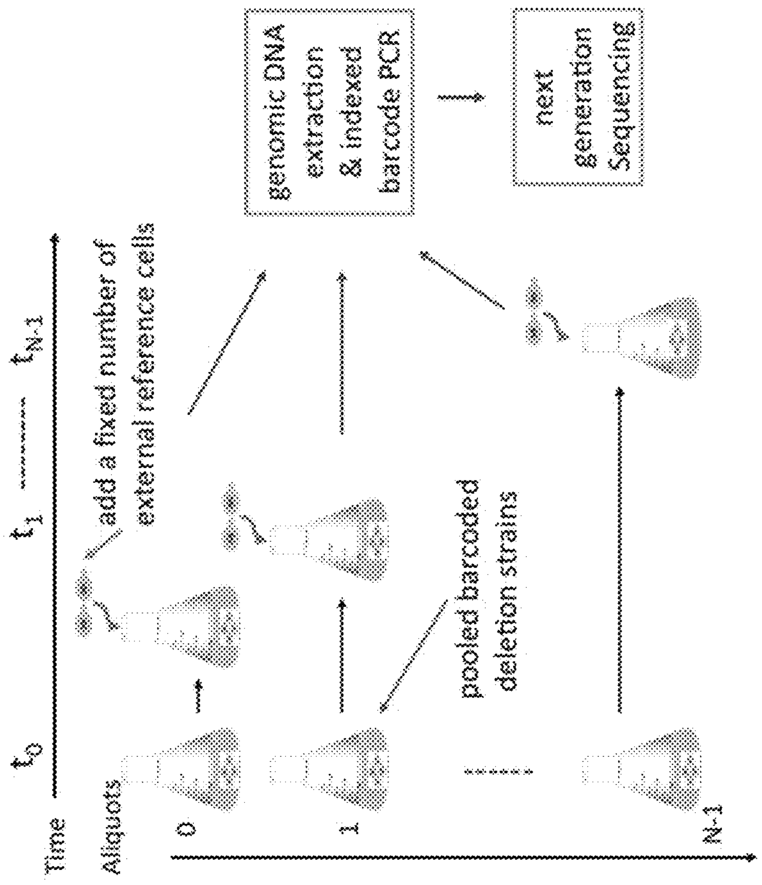
FIG. 5A depicts a schematic of the high-throughput screening system using the barcoded DAP mutant strain along with next generation sequencing (NGS) for identifying long-lived mutant strains according to an embodiment of the present disclosure.

FIG. 5A presents a schematic of the high-throughput screening system using the barcoded DAP mutant strain along with next generation sequencing (NGS) for identifying long-lived mutant strains. At time $t_0$, barcoded deletion strains with DAP are pooled together into liquid media with glucose (DAP program on, daughters arrested), and the culture is partitioned into N identical aliquots with equal volume. Each aliquot will grow to a different time, at which point a fixed amount of external reference cells with distinguishing bar codes are added, cells harvested and DNA extracted, followed by PCR barcode amplification and next generation sequencing. The normalized sequence reads (first by the reference and then by the initial value)−1 for a specific barcode then gives the number of daughter cells produced per mother cell by that mutant. FIG. 5B shows long- and short-lived deletion strains identified in the screen. The fob1Δ mutant is known to result in enhanced longevity, and RLS extension was confirmed in the dls1Δ mutant by direct measurement using the DAP system and microfluidic device. The rad57Δ mutant is short-lived. The mean growth curve for all strains is also shown for comparison. The hda24 mutant is a leaky strain, as seen from the exponential growth curve.

Further experiments were performed to measure the lifespan of deletion strains and confirm and/or identify several long-lived mutants, including genes known to be involved in lifespan as well as some new genes whose deletion was found to extend lifespan using the method described herein (FIG. 5B). For example, deletion of DLS1 (a subunit of the ISW2/yCHRAC chromatin accessibility complex; the ISW2/yCHRAC also includes Itc1p, Isw2p, and Dpb4p, and is involved in inheritance of telomeric silencing) was found to extend lifespan. The mutations and/or drugs identified using this high throughput screening were then confirmed by directly measuring the lifespan using the microfluidic device and time-lapse microscopy. The library construction and lifespan measurements took one person about two months, about 500 fold increase of throughput compared to the traditional microdissection method.

Example 5: High Throughput Drug Screening by Combining DAP with Multiplexed Bar Code Sequencing (Prophetic)

The approach described above for screening mutants can be generalized to screening for small molecules. This requires the development of a library of barcoded wild type strains with DAP so that each strain can be treated with a different compound, and a slightly different experimental procedure from that used to analyze ORF deletions. The DAP strain will be used with synthetic genetic array technology to generate a library of barcoded wild type strains with the DAP construct. Similar to the deletion library construction, this can be accomplished by mating the DAP strain to the barcode wild type library (24), sporulating and selecting for haploids with selectable markers for both the barcode and DAP. Leaky strains will be excluded.

Selectable markers can include, for example, dominant drug resistance gene cassettes that allow yeast to grow in the presence of drugs such as G418 (using the aphA1 gene for selection of drug resistant colonies), hygromycin B (using the hph resistance gene), cycloheximide (CYH2 selectable marker), phleomycin (ble selectable marker), chloramphenicol (using Cat or CmR selectable marker), nourseothricin (using nat selectable marker), glufosinate or bialaphos (using pat selectable marker), aureobasidin A (using AUR1-C marker) or zeocin (using ZEO (or Sh ble) marker). In some embodiments, the selectable marker is selected from aphA1, ble, Cat, CmR, CYH2, nat, kan, pat, AUR1-C and hph markers. In some embodiments, the selectable marker is hphNT1.

The experimental design is similar to that for measuring the lifespan of deletion library strains, with modifications (FIG. 6). Initially, barcoded wild type strains with DAP are cultured in 96 well plates in liquid media with galactose, each well containing one strain with a unique barcode. At time $t_0$, cells are transferred to 96 well plates with glucose (to turn on DAP) and one drug added to each well, matching a drug with a specific barcode. For measurement at N time points, N duplicates of the 96 well plates are required. At time point i, cell cultures from all the wells of the ith duplicate are pooled together, and a fixed amount of external reference cells are added. Cells from the pooled sample are harvested, DNA extracted, followed by barcode PCR amplification, with ith index sequence added. Finally all sequence samples from different time points are pooled together for high throughput sequencing. Let Nd(i) denote the number of sequence read at time point i (distinguished by the ith index sequence) for cells treated by drug d (based on the matching barcode from the well with drug d), the normalized read N'd(i)=Nd(i)/Nc(i) (Nc(i) is the number of reads for the externally added control cells) is proportional to the number of cells with drug d at time i, and N'd(i)/N'd(0) then gives the ratio of the total number of cells over the number of mother cells at time i for treatment by drug d. For sufficient large $t_i$, this ratio will reach a plateau, and the lifespan under drug d is given by the plateau value −1.

REFERENCES

1. J. M. Flynn et al., Late-life rapamycin treatment reverses age-related heart dysfunction. *Aging Cell* 12, 851-862 (2013).
2. D. E. Harrison et al., Rapamycin fed late in life extends lifespan in genetically heterogeneous mice. *Nature* 460, 392-395 (2009).
3. M. Kaeberlein, Resveratrol and rapamycin: are they anti-aging drugs? *Bioessays* 32, 96-99 (2010).
4. N. Barzilai, J. P. Crandall, S. B. Kritchevsky, M. A. Espeland, Metformin as a Tool to Target Aging. *Cell Metab.* 23, 1060-1065 (2016).
5. O. Medvedik, D. W. Lamming, K. D. Kim, D. A. Sinclair, MSN2 and MSN4 link calorie restriction and TOR to Sirtuin-mediated lifespan extension in *Saccharomyces cerevisiae. PLoS Biol.* 5, 230-241 (2007).
6. I. Bjedov et al., Mechanisms of life span extension by rapamycin in the fruit fly *Drosophila melanogaster. Cell Metab.* 11, 35-46 (2010).
7. A. A. Moskalev, M. V. Shaposhnikov, Pharmacological inhibition of phosphoinositide 3 and TOR kinases improves survival of *Drosophila melanogaster. Rejuvenation Res.* 13, 246-247 (2010).
8. B. Harrison, T. T. Tran, D. Taylor, S. D. Lee, K. J. Min, Effect of rapamycin on lifespan in *Drosophila. Geriatrics & Gerontology Intl.* 10, 110-112 (2010).
9. R. W. Powers, 3rd, M. Kaeberlein, S. D. Caldwell, B. K. Kennedy, S. Fields, Extension of chronological life span in yeast by decreased TOR pathway signaling. *Genes Dev.* 20, 174-184 (2006).
10. K. T. Howitz et al., Small molecule activators of sirtuins extend *Saccharomyces cerevisiae* lifespan. *Nature* 425, 191-196 (2003).
11. R. K. Mortimer, J. R. Johnston, Life span of individual yeast cells. *Nature* 183, 1751-1752 (1959).
12. Z. Xie et al., Molecular phenotyping of aging in single yeast cells using a novel microfluidic device. *Aging Cell* 11, 599-606 (2012).
13. Y. Zhang et al., Single cell analysis of yeast replicative aging using a new generation of microfluidic device. *PLoS One* 7, e48275 (2012).
14. D. L. Lindstrom, D. E. Gottschling, The mother enrichment program: a genetic system for facile replicative life span analysis in *Saccharomyces cerevisiae*. Genetics 183, 413-422, 411SI-413SI (2009).
15. S. Jarolim et al., A novel assay for replicative lifespan in *Saccharomyces cerevisiae. FEMS Yeast Res.* 5, 169-177 (2004).
16. M. C. Jo, W. Liu, L. Gu, W. Dang, L. Qin, High-throughput analysis of yeast replicative aging using a microfluidic system. *Proc. Natl. Acad. Sci. U.S.A* 112, 9364-9369 (2015).
17. M. A. McCormick et al., A Comprehensive Analysis of Replicative Lifespan in 4,698 Single-Gene Deletion Strains Uncovers Conserved Mechanisms of Aging. *Cell Metab.* (2015).
18. P. A. Defosscz et al., Elimination of replication block protein Fob1 extends the life span of yeast mother cells. *Mol. Cell* 3, 447-455 (1999).
19. D. K. Breslow et al., A comprehensive strategy enabling high-resolution functional analysis of the yeast genome. *Nat. Methods* 5, 711-718 (2008).
20. S. Robida-Stubbs et al., TOR signaling and rapamycin influence longevity by regulating SKN-1/Nrf and DAF-16/FoxO. *Cell Metab.* 15, 713-724 (2012).
21. T. Eisenberg et al., Induction of autophagy by spermidine promotes longevity. *Nat. Cell Biol* 11, 1305-1314 (2009).
22. A. H. Tong et al., Systematic genetic analysis with ordered arrays of yeast deletion mutants. *Science* 294, 2364-2368 (2001).

23. G. Giaever et al., Functional profiling of the *Saccharomyces cerevisiae* genome. *Nature* 418, 387-391 (2002).
24. Z. Yan et al., Yeast Barcoders: a chemogenomic application of a universal donor-strain collection carrying bar-code identifiers. *Nature methods* 5, 719-725 (2008).
25. M. Lucanic et al., Impact of genetic background and experimental reproducibility on identifying chemical compounds with robust longevity effects. *Nat. Commun.* 8, 14256 (2017).
26. C. Janke et al., A versatile toolbox for PCR-based tagging of yeast genes: new fluorescent proteins, more markers and promoter substitution cassettes. *Yeast* 21, 947-962 (2004).
27. C. Deng, A. N. Krutchinsky, See & Catch method for studying protein complexes in yeast cells: a technique unifying fluorescence microscopy and mass spectrometry. *Methods Mol. Biol.* 1163, 75-95 (2014).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

What is claimed is:

1. A vector comprising pIDS2GH (SEQ ID NO: 1) or pIDS2RH (SEQ ID NO: 2).

2. A yeast cell, comprising the vector of claim 1.

* * * * *